US012571042B2

(12) United States Patent
Burke et al.

(10) Patent No.: US 12,571,042 B2
(45) Date of Patent: Mar. 10, 2026

(54) MARKERS SPECIFIC FOR PLURIPOTENT STEM CELLS, AND METHODS OF USING THE SAME

(71) Applicant: FUJIFILM Corporation, Tokyo (JP)

(72) Inventors: Thomas Burke, Madison, WI (US); Steven Smith, Madison, WI (US); Anne Strouse, Madison, WI (US)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/930,901

(22) Filed: Sep. 9, 2022

(65) Prior Publication Data

US 2023/0122115 A1 Apr. 20, 2023

Related U.S. Application Data

(63) Continuation of application No. PCT/JP2021/009333, filed on Mar. 9, 2021.

(60) Provisional application No. 62/987,016, filed on Mar. 9, 2020.

(51) Int. Cl.
*C12Q 1/6881* (2018.01)
*C12Q 1/6869* (2018.01)

(52) U.S. Cl.
CPC ......... *C12Q 1/6881* (2013.01); *C12Q 1/6869* (2013.01); *C12Q 2600/158* (2013.01)

(58) Field of Classification Search
CPC .............................................. C12Q 2600/158
See application file for complete search history.

(56) References Cited

U.S. PATENT DOCUMENTS

| | | | |
|---|---|---|---|
| 9,862,943 B1 | 1/2018 | Kim et al. | |
| 2015/0011416 A1 | 1/2015 | Lei et al. | |
| 2018/0187147 A1* | 7/2018 | Saitou | G01N 33/56966 |
| 2021/0254185 A1 | 8/2021 | Taniguchi et al. | |

FOREIGN PATENT DOCUMENTS

| | | | | |
|---|---|---|---|---|
| JP | 2015-508661 A | 3/2015 | | |
| WO | WO-2018191520 A1 * | 10/2018 | | A61K 35/42 |
| WO | 2019/141878 A1 | 7/2019 | | |
| WO | 2019/240247 A1 | 12/2019 | | |

OTHER PUBLICATIONS

Miharada et al. Cell Reports. 2014. 7:1381-392. (Year: 2014).*
Lin et al. Stem Cells. 2011. 29:1963-1974. (Year: 2011).*
Qian et al. Stem Cells. 2016. 34:588-600. (Year: 2016).*
Song et al. J Am Soc Nephrol. 2011. 22:1213-1220. (Year: 2011).*
Tanaka et al. Develop Growth Differ. 2006. 48:381-390. (Year: 2006).*
Amano et al. BMC Developmental Biology. 2006. 6:11. (Year: 2006).*

Kim et al. Stem Cells. 2005. 23:458-462. (Year: 2005).*
NCBI_Blast_17930901_-_SEQ_ID_NO_2. Retrieved on Nov. 2, 2023 from the internet: blast.ncbi.nlm.nih.gov/Blast.cgi#alnHdr_2574211133. (Year: 2023).*
NCBI Blast_17930901—SEQ ID NO_ 5. Retrieved on Nov. 1, 2023 from the internet: blast.ncbi.nlm.nih.gov/Blast.cgi#sort_mark. (Year: 2023).*
NCBI Blast_17930901—SEQ ID NO_ 6. Retrieved on Nov. 1, 2023 from the internet: https://blast.ncbi.nlm.nih.gov/Blast.cgi#sort_mark. (Year: 2023).*
NCBI Blast_17930901—SEQ ID NO_ 13a. Retrieved on Nov. 14, 2023 from the internet: https://blast.ncbi.nlm.nih.gov/Blast.cgi#sort_mark (Year: 2023).*
NCBI Blast_17930901—SEQ ID NO_ 28. Retrieved on Nov. 2, 2023 from: blast.ncbi.nlm.nih.gov/Blast.cgi#alnHdr_2217356396. (Year: 2023).*
NCBI Blast_17930901—SEQ ID NO_ 4. Retrieved on Nov. 1, 2023 from the internet: https://blast.ncbi.nlm.nih.gov/Blast.cgi#sort_mark. (Year: 2023).*
NCBI Blast_17930901—SEQ ID NO_ 24. Retrieved on Nov. 1, 2023 from the internet: https://blast.ncbi.nlm.nih.gov/Blast.cgi#sort_mark. (Year: 2023).*
AL117378.1. Retrieved on Nov. 1, 2023 from the internet: *Homo sapiens* chromosome 6 clone dJ131F15, *** Sequencing in Progress *—Nucleotide—NCBI (nih.gov). (Year: 2023).*
NCBI Blast_SEQ ID NO_ 6 vs AL117378.1. Retrieved on Nov. 1, 2023 from the internet: https://blast.ncbi.nlm.nih.gov/Blast.cgi. (Year: 2023).*
NCBI Blast_SEQ ID NO_ 4 vs AL117378.1. Retrieved on Nov. 1, 2023 from the internet: https://blast.ncbi.nlm.nih.gov/Blast.cgi. (Year: 2023).*
NCBI Blast_SEQ ID No_ 5 vs AL117378.1. Retrieved on Nov. 1, 2023 from the internet: https://blast.ncbi.nlm.nih.gov/Blast.cgi. (Year: 2023).*
NCBI Blast_17930901—SEQ ID NO_ 23. Retrieved on Nov. 2, 2023 from the internet: blast.ncbi.nlm.nih.gov/Blast.cgi. (Year: 2023).*
NCBI Blast_17930901—SEQ ID NO_ 9. Retrieved on Nov. 2, 2023 from the internet: https://blast.ncbi.nlm.nih.gov/Blast.cgi. (Year: 2023).*
NCBI Blast_17930901—SEQ ID NO_ 10. Retrieved on Nov. 2, 2023 from the internet: blast.ncbi.nlm.nih.gov/Blast.cgi#alnHdr_2217356396. (Year: 2023).*
NCBI Blast_17930901—SEQ ID NO_ 11. Retrieved on Nov. 2, 2023 from the internet: https://blast.ncbi.nlm.nih.gov/Blast.cgi#sort_mark. (Year: 2023).*
NCBI_Blast_17930901_-_SEQ_ID_NO_1. Retrieved on Nov. 2, 2023 from the internet: https://blast.ncbi.nlm.nih.gov/Blast.cgi#sort_mark. (Year: 2023).*
NCBI_Blast_17930901_-_SEQ_ID_NO_6a. Retrieved on Nov. 2, 2023 from the internet: https://blast.ncbi.nlm.nih.gov/Blast.cgi#sort_mark. (Year: 2023).*
NCBI_Blast_17930901_-_SEQ_ID_NO_13. Retrieved on Nov. 2, 2023 from the internet: https://blast.ncbi.nlm.nih.gov/Blast.cgi#sort_mark. (Year: 2023).*
Chu et al. Genome Biology. 2016. 17:173, 20 pages. (Year: 2016).*

(Continued)

*Primary Examiner* — Joseph G. Dauner
(74) *Attorney, Agent, or Firm* — Sughrue Mion, PLLC

(57) ABSTRACT

The present disclosure provides markers specific for pluripotent stem cells. In particular, the present disclosure relates to nucleic acid and polypeptide markers that are selectively expressed by pluripotent stem cells; and to methods for detecting the presence and/or absence of one or a plurality of pluripotent stem cells, by detecting such markers.

25 Claims, 25 Drawing Sheets

Specification includes a Sequence Listing.

(56)            References Cited

OTHER PUBLICATIONS

Nguyen et al. Genome Research. 2018. 28:1053-1066. (Year: 2018).*
James A. Thomson et al., "Embryonic Stem Cell Lines Derived from Human Blastocysts", Science, Nov. 6, 1998, vol. 282, pp. 1145-1147 (4 pages total).
Kazutoshi Takahashi et al., "Induction of Pluripotent Stem Cells from Mouse Embryonic and Adult Fibroblast Cultures by Defined Factors", Cell, Aug. 25, 2006, vol. 126, pp. 663-676 (14 pages total).
"SOLiD® Total RNA-Seq Kit", Life Technologies, Jul. 2011, pp. 3-105 (106 pages total), Retrieved from the Internet: https://tools.thermofisher.com/content/sfs/manuals/cms_078610.pdf.
Database Accession No. HW965749, "Multimodal PCR Target Detection", Oct. 3, 2015 (1 page total).
Takuya Kuroda et al., "Highly Sensitive In Vitro Methods for Detection of Residual Undifferentiated Cells in Retinal Pigment Epithelial Cells Derived from Human iPS Cells", Plos One, May 2012, vol. 7, Issue 5, pp. 1-9 (9 pages total).
Written Opinion dated Sep. 8, 2021 issued by the International Searching Authority in Application No. PCT/JP2021/009333.
International Preliminary Report on Patentability issued Sep. 6, 2022 in International Application No. PCT/JP2021/009333.
International Search Report dated Sep. 8, 2021 issued by the International Searching Authority in Application No. PCT/JP2021/009333.

* cited by examiner

Hierarchical Clustering of All Cell Types Based on IPSC Specific Marker Panel

Cross Tissue Comparison of iPSC Specific Gene Expression Markers

FROM
FIG.
20D

Colors:
○ 3.00
◐ 0.00
● -5.00

Row dendrogram:
Clustering method:
UPGMA
Distance measure:
Euclidean
Ordering weight:
Average value
Normalization: (None)
Empty value
replacement: Row
average Column dendrogram:
Clustering method:
UPGMA
Distance measure:
Euclidean
Ordering weight:
Average value
Normalization: (None)
Empty value
replacement: Row
average

SEQUENCE LISTING

```
Sequence total quantity: 28
SEQ ID NO: 1            moltype = DNA  length = 808
FEATURE                 Location/Qualifiers
source                  1..808
                        mol_type = genomic DNA
                        organism = Homo sapiens
SEQUENCE: 1
actcagcccc cctgcaccca ggtgaaataa acagccatgt tgctcacaca aagcctgttt   60
ggtgatctct tcacatggat gcacatgaaa tttggtgctg tgactcagat cgggggacct  120
cccttgggag atcaatcccc tgtactcctg ttctttgctc catgacaaag atccacctat  180
gacctcaggt cctcagaccg accagcccaa ggaacatctc accaattgta aatcaggtga  240
agtatgaagt tatgaggaga aaggaacaga ggacaaccac acagagaaag tgtagcttta  300
tctactagag ctgaagacat tcaaatttat gatccaacaa ttctactctg aagtgcagtg  360
gtgtatatac tgcaacaatg tgtactcatg tgccctgaga actagatatg aaaaaacctt  420
acagcaatat gcataatagt aaaaaaaaaa aaaaaaaact ggaaacaaca aaaatgttca  480
ttgaccatat acaatgataa atgtggtata ctcgtagcat ggaaaactac acaacattga  540
aaatgaacaa actaaaactg tacacagcaa catgaacgaa ttccacagat aatattgagt  600
gaaagatacc agacaccaaa taatatccca tatgatttca tttacattaa atgtttttt   660
tttgagatgg agtctcgctc tgttgcccag gctggagtgc agtggcacaa tcttggctca  720
ctgcaacctc tgcttttcag gttcaagcta ttctcccact tcagcctccc cagtagctgg  780
gactacaggt acctgccacc acgcccaa                                     808

SEQ ID NO: 2            moltype = DNA  length = 1059
FEATURE                 Location/Qualifiers
source                  1..1059
                        mol_type = genomic DNA
                        organism = Homo sapiens
SEQUENCE: 2
gtgctggctt ccccttcgcc ttctgccgtc atttgacagg aaattaggat gagcacgagc   60
aaagtcggtg gtcacaaggg agcagccagg ccagtcctgc ttaaactcct gctgttacat  120
gtttgcgatt gaactcgtag caagctgccg atggaacaca acctgcctcc ggcacagacg  180
ccgatcttca atcccttctc cccagcaccg gtgacagccc tagtcatcct tcaaggccca  240
gttcaaatgc ctccatctcc ataccatttc agttcgtggt tggggatagg agctcccgtc  300
gcgatcgtca tctttctgct gcagacagat tttgtttccc tctgtaaagt tggagtgcag  360
gggacaaggc tctgaacata gcatttaagt gacagagatg gttgtggtca tgtcccagta  420
tgtatttatc tatctcctgc tccagtaaat gtcacactcc ccgggcagc gagggtgtca   480
ccatctcggt gtcccacag cacctagcac agtctcccag acgatccagg gcagaccctt   540
cgcatgggaa cgcaagtccc tgtttgtccg ggtcactcag gtttacgcct attgtcctgt  600
aattatttat gcaccctctt ttgctgtcat aggtgttggg ttggaacagt caccctattt  660
agcacacacc tattaagcca aagcacctta gtgtgtaggc ttccctcacc caaacctgtt  720
cccaaaggtc ctttctcacc ggctactttg ggggccccag taatcttccc gacccctctg  780
gtcagggcca gagtggggag caagtgtcta aagcaaggcc ttcaacaagg tcccttccct  840
gagagactca gtttgtgacg cttgtgattg tgaagctcaa atggattatg tgactccaca  900
taactctgca aactgtggtg cgccctatta ttgccgttta acttgtcagt gtcggttctg  960
caccccctgca ggctctgtag gggctggaga agaacacttg atttggaatt tcggtaatag 1020
ccagtgagct aagaaccaca taaaataatg cagatcata                        1059

SEQ ID NO: 3            moltype = DNA  length = 1170
FEATURE                 Location/Qualifiers
source                  1..1170
                        mol_type = genomic DNA
                        organism = Homo sapiens
SEQUENCE: 3
tgctggcttc cccttcgcct tctgccgtca ttgtgagccg tggggaggcc ttgagcgccc   60
cctggaggtg acactctgcc actacacata ggaaaccacc tggaaaccca accacagtgt  120
ctgatgtgac ttttcttagt gacaggaaat taggatgagc acgagcaaag tcggtggtca  180
caagggagca gccaggccag tcctgcttaa actcctgctg ttacatgttt gcgattgaac  240
tcgtagcaag ctgccgatgg aacacaacct gcctccggca cagacgccga tcttcaatcc  300
cttctcccca gcaccggtga gcccctagt catccttcaa ggcccagttc aaatgcctcc   360
atctccatac catttcagtt cgtggttggg gataggagct cccgtcgcga tcgtcatctt  420
tctgctgcag acagattttg tttccctctg taaagttgga gtgcagggga caaggctctg  480
aacatagcat ttaagtgaca gagatggttg tggtcatgtc ccagtatgta tttatctatc  540
tcctgctcca gtaaatgtca cactcccgg ggcagcgagg gtgtcaccat ctcggtgtcc   600
ccacagcacc tagcacagtc tcccagacga tccagggcag acccttcgca tgggaacgca  660
agtccctgtt tgtccgggtc actcaggttt acgcctattg tcctgtaatt atttatgcac  720
```

```
cctctttttgc tgtcataggt gttgggttgg aacagtcacc ctatttagca cacacctatt   780
aagccaaagc accttagtgt gtaggcttcc ctcacccaaa cctgttccca aaggtccttt   840
ctcaccggct actttggggg ccccagtaat cttcccgacc cctctggtca gggccagagt   900
ggggagcaag tgtctaaagc aaggccttca acaaggtccc ttccctgaga gactcagttt   960
gtgacgcttg tgattgtgaa gctcaaatgg attatgtgac tccacataac tctgcaaact  1020
gtggtgcgcc ctattattgc cgtttaactt gtcagtgtcg gttctgcacc cctgcaggct  1080
ctgtaggggc tggagaagaa cacttgattt ggaatttcgg taatagccag tgagctaaga  1140
accacataaa ataatgcaga tcatatgaaa                                    1170

SEQ ID NO: 4          moltype = DNA  length = 2305
FEATURE               Location/Qualifiers
source                1..2305
                      mol_type = genomic DNA
                      organism = Homo sapiens
SEQUENCE: 4
acaaagcctg tttggtggtc tcttcacacg gacgcgcatg aaatttggtg ccatgactcg    60
gatcggggga cctcccttgg gagatcaatc ccctgtcttc ctgttctttg ctccgtgaga   120
aagatccacc tacaacctca ggtcctcaga ccgaccagcc caaggaacat ctcaccaatt   180
ttaaatcagc tccaggagaa tgggtgactt gaactggcaa ggagcaacct gctctctcca   240
cgggcctctg gaaccccggc aagagaagat cccttgatca ccatggacac tcaagttggc   300
aagaagagct ccttagagaa gtcgtgggag ggcaagcaag ctgatgtgga gccaggacga   360
tttgatgtgg gagcacctgc agtggagcac agccagggag agccatctcc ccaggcctga   420
cttgctccca taggagactt tagccctagg ggaactgtcc atcctgatct ctgcagggtg   480
gtcttgtcca tcagacaggg ctgattcgac ctgagcaccc cttggtctgc tggcctttct   540
ggggtcccag cctggccaga cctgcttgca gggcagtctt gggtgccctg gaggccacgc   600
catagcttct gtgctggcag atagtatctg actggtggag agctccagca aggctgcccc   660
taggccacac accagcccat ccaccccctc cccacactgc agcttcccta ggcccaggaa   720
actcctcacg tgtctttgct ggcacaagtc tgcacaggta ggttttgcct tccttgccct   780
gccagtgcat gggagtgtag tctgcccccc tgccccgtct ggctgtcatt gaagacagag   840
ccttggtggg cacagagcaa gccagctccc cgcaacgcc cacctcaaca cctggccctt   900
gtgctaacac tgtgcagaga acagtggacc ctgctcgcac cctgagtgat cactcctgct   960
tgtggggcac agagaaggtg tccagacctg ctcacgccag tgccctgccc ccaagccaac  1020
accacatcca acaggagcct gcacccagtc ttcagcatag aggtgaaaga tctctacgag  1080
gagaactatg aaacactgct caaaataatc aaatatgata caagcaaatg gaagagcatg  1140
caatgctcat ggataggaag aatcaatatc ataaaaatgg ccatactgcc caaagcaatt  1200
tatagattca atgctattcc tattaaacta ccattgatat tcttcacaaa actagagaaa  1260
actattttaa agttcatatg gaaccaaaaa agagcctgaa tagccaagga aatcctaagc  1320
aaaaagaaca aagctggaag catcatgcta cccaacttca aactatacta caggactaca  1380
gtaaccaaaa cagcgtggta ctggtacaaa aacagacaca tagaccaatg aaacagaata  1440
gagaacccag aaatggttct ctatttcaca cacctacaac tatctgatct tcgacaaacc  1500
tgataaaaac aagcaatagg gaaatgatte tgtattcatt aaatgatgct ggaataactg  1560
gctagccata tgctgaagat taaaactgga cccccttcctt atactgtaca caaaaatcaa  1620
ctcaaaatgg atgaaagact taaatgtaaa acccaaaact ataacaacaa tagaagacaa  1680
cctaggcaat accatcttgg atataggaac aggcaaaaat ttcatgacaa agacaccaaa  1740
agcaattgaa acaaaagcaa aaattgaaaa gtgggttcta aataaaacta aagagctcct  1800
gcacagcaaa gaaaatacaa acagagtgaa cagacaacct acagaatgac agtatctgca  1860
aactatacat ccaacaaaga tctaatattc agcatctata agaaacttaa acaaatttcc  1920
aaaaacaacc ccattaaaaa gtgggcaaag catatgaaca gacacttttc aaaagaagac  1980
atacatgcag ccaacaaaca tgaaaaaggc tcaacaccac caatcattag agaaatgcaa  2040
atcaaaacca caatgagata ccatctcaca ctagtcagaa tggctgatgg ctgttattaa  2100
aaagtcaaaa ataacagat gctggcaagg ttgtggagaa aaggcaatgc ttatgcactg  2160
ttggtgggag tataaattag ttcaatcatt gtggttgaca gtgtggtgat tcctcaaaga  2220
tctgaaaaca gaaatataat tctacctagc aatgctacta ctgggtatat acccaaagaa  2280
aaataaattg ttcaattata aagac                                        2305

SEQ ID NO: 5          moltype = DNA  length = 601
FEATURE               Location/Qualifiers
source                1..601
                      mol_type = genomic DNA
                      organism = Homo sapiens
SEQUENCE: 5
caaagcctgt ttggtggtct cttcacacgg acgcgcatga aatttggtgc catgactcgg    60
atcgggggac ctcccttggg agatcaatcc cctgtcttcc tgttctttgc tccgtgagaa   120
agatccacct acaacctcag gtcctcagac cgaccagccc aaggaacatc tcaccaattt   180
taaatcagga gcttactaca cgtgccggca atctggccac tgggccaagg aatgcccgca   240
gcccgggatt cctcctaagc cgcgtccat ctgtgtggga ccccactgga aatcggactg   300
ttcaactcac ctggcagcca ctcccagagc ccctggaact ctggcccaag gctctctgac   360
tgactccttc ccagatcttc ttggcttagc ggctgaagac tgacactgcc cgattcgttt   420
ggaagccccc taaaccatca cggatgccga gcttcgggta actctcacag tggaagggac   480
gtgcatgaaa gttaggggta gaagaaaaga tggattgagg ttgtcctcag actttccatg   540
gtatctgagc tgttttcctc ttccggaatt gtgtctcata tgaagttcct cttcatttga   600
g                                                                    601

SEQ ID NO: 6          moltype = DNA  length = 712
FEATURE               Location/Qualifiers
source                1..712
                      mol_type = genomic DNA
                      organism = Homo sapiens
```

-continued

```
SEQUENCE: 6
ccctgagaca ctttacagcc ctagaccta aaaggtcaaa aggccgtctt attctcaaaa   60
tacattttat tacccgacat taataaaaca ttaaataaaa ctccaaaaat taaattccgg  120
ccctcaaacc tcacaacagg atttaattaa cctcgccttc aaggtgtacg ataatagaaa  180
aaagttgcaa ttccttgcct ccacggtgag acaaacccca gccacatctc cagcacacaa  240
gaacttccaa atgcctgaac cgcagaggcc aggcattcct ccagaacctc ctcccacagg  300
agcttactac acgtgccggc aatctggcca ctgggccaag gaatgcccgc agcccgggat  360
tcctcctaag ccgcgtccca tctgtgtggg accccactgg aaatcggact gttcaactca  420
cctggcagcc actcccagag ccctggaac tctggccaa ggctctctga ctgactcctt  480
cccagatctt cttggcttag cggctgaaga ctgacactgc ccgattgcct tggaagcccc  540
ctaaaccatc acggatgccg agcttcgggt aactctcaca gtggaaggga cgtgcatgaa  600
agttaggggt agaagaaaag atggattgag gttgtcctca gactttccat ggtatctgag  660
ctgttttcct cttccggaat tgtgtctcat atgaagttcc tcttcatttg ag           712

SEQ ID NO: 7               moltype = DNA  length = 778
FEATURE                    Location/Qualifiers
source                     1..778
                           mol_type = genomic DNA
                           organism = Homo sapiens
SEQUENCE: 7
atgtgggtgg ctgagaaggg cactagggtg ggggtggctg gaggaatttt aagtgctgtg   60
atgaaatggg cacccttctc tgccctccat cgccaagccc tacacctctg cgaagactgt  120
gacacataaa gtcctgtgtc aacgatctgt gcccgcagag agagcctgct ccagcctctt  180
tgctacagcc ttgagtcttc tgctgaagct gtggagacta ccaaatggac tcgtctagat  240
ttcacatgca acgtggctct gccttccctg agcactctgg gcctttccat ggagacagaa  300
tgaatagata atgggctgtc accatcttgc actgccagct gtcctctctg aaggttgaac  360
tcctaacaga agtttcctca tgtttgtggt agcagcacct tgagaagtag agaagacaag  420
aagaaaaaag gagtcagcac agatgacaag ctctgctttt tagtgtacat ggtcttcccc  480
agtatgcaca ttctttttcct attcttgact tatctcccctt aacgataaaa tggccaagtt  540
agaaaccta gacactctta ttctcttttc tttcttttctt tcttttcttt cttaagagac  600
agggtctcat tctgtcaccc aggctggagt acagtggcac aactgtaggt agctcactgc  660
agcctgaaat tcctaggctc aagtgattct cctgcctcag cgacttcgga gtggctgaga  720
ttccaagctt aaaccattgt gtcctgcact tctcactttc atggctgtta tcctgggg    778

SEQ ID NO: 8               moltype = DNA  length = 1017
FEATURE                    Location/Qualifiers
source                     1..1017
                           mol_type = genomic DNA
                           organism = Homo sapiens
SEQUENCE: 8
cataggctcc agaaaacaag aagcaagact ggaaagctgg ggatgattgt acgccctcgc   60
ctgaatctta cgtggttcct ccttcttcca cctggccagt gcagagccgt gggtgccacg  120
tggccacttc tggattgggt tccccttggc ctgccaccct gtccttctgc tttcccactt  180
tgccagccag agtcaatttg aggacgccaa gttctcctct ccatacagag ctcctggtct  240
ccttgtaact tgtaactcct gggcacagtt acaagtgctg aattcttgcg aggatgaact  300
caagatacaa aatatgcttg gcaactcacc cctgagtggc cacaggcaca cgcaggagtc  360
gaacccaccc acctctgctg acagtcatgg gtcaagctca aagtcctggc tgcttctctg  420
ctcaagatct gtgcccgcag agagagcctg ctccagcctc tttgctacag ccttgagtct  480
tctgctaaga aaagacacag aggcaaagag aaacacatag agaggagaat gcctcgtgaa  540
aatggagacc gagattggtg caatgtgtcc acaagccagg gaatgccaac gtggccagca  600
accaccagaa gctgggagag aggcatggaa cagagtcctg ggagcctcca gaaggaacca  660
accctgttga taccttgact gaaaacttcc agcctccaga actgtgacag aattaatttc  720
tgttatttaa agccattcag tctgtggtaa tttgttacat cagccctgaa tagcaaatac  780
agatgaccca ggtttaaatc ctagttctgc cacttatgag cgtgggtaca taactacttt  840
ctagagcccc ggtttcctca tctgtaaaaa acctcatacg gttattaaga agatcaaatg  900
agatacaaac ataaattctt aacagtgctg gcatgttaat tgttcaataa atatgagtta  960
tttacaacaa ttgtgatagt aatgagtaac acagagaaat gagaattgac ttaacag    1017

SEQ ID NO: 9               moltype = DNA  length = 818
FEATURE                    Location/Qualifiers
source                     1..818
                           mol_type = genomic DNA
                           organism = Homo sapiens
SEQUENCE: 9
tggtagtgaa taactctcac aagatctgat ggtttgataa ggggaaaccc gtttcacttg   60
gctttcattc tctcttgcag ccaccatgcc accttccacc atgattttga ggcctcccca  120
gacacgtgga cctagcaaca catgttctaa catgtgtgag actgactgcc tctcctctat  180
gaagagatgc cagtgacagc caggactggt gtaggctcta ttgagcatca cagtcatatg  240
tgagtgccca agagaagcta ttcactttct cagatgcggt ttgcagaggg aacttcacag  300
gctctctggg attgctcaca tttggcagct aaagtggaat caccaatcca aaatactcac  360
cccaggcgtg gggtcactcc cagtggcgga gatgccctgc atttccattg cctggactga  420
ggaacagatg aaaggggaac cacaccaggg tggtggcctg ggatgtgcct actccctaag  480
ccaagcttct ctgtcctgag tgggcttagg gtccctgca gcgtgggtgt taaatgctgc  540
ttcctaggcc tcaccctcag agcttccagt tcagtcgagt ccaggtccct aacctgtgc  600
cgtccaattg attttgatca ggtgcccat ggcccacctt tgagaagcag atcgagtcca  660
cctgtgcatc ttccctgttg tccctaaaaa taaggctaaa aaaaggcacc agttcaaaaa  720
tccagttat ttgtttgaag ttcaggttta cagttcctcc aattctcaga tcgcagaaga  780
agcatctgga aggaaatgac ccctgcaccc accacacc                          818
```

```
SEQ ID NO: 10          moltype = DNA   length = 531
FEATURE                Location/Qualifiers
source                 1..531
                       mol_type = genomic DNA
                       organism = Homo sapiens
SEQUENCE: 10
actgacactt ttcggactca gcctgcctgc acccaggtga ttaaaagctt tattgctcac    60
acaaagcctt tttggtggtc tcttcacatg gatgcgcatg aaatttggtg cggtgactcg   120
gatcggggga cctcccttgg gagatcaatc ccctgtcctc ctgttctttg ctccgtgaga   180
aagagccacc tacgacctca ggtcctcaga ccaaccaggc caagaaacat ctcaccaatt   240
tcaaatccgc cactcccaga gcccctggaa ctctggccca aggctctctg actgactcct   300
tcccagatct tctcggctta gcggctgaag actgacactg ctcaatcacc ttggaagccc   360
cctagaccat cacggacgcc gagcttcagc aggagaagac aaggagatgg agagactgtc   420
aacctagaac cagtaatgac cagttccaac ttaattacag aaaggagaa aagatcaatc    480
atttaagttg cttcatcgtc taaataaaag tgttttggct gttgaaacat g            531

SEQ ID NO: 11          moltype = DNA   length = 2119
FEATURE                Location/Qualifiers
source                 1..2119
                       mol_type = genomic DNA
                       organism = Homo sapiens
SEQUENCE: 11
ggacttagcc cacctgcacc caggggaaat aaacagcctt gttgctcaca caaagcctgt    60
ttggtggtct cttcacacgg acgtgtgtga caaggaacac cctccttgag cacagggga    120
gggtgaatat cagaactgaa tctgacttct gacaacatag gagctgaagg gaccttggat   180
gttgggtaag cagttcccac tgtctgtcac aagccctaat aaaatacaag taagagaaaa   240
gaacaaaact ggggcaatct aatcaagaaa ggctttctgg aatgcatgag gccccagcga   300
gatctaaaat tcctagatgg acttggtgtt gtggaagcaa gacagcagtc gggcaaagga   360
gagacaggaa gcaaatgaat tctaccttgc caacaatggg aaacagacat acttaatgtg   420
agtagagagg tagccttggc caggaaagtt tgtttgaaga tcctggtctg tcttgacttt   480
aaatcacttg cctttggaat ggaagagaac agacatctca tcaaatgaac caatctgaat   540
gcaaggagca cccgaatcca tccccactca ggaatcctgg ttacagatgc taaaagatgt   600
ctttgacagt gaacagtggg tcataagatc tatttctgcc tcctgtctgt gactcactgg   660
atgactcaag gtgaatctct cccatttct gagtatctgg cccccatcca tgaagaacag    720
aagatcacat cagtatttcc cttcggcaag gttggcccc gctgcagcaa ctgtgcaaag    780
accaccagac tgccctctct gccagcttac tcttcagcct ttctggctct ttctcccact   840
tccacatccc tgcttcattt ttcttttct cctttgcaa atagcattgc tccaaagcaa    900
cccaggcacg tgtcttgggg acagcgctgc gagctacccc tgagctgtgg ggagcaggcc   960
caagattgtt tgctattagc aactcctgtt tgcaggataa ataaagcgaa cctgagtgca   1020
ggctcctgtg ggctgggaca ttttcattct gcagcaggtc agcttccatt ccactagggg   1080
gctttgaatg ttaataggca tttctttcca ggtaccttc tcctttctct acagtgcacc    1140
agtccctgtg ggaccttcca ttggcatcct acggagagat tattactctt ttcattgttt   1200
tccttacaaa ttagtttctg gatttaatgg ctttggttgc tgagcagatt ttggaaattg   1260
gggcagatgg tggggtgggg tgatctgcag agcccattat gggcactggg ttattgactg   1320
cttgggattt aaggtggaat taacgctttc ctgtttcttg gggaattttg cgatggggtt   1380
ggaccttctt ttcccttaga aggaattgtg tttgttgtta ttgcatgttt aagaagcttc   1440
tagaaattgt agctctggaa tacaataggt agagaatgca ggtttttaat gggatgtggg   1500
ggagtgttgc tcagttgtgg gaagatttgt aataatggtt gggactgggg atagagcgtt   1560
acctgaggac ggttttatta atgccacaaa gcataaagtt taaaaaaaaa gaaaaaagaa   1620
aatccagggg tgtcttactg tcagaagctt tggaaccatg ttgaataggt gctgggtaaa   1680
atgagactga gacctgctgg gctgcattcc caggaggtta gggattcgca gtcacagggt   1740
gtttacagtt aagggaacag gttaataatg tttaccaaac agacccagga cttaacagac   1800
ccaagaaatg tcttgatgtc ctgctatctt aagcacaaaa gcattctttg tttagtaata   1860
aattttgctt taaagatagt aatatagatt cttgcaaaag tcagtagtta cacaaggatt   1920
aacaatcctt tgtcatgagc ccttgtaata gaccacatcc ttttcatgat tttttgcctt   1980
gttatctcat atataaacat gcattgcacc taataaggtg ggcgccttac tcctcttgct   2040
ttcagaaatg ccctgctcag tccatggagc aaccattctt tcattccttt actttcttaa   2100
taaacttgct ttcacttta                                                2119

SEQ ID NO: 12          moltype = DNA   length = 584
FEATURE                Location/Qualifiers
source                 1..584
                       mol_type = genomic DNA
                       organism = Homo sapiens
SEQUENCE: 12
actgaaccag tatcattaaa gcttgaagtg ttgaaataag tggcctggga ctggcttcca    60
cggtgataaa agattcatct ggtagcacca gagtaaaaga agtctcacta aacactggcc   120
gggcagctgc tgctcggtgt gagcatcccg gggatgcaag cgtggggag gcatcccttt    180
gtttcctgag tcctagaagc aggtccccga cgaggaacaa cgatgcctgg actcagcttc   240
agcctctgtt cttctaccgt tcagaagcca ccctccggca aggtgacccc ggctgctgga   300
tggggcaagc ccaggaattc tcggcttctg acacatgacg cattcatctt ctccgacagt   360
gttcccatgc acaacttgtg gttcgggttg gaaatgcaaa gtggaaaaat gcatagcagt   420
atccctcct ccaaggcctc agtctctgtg ctcatattca ctgagactag tgaccccga    480
cttcccactc gccggcccct cctcctcccc ttccaacata atatgctgtt tacttattta   540
ttgtgttcat tttccgtctc acccaaatct attctagaaa aggt                    584

SEQ ID NO: 13          moltype = DNA   length = 1185
FEATURE                Location/Qualifiers
```

-continued

```
source                   1..1185
                         mol_type = genomic DNA
                         organism = Homo sapiens
SEQUENCE: 13
gtggaggcac tgggccacct cagagggcca gtgtcttgct gagggggccgg agcagtcctg   60
tgcctgcagc ctccggagcc atgggaacag ggctgcgaag tcagtccttg cgagagcccc  120
gaccctccta tggaaagctg caggagccct gggggaggcc ccaggagggc caactccgca  180
gggcgctaag cctcagacag gggcaagaga agtccaggtc ccaggggcctc gagagaggca  240
cagaaagggcc agatgccact gcccaggagc gggtgccggg gagcctgggg gacacagagc  300
agctgatcca agcccagcga agaggcagcc ggtggtggct gaggcggtac caacaggtaa  360
gaagaaggtg ggagagcttt gtcgccatct tccccagcgt gactctgagt cagccggcct  420
ccccgtagcc cacactgggc accatcagct aaagatgctg gaagccatcg tggccccctt  480
gctgtgcctg gaccagccca ccgtgtctgc tgacctacct cttcacagct ctctggactt  540
tggctgggtg gccctaggag gcttctgcca ccagctcact ggagtcgcca cgtggctgcc  600
actcttagct ctggccccttc cactccagca ctagctctct ttgaagatcc cagcagggtc  660
aaaaagaagg gggctcagct gtctgccctc tgggcttggg tagggggcctt ggactatgat  720
tctatgaagg tttagaagaa gcctgcccgg aatgggggct gtggacgctc ctgccccaca  780
cgaccagctg tcaacttcca ggacggagct tgatgaagcc agacccatgg ccgagaggct  840
cacggacgtt gcctggtcac tgggccatga cccaactgcc cttcttgtca gttgctgatg  900
gtgggccagg gcgcaggtct ccctcccaga tggtgagccc tctgggggcaa ggaccacagc  960
tgggtggccc tcctggctga gcactctgtg ctgaaaacct ttgaacctca cggtgtcctg 1020
atgaaggaag cagaggaagt cttcctccct gtgtgacaga ggggggaaact gaggcccaga 1080
gtgggggaagg gatttcttgg ttttgacatc tccgacccca ccccacccca tccagtgtcc 1140
agcactggag tcgaacacag taataaagat gctgagaaaa agtca             1185

SEQ ID NO: 14           moltype = DNA  length = 1703
FEATURE                 Location/Qualifiers
source                  1..1703
                        mol_type = genomic DNA
                        organism = Homo sapiens
SEQUENCE: 14
ggcaaggccc gacctgaagc actggctcca gccttaggga aggttttggc cgtgggtttt   60
gttggcacgt accattttgc tgaaagacag agcaccttga ggacgttatc cctaaaatga  120
gagaggactg ggattgaaag gctgactaca gaaatggctg ctgcccagac gccctcaaaa  180
gccaaggatc ctcagagttg gttataaaat atttaagggc gagaaaagga tcgcaggagc  240
caggccctga gatgagcttg gagtccctgt ttcagcacat catcttcacc gagcatcagg  300
cggaggagag tcgccgtttg atgcgagaag taaggtcgga aataaccaga tgtcgtgaaa  360
aaattaagaa agcaacggag gagctgaatg aagagaaaat caagctggaa tctaaggttc  420
aacagttttt tgaaaaatcc ttcttcttac agcttttgaa agctcatgaa aatgctttag  480
aaaaacagta cagtgaaatt acaaaccata ggaatatgct tcttcaaacc tttgaggcta  540
taaagaaaca aatgatagag gaggaagaca aatttattaa ggaaattaca gactttaata  600
atgattatga ataacaaag aaaagagagc ttttgatgaa agaaaatgtc aagattgaaa  660
tatctgactt agaaaaccaa gcaaacatgt tgaaaagtga aatgaagtca atggaacatg  720
atagtagcca gttaaatgaa cttcaaaaac aaaagagtga attgatacaa gaattatta  780
ctctccaaag aaaacttaaa gttttttgaag atgaagagaa tgaatccatt tgtactacca  840
aatatctaga ggcagaaaaa ataaaaatca gtgaaaagcc tcaaaatgat acagaatgct  900
taagacttaa aaaagaatta gaactttata aggaagatga catggaaagt gtttatgaag  960
ctctccaaac agaaatagaa tttttggagt tgacattggc acagaaagat cttcaggaaa 1020
gcaaataact acagagaat tgatcagcca tctgagattt gatcagaata tctgagaatc 1080
aaatctttgt gatagatata tgaatggtac ccgttacaac ggatccttgt gggaaatatg 1140
gggtttaaaa tattcaaatt gttattatct agaaatgatg tgttagccct ttaagataat 1200
ttttgtcttg ttactcaaac tttaagagtt cttctgtggt ttgatttgt ttctaaaaga 1260
aggaaaagga gaagaagtag ataccgtgtt cccaggcttc ttatatgccc ctgaacctca 1320
agctgtccta ttctttctaa tctatataat atggtttgga tctgtgtcca tgcccaaatc 1380
tcatgttgaa ttgtgatccc cactgttgga ggtgggtcct gataggaggt gattgggtca 1440
tgggggtggg tttctcatga atagcttagc accattcttc ttggtactgt ccttgagttc 1500
tcctgagagc tagttgttta ctagtgtata gcacttctcc actttgctcc tgctgccacc 1560
gtatgagatg tctcactccc cctttgcctt cagtcatgat tggaaacttc ctgaggcctc 1620
cctagaagca gaagtcacta tgcttcctgt acagcctgca gaaccgtggg acaattaaac 1680
ttgtgttctt tgtaaattaa aaa                                     1703

SEQ ID NO: 15           moltype = DNA  length = 1940
FEATURE                 Location/Qualifiers
source                  1..1940
                        mol_type = genomic DNA
                        organism = Homo sapiens
SEQUENCE: 15
gttaatatta ctgcagcttg attacaaaag gcaatgatta attttaaagc agacaaaaaa   60
gatatgccct gattacaaag gaatgattaa ggcggaatgt cagacattgc acatttatag  120
cagtctttgc catcgtcaaa gtataagact ttgtaaaagt ttatatttag aatcacagtt  180
actttgtact ttataatatt cagtgtttgc gccttggata ccgggcaacc ctactccaac  240
tgggcctaag acctttgggg ttcacatgcc caggcaaac ctgcccccca caggatggtc  300
ccaatgagcc gccgtagttt aagttctcac aggcaaggcc cgacctgaag cactggctcc  360
agccttaggg aaggttttgg ccgtgggttt tgttggcacg taccattttg ctgaaagaca  420
gagcaccttg aggacgttat ccctaaaatg agagaggact gggattgaaa ggctgactac  480
agaaatggct gctgcccaga cgccctcaaa agccaaggat cctcagagtt ggttataaaa  540
tatttaaggg cgagaaaagg atcgcaggag ccaggccctg agatgagctt ggagtccctg  600
tttcagcaca tcatcttcac cgagcatcag gcggaggaga gtcgccgttt gatgcgagaa  660
gtaaggtcgg aaataaccag atgtcgtgaa aaaattaaga aagcaacgga ggagctgaat  720
```

```
gaagagaaaa tcaagctgga atctaagctt ttgaaagctc atgaaaatgc tttagaaaaa    780
cagtacagtg aaattacaaa ccataggaat atgcttcttc aaacctttga ggctataaag    840
aaacaaatga tagaggagga agacaaattt attaaggaaa ttacagactt taataatgat    900
tatgaaataa caaagaaaag agagcttttg atgaaagaaa atgtcaagat tgaaatatct    960
gacttagaaa accaagcaaa catgttgaaa agtgaaatga agtcaatgga acatgatagt    1020
agccagttaa atgaacttca aaaacaaaag agtgaattga tacaagaatt atttactctc    1080
caaagaaaac ttaaagtttt tgaagatgaa gagaatgaat ccatttgtac taccaaatat    1140
ctagaggcag aaaaaataaa aatcagtgaa aagcctcaaa atgatacaga atgcttaaga    1200
cttaaaaaag aattagaact ttataaggaa gatgacatgg aaagtgttta tgaagctctc    1260
caaacagaaa tagaattttt ggagttgaca ttggcacaga aagatcttca ggaaagcaaa    1320
taacttacag agaattgatc agccatctga gatttgatca gaatatctga gaatcaaatc    1380
tttgtgatag atatatgaat ggtacccgtt acaacggatc cttgtgggaa atatgggggtt    1440
taaaatattc aaattgttat tatctagaaa tgatgtgtta gcccctttaag ataattttttg    1500
tcttgttact caaactttaa gagttcttct gtggtttgat tttgtttcta aaagaaggaa    1560
aaggagaaga agtagatacc gtgttccag gcttcttata tgcccctgaa cctcaagctg    1620
tcctattctt tctaatctat ataatatggt ttggatctgt gtccatgccc aaatctcatg    1680
ttgaattgtg atccccactg ttggaggtgg gtcctgatag gaggtgattg ggtcatgggg    1740
gtgggtttct catgaatagc ttagcaccat tcttcttggt actgtccttg agttctcctg    1800
agagctagtt gtttactagt gtatagcact tctccacttt gctcctgctg ccaccgtatg    1860
agatgtctca ctccccttt gccttcagtc atgattggaa acttcctgag gcctccctag    1920
aagcagaagt cactatgctt                                                 1940
```

```
SEQ ID NO: 16          moltype = DNA  length = 1420
FEATURE                Location/Qualifiers
source                 1..1420
                       mol_type = genomic DNA
                       organism = Homo sapiens
SEQUENCE: 16
aatattactg cagcttgatt acaaaaggca atgattaatt ttaaagcaga caaaaaagat    60
atgccctgat tacaaaggaa tgattaaggc ggaatgtcag acattgcaca tttatagcag    120
tctttgccat cgtcaaagta taagactttg taaaagttta tatttagaat cacagttact    180
ttgtactta taatattcag tgtttgcgcc ttggataccg ggcaacccta ctccaactgg    240
gcctaagacc tttgggggttc acatgcccag ggcaaacctg cccccacag gatggtccca    300
atgagccgcc gtagtttaag ttctcacagg caaggcccga cctgaagcac tggctccagc    360
cttagggaag gtttttggccg tgggtttttgt tggcacgtac cattttgctg aaagacagag    420
caccttgagg acgttatccc taaaatgaga gaggactggg attgaaaggc tgactacaga    480
aatggctgct gcccagacgc cctcaaaagc caaggatcct cagagttggt tataaaatat    540
ttaagggcga gaaaaggatc gcaggagcca ggccctgaga tgagcttgga gtccctgttt    600
cagcacatca tcttcaccga gcatcaggcg gaggagagtc gccgtttgat gcgagaagta    660
aggtcggaaa taaccagatg tcgtgaaaaa attaagaaag caacggagga gctgaatgaa    720
gagaaaatca agctggaatc taaggttcaa cagtttttg aaaaatcctt cttcttacag    780
cttttgaaag ctcatgaaaa tgctttagaa aaacagtaca gtgaaattac aaaccatagg    840
aatatgcttc ttcaaaacctt tgaggctata agaaacaaa tgatagagga ggaagacaaa    900
tttattaagg aaattacaga ctttaataat gattatgaaa taacaaagaa aagagagctt    960
ttgatgaaag aaaatgtcaa gattgaaata tctgacttag aaaaccaagc aaacatgttg    1020
aaaagtgaaa tgaagtcaat ggaacatgat agtagccagt taaatgaact tcaaaaacaa    1080
aagagtgaat tgatacaaga attatttact ctccaaagaa aacttaaagt ttttgaagat    1140
gaagagaatg aatccatttg tactaccaaa tatctagagg cagaaaaaat aaaaatcagt    1200
gaaaagcctc aaaatgatac agaatgctta aggtaactaa aagggtgagt ggtcaccacc    1260
taattctgat aggcatgaga agtcatacag aacctgtagt ccatttgaag tgaagagatg    1320
gatgagcacg tgttgatgga atggtgggaa tatctctacc attttatttg aaaaataaat    1380
ttattaaaaa gaaggcttat gtacatttca atagcagcat                          1420
```

```
SEQ ID NO: 17          moltype = DNA  length = 1617
FEATURE                Location/Qualifiers
source                 1..1617
                       mol_type = genomic DNA
                       organism = Homo sapiens
SEQUENCE: 17
gaaaaacaaa cccagggagg gacggaggcc tgagtcaggg gttccgccag ggaaaaaggc    60
agaccttgaa actgccctct tagggcgtga gggagaaaag cccggatcct cagagttggt    120
tataaaatat ttaagggcga gaaaaggatc gcaggagcca ggccctgaga tgagcttgga    180
gtccctgttt cagcacatca tcttcaccga gcatcaggcg gaggagagtc gccgtttgat    240
gcgagaagta aggtcggaaa taaccagatg tcgtgaaaaa attaagaaag caacggagga    300
gctgaatgaa gagaaaatca agctggaatc taaggttcaa cagtttttg aaaaatcctt    360
cttcttacag cttttgaaag ctcatgaaaa tgctttagaa aaacagtaca gtgaaattac    420
aaaccatagg aatatgcttc ttcaaaacctt tgaggctata agaaacaaa tgatagagga    480
ggaagacaaa tttattaagg aaattacaga ctttaataat gattatgaaa taacaaagaa    540
aagagagctt ttgatgaaag aaaatgtcaa gattgaaata tctgacttag aaaaccaagc    600
aaacatgttg aaaagtgaaa tgaagtcaat ggaacatgat agtagccagt taaatgaact    660
tcaaaaacaa aagagtgaat tgatacaaga attatttact ctccaaagaa aacttaaagt    720
ttttgaagat gaagagaatg aatccatttg tactaccaaa tatctagagg cagaaaaaat    780
aaaaatcagt gaaaagcctc aaaatgatac agaatgctta agacttaaaa aagaattaga    840
acttataag gaagatgaca tggaaagtgt ttatgaagct ctccaaacag aaatagaatt    900
tttggagttg acattggcac agaaagatct tcaggaaagc aaataactta cagagaattg    960
atcagccatc tgagatttga tcagaatatc tgagaatcaa atctttgtga tagatatatg    1020
aatggtaccc gttacaacgg atccttgtgg gaaatatggg gtttaaaata ttcaaattgt    1080
tattatctag aaatgatgtg ttagcccttt aagataattt ttgtcttgtt actcaaactt    1140
taagagttct tctgtggttt gattttgttt ctaaaagaag gaaaaggaga agaagtagat    1200
```

-continued

```
accgtgttcc caggcttctt atatgcccct gaacctcaag ctgtcctatt cttcctaatc  1260
tatataatat ggtttggatc tgtgtccatg cccaaatctc atgttgaatt gtgatcccca  1320
ctgttggagg tgggtcctga taggaggtga ttgggtcatg ggggtgggtt tctcatgaat  1380
agcttagcac cattcttctt ggtactgtcc ttgagttctc ctgagagcta gttgtttact  1440
agtgtatagc acttctccac tttgctcctg ctgccaccgt atgagatgtc tcactccccc  1500
tttgccttca gtcatgattg gaaacttcct gaggcctccc tagaagcaga agtcactatg  1560
cttcctgtac agcctgcaga accgtgggac aattaaactt gtgttctttg taaaatta    1617

SEQ ID NO: 18            moltype = DNA  length = 660
FEATURE                  Location/Qualifiers
source                   1..660
                         mol_type = genomic DNA
                         organism = Homo sapiens
SEQUENCE: 18
gattaggcct ggtttgcgct ggagagtggt cttggttgtg agggtcataa gatgggaact  60
ctcccggcac gtagacatat cccgccgtgg gtgaaagttc ccgaagacct gaaagatcca  120
gaggtgttcc aggtccagac gcggctgctg aaagccattt tcggcccgga cggatctcga  180
atcccttaca tcgagcaggt gagcaaggcc atgctcgagc tgaaggctct ggagtcttca  240
gacctcaccg aggtcgtggt ttacggctcc tatttgtaca agctccggac caagtggatg  300
ctccagtcca tggctgagtg gcaccgccag cgccaggagc gagggatgct caaacttgcc  360
gaagccatga atgccctcga actaggccct tggatgaagt gaaccagttt ccagccaatg  420
caatgaagcc gggttgcaga gattaggttg tggccagagc tagagtgatt ccttaagctt  480
gttttaaaat ctgctccagc ctaaagagtt aagggaaaac catttgttcc cttaaagagt  540
taagggaaaa cccttggctc tgagtcttgt tgtgaatatt tctttgatga ttgttaataa  600
aaagtgtttt ttcttttttc ccatttttaa aaataacaat aaagtttttaa ataagttgat  660

SEQ ID NO: 19            moltype = DNA  length = 3178
FEATURE                  Location/Qualifiers
source                   1..3178
                         mol_type = genomic DNA
                         organism = Homo sapiens
SEQUENCE: 19
atggccacct actgcgacga cctgggcccc tcctcggccc cgcccggcca ggcccaggcc  60
accgcgcacc ccccgggcta tgagccaggg gatctgggcg cggtgggcgg gggccccctc  120
ctgtgggtga acgcgccagc gctcagcccc aagtcctacg cttcgggtcc cgggcctggg  180
ccgccctacg cggccccgag ctacggggct cccggcccgc tcctcggcgc cccggcggc   240
ctggcgggcg ccgacctcgc ctggctgagc ctctccggcc agcaggagct gctgaggctg  300
gtgcggccgc cctactccta ctcggcgctc atcgccatgg ccatccagag cgcgccgctg  360
cggaagctga cgctcagcca gatctaccag tacgtggctg gtaacttccc tttctacaag  420
cgcagcaagc cgggctggca gaactccatc cgccacaacc tgtcgctcaa cgactcgttc  480
aagaaggtgc ccgcgacga ggacgaccca ggtaaaggca attactggac cctggacccc  540
aactgcgaga agatgtttga caacgggaac ttccgaagga agaggaagag gagagctgaa  600
gccagcgcag ccgtgcgctc gggagccagg agcgtgggag gggccgaggc gccagcgctg  660
gagcccccga gcgcggcttg cctggacctg caggcctcgc cctctccatc cgcacccgag  720
gccgccacct gcttctccgg tttcgcttct gctatgagcg ctctggctgg cggccttggc  780
accttccccg ggggcctggc gggcgacttt tctttcggga ggcggccacc gacagtcgcc  840
acccacgctc cccagaccct taaccctcc cctggcttcg ccctggcca ccagaccgcg  900
gccgccggct tccgcctcag tcacctcctc tacagccggg aagggaccga agtttgaagg  960
gaggctggag gctagccggg tgcgggtcca gaggtgctga gctcaggcct ccggtttccc  1020
ctggtgacag ccccacgtgt tggcgttgaa ggccttggtg ccctgggagg aagcgcagag  1080
ccggggcgg ctcggccagc agggagctgg gctgagcggc tcttgggctt tggggtgggt  1140
ggcccttctg ctgtgcaccc ctcacccagg cgaccttcgg aacctccctg ctctgcctct  1200
aagtccagcc gccctgggcg tctagaacct gtgctctcga gggatttgcc ttgaaggggc  1260
ggcgggtcgg ccctcagctc cagcgttttc caaggaggct ggctgactcc aaagagcctt  1320
agagcagatg ggaagaaggt gggctgccag agcggcccag gtggtggggg cctttccac   1380
ctccacccag cttggcccac ctggctcagg gccttccctt ctgcttcagg gaagctgccg  1440
caggggctgg gggacagagc tcaggagcag ctgcagtggg ctccaggtgg gccaggagcc  1500
tgcagtgagg ggatctgaga cagttggcat tgggtcctgt gtaaggaagg tcttgctaat  1560
ggttggaact gctggtggtg ggagggagaa gcactgcgtg ggcagaaagc gcccttggga  1620
taccagctcc cttccctgtc actcagccct ggtccttgat gaccccctc taggacaagg  1680
caactcccca gggccccgcc accactgacc acaggagcgg tgcccagcac ccaggagttc  1740
cccaagggtc caggtttgtg ccacccacac ccacactcac acccacactc acacccacac  1800
tcacacccac acccacaccc acaccacac tcacactcac actcacaccc acactcacac  1860
ccacactcac acccacaccc acacccacac tcacaccac acccacactc acacactcat  1920
acacccacac acactcacac ccacacacac ccacactcat actcacactc acacccacac  1980
tcacaccaca cccacactca cactgacacc cacactcaca cccacactca cactgacacc  2040
cacactcaca cccacactca tactcacact cacacccaca ctcacactca cacccacact  2100
cacacacac tcacacccac acacacccac actcatactc acaccacac ccacacactcat  2160
actcacacac ccacacccac acccacaccc acacccacac ccacacccac actcacacag  2220
gctcatggaa ggccacactt gttttggtct ctttcccctc caaacccaca gtttgagcca  2280
aagctgtgcg tgtgttcaga gctcctgaac agcagcctcc tgtgtaaatt gaaccctgcc  2340
ccacccagtt ccttcttagg gatggtatct ttgtgaagga caaggagccc ccagtcactg  2400
ggaagaggaa ttttttggcc tctgtactcc ttagaggacc taagtgcccc agtcagatgc  2460
cctgagtctt tgtggcatct gggactccct ggagatggag acgttgggga cccaccttgt  2520
cccaccttgt tgttgatggg ggtacctatc ttccctgcat tttgggggag ggtgggaggg  2580
gtccttccca ggaagagagt ggagacaggt tactgttact ttggagtggg acaggctggt  2640
ttagcaatcc taagccccag ccacgcaggt attcctgatc tgcctgcagg gcccctcact  2700
gcagctgcca ccagtgctgg aaatgagagc agggctcctg actgtcccta gagctgactc  2760
atcatggccc tgctgaagag tgaggtgtgt gtgtgtgtgt gcgtgtgtgc gtaagacaga  2820
```

-continued

```
gagggaggga gaaggaagga ggcgggggaa catggagaga aggagccagg agttgggata   2880
aacctggccc tggtcatatg tttcatcagc agtggctcct aactccacgt gccatctctg   2940
ctgctgccct ccacaagcag gtgagcagag tgccagttgt gttgaaggtg atgatgtcgc   3000
ctaactaaac tcacaaccaa cccgcaatct ctcttggggg gacactcccc ataagcaata   3060
caattaaaga agaccaggaa aggaaaataa attccttagc ttatacattt aaaaagtatc   3120
ccttgaacct attttaatag aatgaaatgc taaaaataaa gaccaatata acatacat     3178

SEQ ID NO: 20            moltype = DNA   length = 1319
FEATURE                  Location/Qualifiers
source                   1..1319
                         mol_type = genomic DNA
                         organism = Homo sapiens
SEQUENCE: 20
ctccacaccg ccttgcaagc tgagggagcc ggctccggcc tctgccagcc caggaagggg    60
ctcccacagt gcagcggcgg gctgaaggac tcctcaagtg ccaccaaagt gggagcccag   120
gcagaggagg cgccgagagc gagcgagggc tgcctgccag cacgctgtca cgtctcagca   180
atagactgct cttgaggctg gagtgcaatg ttgttatcat agctcactgc aacctggaac   240
ccctagtctc aagagatcct ccagcctcag cctccctggg atggctattt ttgttacttc   300
tgaattctac tacaaaagag tgctgcaata aaaatctttg aacaagttct aatgccgttc   360
aactggaatt gaagttttca atcgttggat atgtcaaaat ttaatcagat tgtatattgc   420
tcaattactt tcaaattatg tacaccaagt cattcttgct ctggcaaaat aagaatattt   480
tcattaatat atcattcaac ttgaaattgc ccagcttttc cttctcattt cccccagtc    540
aaatgagttg aattaatact gtctaaaaat atatattcat ttgcttacct gttagtattt   600
gttccatgta ttaagaagct ttgctagtat atgaaaatat atgtattacc atgtcttgtg   660
aattagtact tttatcattt tgaaatgttt gtttttcattt ctgctgaccg ttctaacctg   720
ggtatctatt ttgactggtt tttaatgtaa ctactaacat cttttttatgt tcagcacttt   780
ttcacaattt tactttcaat gtctttattt ttaaaatgta tcttctgtag acagtgtaca   840
ggtggtcttg ttttattgta aatcaagtga caatctctat ttcataattg acatatttaa   900
tccatatata tttaatttaa ttgttgttat tttgagactt aatatccagt tttactattt   960
tggcccattt atttttggtt tattttagat gtcttgcctt atcttagatt gattgatatt  1020
tttagtattt aattacattt cttttataaa tgtaatttct tgaatatttg tttttatttt  1080
agcaattgct ctgggaatat aaaaatcatc tttaaaatct atttagagtt aatggtacta  1140
ctttatgcag taggtaaaaa catttcacta gcacaatttc atttgcaggc acctaacctt  1200
ctgtgatagt attgtcttat attgttatat ttatgagata caatcactac agtaaaatac  1260
tattttctat tcattgtgcc atcttataaa taaacgatg aataaacaga tattttttga  1319

SEQ ID NO: 21            moltype = DNA   length = 670
FEATURE                  Location/Qualifiers
source                   1..670
                         mol_type = genomic DNA
                         organism = Homo sapiens
SEQUENCE: 21
ctccacaccg ccttgcaagc tgagggagcc ggctccggcc tctgccagcc caggaagggg    60
ctcccacagt gcagcggcgg gctgaaggac tcctcaagtg ccaccaaagt gggagcccag   120
gcagaggagg cgccgagagc gagcgagggc tgcctgccag cacgctgtca cgtctcagca   180
atagactgct cttgaggctg gagtgcaatg ttgttatcat agctcactgc aacctggaac   240
ccctagtctc aagagatcct ccagcctcag cctccctgtt ccaggataca tgtgcaggat   300
gtgcaagttt gctacatggg taaatatgtg ccatggcagt ttgctgcatc tattaaccca   360
ttacctaggt attaagcccg atacaagagt tatggaaaag ctgcactctt ctacttccaa   420
agtttaactt cttcacagaa gtcagtttca gagttgagaa aagcaaatac ttgctacata   480
ttttgaggaa caataagtat tgaagttgca aacaggttct atggatattt gtcaacagaa   540
gatagctgat cacaaatgcg cagagaggta gaaaaatgac acaatgacca ccctaccctc   600
tgagtcagca aattgtttttc tcagtacatt tctactctgg tccttgttta ataaaacctc   660
tttctcctta                                                          670

SEQ ID NO: 22            moltype = DNA   length = 540
FEATURE                  Location/Qualifiers
source                   1..540
                         mol_type = genomic DNA
                         organism = Homo sapiens
SEQUENCE: 22
ctccacaccg ccttgcaagc tgagggagcc ggctccggcc tctgccagcc caggaagggg    60
ctcccacagt gcagcggcgg gctgaaggac tcctcaagtg ccaccaaagt gggagcccag   120
gcagaggagg cgccgagagc gagcgagggc tgcctgtcga cgtctcagca   180
atagactgct cttgaggctg gagtgcaatg ttgttatcat agctcactgc aacctggaac   240
ccctagtctc aagagatcct ccagcctcag cctccctgtt ccaggataca tgtgcaggat   300
gtgcaagttt gctacatggg taaatatgtg ccatggcagt ttgctgcatc tattaaccca   360
ttacctaggt attaagcccg gaaataagaa tggcagaaat gtgaagagtt attgtgtggg   420
gaagtggcct ctacatagaa atgttttttcc actgaatgtt cctgttgtgc tgatgaacaa   480
aggagttcat cacaggccaa aaactaagat agatagataa ataaataaat aaataaataa   540

SEQ ID NO: 23            moltype = DNA   length = 195
FEATURE                  Location/Qualifiers
source                   1..195
                         mol_type = genomic DNA
                         organism = Homo sapiens
SEQUENCE: 23
ctgccaccca ggctagagtg caatggcatg accatagctc actgctacct caaacacctg    60
ggctcaagtg atcccctgc ctcagcctct caattccagg atacatgtgc aggatgtgca   120
```

```
agtttgctac atgggtaaat atgtgccatg gcagtttgct gcatctatta acccattacc     180
taggtattaa gcccg                                                       195

SEQ ID NO: 24          moltype = DNA   length = 616
FEATURE                Location/Qualifiers
source                 1..616
                       mol_type = genomic DNA
                       organism = Homo sapiens
SEQUENCE: 24
ggaacatctc accaatttta aatcagtttt tcaagtggta cctgagattc agcacttcta     60
aaaagctcca aggtgatgaa ggtgctgcta gttggaggcc atactttgag ttgccagatg     120
ctaaaaattc aacagatggg gtatgtaagc agatagtgta gcatattgaa aacaactctc     180
agtttgaatc agaagcctgg gtctgtgata ttatgacact aactagctta atattttgtg     240
gattattgtg catgaaatat atccatttaa atatcatact ttcaatttaa attatgggtt     300
tcaactttgc caggcaaata taatcaacaa tatattcaat agtatgccac agctaaagac     360
acaaatgaaa acaatgatct cagacttttg atccaggtgc caagttagaa aaagaagtta     420
aaacagtgta gtttatttct gttcaatgtc ctgtataggt ggaaactaat ttcagggtta     480
atttttggtt aaacaactag cttggaaatt tataattatt tgggattgag gaccaaacaa     540
ggtgaggcac gataaagaaa ttagaagggg atcgctatga aaatcaagat gaataaaacg     600
aagggagtgt ttacgg                                                      616

SEQ ID NO: 25          moltype = DNA   length = 2716
FEATURE                Location/Qualifiers
source                 1..2716
                       mol_type = genomic DNA
                       organism = Homo sapiens
SEQUENCE: 25
gtgagggaat tccgtgtgtg ggaaccgtgg ggaggagctg ccaggattca ggagtttcct     60
gggtgaggcg tggccacaac ggacactcct gctttgtact agaaggaaga agtatggagt     120
taaagactgc agcgtgaact gaggagtccc ggacaggccg cttgctgcag aggatccagt     180
ccagatccca ggagagcccc tctgcccctt cggacctcgt ctcccatcta caaaacgtga     240
agattggccc agttagcgtg tctctacaaa aaggtgcata taccactgcc ccgctgcagg     300
ctgatctgag aaagcctctg gcccagggca gataccgcca tggccttcct gatgcacctg     360
ctggtctgcg tcttcggaat gggctcctgg gtgaccatca atgggctctg ggtagagctg     420
cccctgctgg tgatggagct gcccgagggc tggtacctgc cctcctacct cacggtggtc     480
atccagctgg ccaacatcgg gcccctcctg gtcaccctgc tccatcactt ccggcccagc     540
tgcctttccg aagtgcccat catcttcacc ctgctgggcg tgggaaccgt cacctgcatc     600
atctttgcct tcctctggaa tatgacctcc tgggtgctgg acggcaccca cagcatcgcc     660
ttcttggtcc tcaccttctt cctggccctg gtggactgca cctcttcagt gaccttcctg     720
ccgttcatga gccggctgcc cacctactac ctcaccacct tctttgtggg tgaaggactc     780
agcggcctct tgcccgccct ggtggctctt gcccagggct ccggtctcac tacctgcgtc     840
aatgtcactg agatatcaga cagcgtacca agccctgtac ccacgaggga gactgacatc     900
gcacaggagg ttcccagagc tttggtgtcc gccctcccgg gaatggaagc acccttgtcc     960
cacctggaga gccgctacct tcccgcccac ttctcacccc tggtcttctt cctcctccta     1020
tccatcatga tggcctgctg cctcgtgcgg ttctttgtcc tccagcgtca acccaggtgc     1080
tgggaggctt ccgtggaaga cctcctcaat gaccaggtca ccctccactc catccggccg     1140
cgggaagaga atgacttggg ccctgcaggc acggtggaca gcagccaggg ccaggggtat     1200
ctagaggaga aagcagcccc ctgctgcccg gcgcacctgg ccttcatcta taccctggtg     1260
gccttcgtca acgcgctcac caacggcatg ctgccctctg tgcagaccta ctcctgcctg     1320
tcctatgggc cagttgccta ccacctggct gccacccta gcattgtggc caaccctctt     1380
gcctcgttgg tctccatgtt cctgcctaac aggtctctgc tgttcctggg ggtcctctcc     1440
gtgcttggga cctgctttgg gggctacaac atggccatgg cggtgatgag ccctgcccc     1500
ctcttgcagg gccactgggg tggggaagtc ctcattgtgg cctcgtgggt gctttttcagc     1560
ggctgcctca gttacgtcaa ggtgatgctg ggcgtggtcc tgcgcgacct cagccgcagc     1620
gccctcttgt ggtgcggggc ggcggtgcag ctgggcctgc tgctcggagc gctgctcatg     1680
ttccctctgg tcaacgtgct gcggctcttc tcgtccgcgg acttctgcaa tctgcactgt     1740
ccagcctagg caggccgccg accccgcccc catcgctcac ggacggaact ggggtccaga     1800
gaggccaggt cacagagcaa ggggcaggaa cagagagaca gagcctgagt aattgaatca     1860
tgaacgcaag tgcccactgg ggactgtggg gaagatggca cctggaaatg caaggtgcgg     1920
ctctatcccc aactctgtgt cacactacct gtgacgacca gctcagatct ccttttgcctt     1980
gactctcaag agaggactga tttgcagcat ctagctggag gcaggcccaa gggtgttaga     2040
agggaaacag ctgggacagc cggctgtccc ttcaggctgt gtgaccttgg gaaagtcatt     2100
tggcttctct gtgcctgttt cttcatgcat gcagtgggga ttccagtaag taccaactac     2160
ctcacaggca tggcacggag gcaaaaggaa aaagcagccc gcatcaagca agccctcctg     2220
ggccacctgc tgatctgaca gtccatcgta gtaacaagag tggcagtctg cacaacctag     2280
aagtggccag aagggttgag acacgcccct gccctctctc ctttgcccct cagtctcaca     2340
gaggggcttc tacaagacaa gcagataacg atagaatctt gggcatcttg gctttcggat     2400
tctcagtgtg gagggacgta gtaccccaca cacccttcc tgtcatcctt cctggcccat     2460
aaagcccact agttggagag taagtaccct cctggaagcc gggagagatg atttgctggt     2520
ggggctgggg aaggcccatc cctgagcctc tgaaagtgaa ctccccgacc aggttgggga     2580
ccagacatgc agagcccctg gaagtattct ctcaaatgga ggcaacagag gtgattgtta     2640
ttttgtttta gtttctgttt ttcatttttt taaataaagg cattccctgc ttttaaaaaa     2700
aaaaaaaaaa aaaaaa                                                      2716

SEQ ID NO: 26          moltype = DNA   length = 2624
FEATURE                Location/Qualifiers
source                 1..2624
                       mol_type = genomic DNA
                       organism = Homo sapiens
```

```
SEQUENCE: 26
atgcagagcg gctggggaac tggaccagca gaaggaagaa gtatggagtt aaagactgca    60
gcgtgaactg aggagtcccg gacaggccgc ttgctgcaga ggatccagtc cagatcccag   120
gagagcccct ctgccccttc ggacctcgtc tcccatctac aaaacgtgaa gattggccca   180
gttacgtgt ctctacaaaa aggtgcatat accactgccc cgctgcaggc tgatctgaga    240
aagcctctgg cccagggcag ataccgccat ggccttcctg atgcacctgc tggtctgcgt   300
cttcggaatg ggctcctggg tgaccatcaa tgggctctgg gtagagctgc ccctgctggt   360
gatggagctg cccgagggct ggtacctgcc ctcctacctc acggtggtca tccagctggc   420
caacatcggg cccctcctgg tcaccctgct ccatcacttc cggcccagct gcctttccga   480
agtgcccatc atcttcaccc tgctgggcgt gggaaccgtc acctgcatca tctttgcctt   540
cctctggaat atgacctcct gggtgctgga cggccaccac agcatcgcct tcttggtcct   600
caccttcttc ctggccctgg tggactgcac ctcttcagtg accttcctgc cgttcatgag   660
ccggctgccc acctactacc tcaccacctt ctttgtgggt gaaggactca gcggcctctt   720
gcccgccctg gtggctcttg cccagggctc cggtctcact acctgcgtca atgtcactga   780
gatatcagac agcgtaccaa gccctgtacc cacgagggag actgacatcg cacagggagt   840
tcccagagct ttggtgtccg ccctccccgg aatggaagca cccttgtccc acctggagag   900
ccgctacctt cccgcccact tctcaccct ggtcttcttc ctcctcctat ccatcatgat    960
ggcctgctgc ctcgtggcgt tctttgtcct ccagcgtcaa cccaggtgct gggaggcttc   1020
cgtggaagac ctcctcaatg accaggtcac cctccactcc atccggccgc gggaagagaa   1080
tgacttgggc cctgcaggca cggtggacag cagccagggc caggggtatc tagaggagaa   1140
agcagccccc tgctgcccgg cgcacctggc cttcatctat accctggtgg ccttcgtcaa   1200
cgcgctcacc aacggcatgc tgccctctgt gcagacctac tcctgcctgt cctatgggcc   1260
agttgcctac cacctggctg ccaccctcag cattgtggcc aaccctcttg cctcgttggt   1320
ctccatgttc ctgcctaaca ggtctctgct gttcctgggg gtcctctccg tgcttgggac   1380
ctgctttggg ggctacaaca tggccatggc ggtgatgagc ccctgccccc tcttgcaggg   1440
ccactggggt ggggaagtcc tcattgtggc ctcgtggtca cttttcagcg gctgcctcag   1500
ttacgtcaag gtgatgctgg gcgtggtcct gcgcgacctc agccgcagcg ccctcttgtg   1560
gtgcggggcg gcggtgcagc tgggctcgct gctcggagcg ctgctcatgt tccctctggt   1620
caacgtgctg cggctcttct cgtccgcgga cttctgcaat ctgcactgtc cagcctaggc   1680
aggccgccga ccccgccccc atcgctcacg gacggaacct gggtccagag aggccaggtc   1740
acagagcaag gggcaggaac agagagacag agcctgagta attgaatcat gaacgcaagt   1800
gcccactggg gactgtgggg aagatggcac ctggaaatgc aaggtgcggc tctatcccca   1860
actctgtgtc acactacctg tgacgaccag ctcagatctc ctttgctttg actctcaaga   1920
gaggactgat ttgcagcatc tagctggagg caggcccaag ggtgttagaa gggaaacagc   1980
tgggacagcc ggctgtccct tcaggctgtg tgaccttgag aaagtcattt ggcttctctg   2040
tgcctgtttc ttcatgcatg cagtggggat tccagtaagt accaactacc tcacaggcat   2100
ggcacggagg caaaaggaaa aagcagcccg catcaagcaa gccctcctgg gccacctgct   2160
gatctgacag tccatcgtag taacaagagt ggcagtctgc acaacctaga agtggccaga   2220
agggttgaga cacgcccctg ccctctctcc tttgcccctc agtctcacag aggggcttct   2280
acaagacaag cagataacga tagaatcttg ggcatcttgg cttttcggatt ctcagtgtgg   2340
agggacgtag taccccacac accccttcct gtcatccttc ctggcccata aagcccacta   2400
gttggagagt aagtaccctc ctggaagccg ggagagatga tttgctggtg gggctgggga   2460
aggcccatcc ctgagcctct gaaagtgaac tccccgaccca ggttggggac cagacatgca   2520
gagcccctgg aagtattctc tcaaatggag gcaacagagg tgattgttat tttgttttag   2580
tttctgtttt tcatttttttt aaataaaggc attccctgct ttta                   2624
```

```
SEQ ID NO: 27        moltype = DNA  length = 3133
FEATURE              Location/Qualifiers
source               1..3133
                     mol_type = genomic DNA
                     organism = Homo sapiens
SEQUENCE: 27
atgcagagcg gctggggaac tggaccagca gaaggaagaa gtatggagtt aaagactgca    60
gcgtgaactg aggagtcccg gacaggccgc ttgctgcaga ggatccagtc cagatcccag   120
gagagcccct ctgccccttc ggacctcgtc tcccatctac aaaacgtgaa gattggccca   180
gttagcgtgt ctctacaaaa aggtgcatat accactgaag ctgctttgtt tgcttttgtg   240
tgtcggattg aacttttctt tcatgaatca cggttaggaa aggcttctct tgtttttctgc   300
taataaaaag acagcttggg ccaggcgtgg tggctcacac tgtaatccca gcactttggg   360
aggccgaggc aggcggatca cctgaggcca ggagttcgag accagcctga ccaacgtggg   420
gaaaccctgt ttccactaaa aatacaaaat tagctggcat ggtggcatgc acctgtaatc   480
ccagctattt gggaaactga ggcaggagaa tcacttgagc ccaggaggca gagggtcact   540
gagccgagat catcccattg cactccagcc tggactaaaa gagtgaaact atgtctcaaa   600
ggaaaaaaaa aaaagccagc ttgttcacag gaaggggagt aataagagaa aactctgggc   660
cccaggtccc agcatcttgc taggtggtga agctggaatt actcacctgg tgtccttctc   720
tgccagcccc gctgcaggct gatctgagaa agcctctggc ccagggcaga taccgccatg   780
gccttcctga tgcacctgct ggtctgcgtt tcggaatgg gctcctgggt gaccatcaat   840
gggctctggg tagagctgcc cctgctggtg atggagctgc ccgagggctg gtacctgccc   900
tcctacctca cggtggtcat ccagctggcc aacatcgggc ccctcctggt caccctgctc   960
catcacttcc ggcccagctg cctttccgaa gtgcccatca tctttgcctt ctctggaata   1020
tgacctcctg ggtgctggac ggccaccaca gcatcgcctt cttggtcctc accttcttcc   1080
tggccctggt ggactgcacc tcttcagtga ccttcctgcc gttcatgagc cggctgccca   1140
cctactacct caccacct ttgtgggt aaggactcag cggcctcttg cccgccctg    1200
tggctcttgc ccagggctcc ggtctcacta cctgcgtcaa tgtcactgag atatcagaca   1260
gcgtaccaag ccctgtaccc acgagggaga ctgacatcgc acagggagtt cccagagctt   1320
tggtgtccgc cctccccgga atggaagcac ccttgtccca cctggagagc cgctaccttc   1380
ccgcccactt ctcacccctg gtcttcttcc tcctcctatc catcatgatg gcctgctgcc   1440
tcgtggcgtt ctttgtcctc cagcgtcaac ccaggtgctg ggaggcttcc gtggaagacc   1500
tcctcaatga ccaggtcacc ctccactcca tccggccgcg ggaagagaat gacttgggcc   1560
tgcaggcac ggtggacagc                                              1620
```

-continued

```
agccagggcc aggggtatct agaggagaaa gcagcccct gctgcccggc gcacctggcc  1680
ttcatctata ccctggtggc cttcgtcaac gcgctcacca acggcatgct gccctctgtg  1740
cagacctact cctgcctgtc ctatgggcca gttgcctacc acctggctgc caccctcagc  1800
attgtggcca accctcttgc ctcgttggtc tccatgttcc tgcctaacag gtctctgctg  1860
ttcctggggg tcctctccgt gcttgggacc tgctttgggg gctacaacat ggccatggcg  1920
gtgatgagcc cctgcccct cttgcagggc cactggggtg gggaagtcct cattgtggcc  1980
tcgtgggtgc ttttcagcgg ctgcctcagt tacgtcaagg tgatgctggg cgtggtcctg  2040
cgcgacctca gccgcagcgc cctcttgtgg tgcggggcgg cggtgcagct gggctcgctg  2100
ctcggagcgc tgctcatgtt ccctctggtc aacgtgctgc ggctcttctc gtccgcggac  2160
ttctgcaatc tgcactgtcc agcctaggca ggccgccgac ccgcccca tcgctcacgg  2220
acggaactgg ggtccagaga ggccaggtca cagagcaagg ggcaggaaca gagagacaga  2280
gcctgagtaa ttgaatcatg aacgcaagtg cccactgggg actgtgggga agatggcacc  2340
tggaaatgca aggtgcggct ctatccccaa ctctgtgtca cactacctgt gacgaccagc  2400
tcagatctcc tttgctttga ctctcaagag aggactgatt tgcagcatct agctggaggc  2460
aggcccaagg gtgttagaag ggaaacagct gggacagccg gctgtccctt caggctgtgt  2520
gaccttggga aagtcatttg gcttctctgt gcctgtttct tcatgcatgc agtggggatt  2580
ccagtaagta ccaactacct cacaggcatg gcacggaggc aaaaggaaaa agcagcccgc  2640
atcaagcaag ccctcctggg ccacctgctg atctgacagt ccatcgtagt aacaagagtg  2700
gcagtctgca caacctagaa gtggccagaa gggttgagac acgcccctgc cctctctcct  2760
ttgcccctca gtctcacaga ggggcttcta caagacaagc agataacgat agaatcttgg  2820
gcatcttggc tttcggattc tcagtgtgga gggacgtagt accccacaca ccccttcctg  2880
tcatccttcc tggcccataa agcccactag ttggagagta agtaccctcc tggaagccgg  2940
gagagatgat ttgctggtgg ggctggggaa ggcccatccc tgagcctctg aaagtgaact  3000
ccccgaccag gttggggacc agacatgcag agccctgga agtattctct caaatggagg  3060
caacagaggt gattgttatt ttgtttag ttctgttttt cattttttta aataaaggca  3120
ttccctgctt tta                                                     3133
```

```
SEQ ID NO: 28          moltype = DNA  length = 1172
FEATURE                Location/Qualifiers
source                 1..1172
                       mol_type = genomic DNA
                       organism = Homo sapiens
SEQUENCE: 28
tggaaagcta cacgtgtgag cctagaggcg ggtcccggtt gcagacttgc catggcctcc  60
gaagcttctg tgcgtctagg ggtgcccct ggccgtctgt ggatccagag gcctggcatc  120
tacgaagatg aggaggggag aacctgggtg actgtggtcg tgcggttcaa tccctcgcgt  180
agggaatggg ccagggcctc ccagggcagc agatatgaac ccagcatcac agtgcacttg  240
tggcagatgg cagtgcatac ccgggagcta ctctcctccg gccagatgcc cttctcccag  300
ctgcccgccg tgtggcagct ctaccccggg aggaagtacc gagcagcgga ttccagtttc  360
tgggaaatag cagaccatgg ccagattgac tctatggagc agctggtcct aacatatcag  420
ccggagagga aagactgaca ctgggagtgg ctggccctgc tggccctgcc tcttctggcc  480
tggtgtctcc tcatgcccc tcagtgagga tcttcatgta cctgctcttc tgtttgcaca  540
cccagcatag cctccttgca ggcagaaggc agtagggccc ctgcacactc agtttctctc  600
gttttcctta gttatcagtc ctgtcctgtc ccactcaggt ctgtacttag ggcagctggc  660
ctggatgggc ttcactgggg ccctgtctgt gtgctgagcc agtttcccct gctggctgca  720
agctgtgggt tctttctcct ctgtgcccct catgctgatc ttctagatgc cactcccaaa  780
tccccttcat acccaccagg atgtgtgccc agccaggcct ccagcacccc cagtgcagct  840
cgtgattgga aactcaccat cggcaggcag tggttcggtt taagagatgg cattagaggg  900
agcccagtct ggatgtggac ttggatgccc tgtgggtatc agttctgctg cactttggc   960
ccgaaataga tccagtgctg agcaagcaat gtacaccaga gcctcagtga gcccatctgc  1020
acagtgggga gcatggaggg atgggtttgg cctgtgcttc tgcttattca gtccttcagc  1080
tcacggaagg gatgctagtc cgtgaaggtg acctcacagt actggttaat taaactttat  1140
tgctcactgt ccactttgt gctgaaaaaa aa                                 1172
```

MARKERS SPECIFIC FOR PLURIPOTENT STEM CELLS, AND METHODS OF USING THE SAME

INCORPORATION BY REFERENCE OF SEQUENCE LISTING

The instant application contains a Sequence Listing which has been filed electronically in xml format and is hereby incorporated by reference in its entirety. Said xml copy, created on Sep. 9, 2022, is named SEQ_LIST.xml and is 61,558 bytes in size.

FIELD OF INVENTION

The present application contains a Sequence Listing that is hereby incorporated by reference in its entirety.

The present disclosure relates generally to markers specific for pluripotent stem cells. In particular, the present disclosure relates to nucleic acid and polypeptide markers that are selectively expressed by pluripotent stem cells; and to methods for detecting the presence and/or absence of one or a plurality of pluripotent stem cells, by detecting the presence and/or absence of one or a plurality of such markers.

BACKGROUND INFORMATION

Pluripotent stem cells (PSCs) are generally recognized to exhibit the capacity for unlimited self-renewal in vitro (i.e., the capacity to divide indefinitely in an undifferentiated state); and to have the capacity to differentiate into cell types representative of the three primary germ cell layers of the early embryo (i.e., the ectoderm, endoderm, and mesoderm). By being able to develop into these three germ layers, PSCs are thereby able to give rise to all the cell types of an adult organism. See Thomson et al. (Science, 1998; 282:1145-1147). Under particular circumstances, such as environmental conditions and/or changes in cell signaling pathways, PSCs exit the cycle of self-renewal, and differentiate into specialized cell types deriving from the three germ layers.

Initially, PSCs were derived from embryos (Embryonic Stem Cells; ESCs), although more recently, PSCs were shown to be producible from adult (somatic) cells by the expression of reprogramming factors. See Takahashi et al. (Cell, 2006, 126 (4): 663-76). These PSCs, termed Inducible PSCs (iPSCs), are generally producible by delivering genetic material encoding reprogramming factors to the somatic cell, which triggers the somatic cell to revert to a pluripotent state. Thus, iPSCs represent an important source of PSCs free from the ethical and technical constraints (e.g., producing patient-matched stem cell lines) that limit the practicality of ESCs.

As a result of their pluripotency, PSCs, such as iPSCs, are important in the fields of, for example, medical and scientific research, drug discovery, cell therapy, regenerative medicine, and tissue engineering. In applications where PSCs are subsequently differentiated into specialized cells, e.g., in tissue engineering, it is desirable to be able to determine whether any PSCs remain after the differentiation process. For instance, in cell therapy products and engineered tissue, the presence of residual undifferentiated PSCs represents a quality-control issue, since such cells have the potential to form teratomas in vivo (i.e., tumorigenicity).

Established techniques for detecting the presence of PSCs have included phenotypic pluripotency assays (e.g., embryoid body formation; teratoma formation in vivo), as well as molecular pluripotency assays, including detection of molecular markers associated with PSCs. However, many markers differentially expressed in PSCs used for this purpose also demonstrate some significant level of expression in differentiated cells (albeit, with a different expression level, and/or a different expression pattern), thus making it problematic and challenging to detect a small number of residual PSCs within a larger population of derived tissue cells.

SUMMARY OF INVENTION

The present disclosure addresses the above-described limitations in the art, by providing a subset of marker genes that are uniquely expressed in PSCs. Accordingly, these marker genes are useful as molecular markers for detecting the presence of even small numbers of PSCs, including, for example, small numbers of residual undifferentiated PSCs amongst populations of predominantly differentiated PSC-derived cells. Non-limiting embodiments of the disclosure include as follows.

[1] A method for detecting pluripotent stem cells, said method comprising:

(a) obtaining a sample of interest containing a plurality of cells;

(b) analyzing said sample of interest to detect expression of at least one marker gene, wherein said at least one marker gene expresses a transcript having a corresponding complementary DNA (cDNA) sequence that comprises a nucleotide sequence having at least 90% sequence identity to a nucleotide sequence selected from the group consisting of SEQ ID NOs: 1-28; and (c) determining that said sample of interest contains pluripotent stem cells when the expression of said at least one marker gene is detected in said sample of interest.

[2] The method of [1], wherein the sample of interest comprises induced pluripotent stem cells.

[3] The method of [1], wherein the sample of interest comprises embryonic pluripotent stem cells.

[4] The method of [1], wherein said plurality of cells in said sample of interest is in the form of a cell mixture, a cell aggregate, or a tissue.

[5] The method of [1], wherein in step (b), the expression of said at least one marker gene is detected by measuring the level of mRNA expression of said marker gene.

[6] The method of [1], wherein in step (b), the expression of said at least one marker gene is detected by measuring the level of an expressed protein encoded by said marker gene.

[7] The method of [5], wherein the expression of said at least one marker gene is detected by a process comprising a technique selected from the group consisting of droplet digital polymerase chain reaction (dd-PCR), polymerase chain reaction (PCR), reverse-transcriptase PCR (RT-PCR), quantitative PCR, quantitative RT-PCR, Northern blot analysis, differential gene expression, RNA protection assay, microarray analysis, hybridization assay, and next-generation sequencing.

[8] The method of [7], wherein said technique comprises microarray analysis or next-generation sequencing.

[9] A method for detecting pluripotent stem cells, said method comprising:

(a) obtaining a sample of interest containing a plurality of cells;

(b) measuring the expression level of at least one marker gene in said sample of interest, wherein said at least one marker gene expresses a transcript having a corresponding complementary DNA (cDNA) sequence that comprises a nucleotide sequence having at least 90% sequence identity to a nucleotide sequence selected from the group consisting of SEQ ID NOs: 1-28;

(c) comparing the expression level detected in step (b) to a reference expression level, said reference expression level having been obtained by measuring the expression level of said at least one marker gene in at least one reference sample, wherein said at least one reference sample comprises a plurality of cells, and wherein said at least one reference sample contains substantially no pluripotent stem cells; and (d) determining that said sample of interest contains pluripotent stem cells when the expression level detected in step (b) is greater than said reference expression level, or determining that said sample of interest contains substantially no pluripotent stem cells when the expression level detected in step (b) is equal to or less than said reference expression level.

[10] A method for quantifying the number of pluripotent stem cells in a sample, said method comprising:

(a) obtaining a sample of interest containing a plurality of cells;

(b) measuring the level of expression of at least one marker gene in said sample of interest, wherein said at least one marker gene expresses a transcript having a corresponding complementary DNA (cDNA) sequence that comprises a nucleotide sequence having at least 90% sequence identity to a nucleotide sequence selected from the group consisting of SEQ ID NOs: 1-28;

(c) comparing the expression level detected in step (b) to a reference expression level, said reference expression level having been obtained by measuring the expression level of said at least one marker gene in at least one reference sample, wherein said at least one reference sample comprises a plurality of cells, wherein said at least one reference sample comprises pluripotent stem cells, and wherein substantially all of the cells in said at least one reference sample are pluripotent stem cells; and (d) calculating the amount of pluripotent stem cells in said sample of interest based on the comparison in step (c).

[11] The method of [9], wherein the sample of interest comprises induced pluripotent stem cells.

[12] The method of [9], wherein the sample of interest comprises embryonic pluripotent stem cells.

[13] The method of [9], wherein said plurality of cells in said sample of interest is in the form of a cell mixture, a cell aggregate, or a tissue.

[14] The method of [9], wherein in step (b), the expression of the at least one marker gene is detected by measuring the level of mRNA expression of said marker gene.

[15] The method of [9], wherein in step (b), the expression of the at least one marker gene is detected by measuring the level of an expressed protein encoded by said marker gene.

[16] The method of [14], wherein the expression of the at least one marker gene is detected by a process comprising a technique selected from the group consisting of dd-PCR, polymerase chain reaction (PCR), reverse-transcriptase PCR (RT-PCR), quantitative PCR, quantitative RT-PCR, Northern blot analysis, differential gene expression, RNA protection assay, microarray analysis, hybridization assay, and next-generation sequencing.

[17] The method of [10], wherein the sample of interest comprises induced pluripotent stem cells.

[18] The method of [10], wherein the sample of interest comprises embryonic pluripotent stem cells.

[19] The method of [10], wherein said plurality of cells in said sample of interest is in the form of a cell mixture, a cell aggregate, or a tissue.

[20] The method of [10], wherein in step (b), the expression of the at least one marker gene is detected by measuring the level of mRNA expression of said marker gene.

[21] The method of [10], wherein in step (b), the expression of the at least one marker gene is detected by measuring the level of an expressed protein encoded by said marker gene.

[22] The method of [20], wherein the expression of the at least one marker gene is detected by a process comprising a technique selected from the group consisting of dd-PCR, polymerase chain reaction (PCR), reverse-transcriptase PCR (RT-PCR), quantitative PCR, quantitative RT-PCR, Northern blot analysis, differential gene expression, RNA protection assay, microarray analysis, hybridization assay, and next-generation sequencing.

[23] An assay for detecting residual iPSCs in a therapeutic product, said assay comprising:

(a) obtaining a sample of a therapeutic product produced from iPSCs, said sample containing a plurality of cells;

(b) analyzing said sample to detect expression of at least one marker gene, wherein said at least one marker gene expresses a transcript having a corresponding complementary DNA (cDNA) sequence that comprises a nucleotide sequence having at least 90% sequence identity to a nucleotide sequence selected from the group consisting of SEQ ID NOs: 1-28; and (c) determining that said therapeutic product contains residual iPSCs when the expression of said at least one marker gene is detected in said sample.

[24] The assay of [23], wherein said plurality of cells in said sample is in the form of a cell mixture, a cell aggregate, or a tissue.

[25] The assay of [23], wherein in step (b), the expression of the at least one marker gene is detected by measuring the level of mRNA expression of said marker gene.

[26] The assay of [23], wherein in step (b), the expression of the at least one marker gene is detected by measuring the level of an expressed protein encoded by said marker gene.

[27] The assay of [25], wherein the expression of the at least one marker gene is detected by a process comprising a technique selected from the group consisting of dd-PCR, polymerase chain reaction (PCR), reverse-transcriptase PCR (RT-PCR), quantitative PCR, quantitative RT-PCR, Northern blot analysis, differential gene expression, RNA protection assay, microarray analysis, hybridization assay, and next-generation sequencing.

[28] An assay for quantifying the number of residual iPSCs in a therapeutic product, said assay comprising:

(a) obtaining a sample of a therapeutic product produced from iPSCs, said sample containing a plurality of cells;

(b) measuring the level of expression of at least one marker gene in said sample, wherein said at least one marker gene expresses a transcript having a corresponding complementary DNA (cDNA) sequence that comprises a nucleotide sequence having at least 90% sequence identity to a nucleotide sequence selected from the group consisting of SEQ ID NOs: 1-28;

(c) comparing the expression level detected in step (b) to a reference expression level, said reference expression level having been obtained by measuring the expression level of said at least one marker gene in at least one reference sample, wherein said at least one reference sample comprises a plurality of cells, wherein said at least one reference sample comprises iPSCs, and wherein substantially all of the cells in said at least one reference sample are IPSCs; and (d) quantifying the number of residual iPSCs in said therapeutic product based on the comparison in step (c).

[29] The assay of [28], wherein said plurality of cells in said sample is in the form of a cell mixture, a cell aggregate, or a tissue.

[30] The assay of [28], wherein in step (b), the expression of the at least one marker gene is detected by measuring the level of mRNA expression of said marker gene.

[31] The assay of [28], wherein in step (b), the expression of the at least one marker gene is detected by measuring the level of an expressed protein encoded by said marker gene.

[32] The assay of [30], wherein the expression of the at least one marker gene is detected by a process comprising a technique selected from the group consisting of dd-PCR, polymerase chain reaction (PCR), reverse-transcriptase PCR (RT-PCR), quantitative PCR, quantitative RT-PCR, Northern blot analysis, differential gene expression, RNA protection assay, microarray analysis, hybridization assay, and next-generation sequencing.

[33] An assay for detecting residual iPSCs in a therapeutic product, said assay comprising:

(a) obtaining a sample of a therapeutic product produced from iPSCs, said sample containing a plurality of cells;

(b) measuring the expression level of at least one marker gene in said sample, wherein said at least one marker gene expresses a transcript having a corresponding complementary DNA (cDNA) sequence that comprises a nucleotide sequence having at least 90% sequence identity to a nucleotide sequence selected from the group consisting of SEQ ID NOs: 1-28;

(c) comparing the expression level detected in step (b) to a reference expression level, said reference expression level having been obtained by measuring the expression level of said at least one marker gene in at least one reference sample, wherein said at least one reference sample comprises a plurality of cells, and wherein said at least one reference sample contains substantially no pluripotent stem cells; and (d) determining that said therapeutic product contains residual iPSCs when the expression level detected in step (b) is greater than said reference expression level, or determining that said therapeutic product contains substantially no residual iPSCs when the expression level detected in step (b) is equal to or less than said reference expression level.

[34] The assay of [33], wherein said plurality of cells in said sample is in the form of a cell mixture, a cell aggregate, or a tissue.

[35] The assay of [33], wherein in step (b), the expression of the at least one marker gene is detected by measuring the level of mRNA expression of said marker gene.

[36] The assay of [33], wherein in step (b), the expression of the at least one marker gene is detected by measuring the level of an expressed protein encoded by said marker gene.

[37] The assay of [35], wherein the expression of the at least one marker gene is detected by a process comprising a technique selected from the group consisting of dd-PCR, polymerase chain reaction (PCR), reverse-transcriptase PCR (RT-PCR), quantitative PCR, quantitative RT-PCR, Northern blot analysis, differential gene expression, RNA protection assay, microarray analysis, hybridization assay, and next-generation sequencing.

[38] An assay for quantifying the number of residual iPSCs in a therapeutic product at different differentiation times, said assay comprising:

(a) obtaining a first sample of a therapeutic product, said first sample being obtained at a first differentiation time, or prior to the onset of differentiation, said first sample containing a plurality of cells;

(b) obtaining at least one additional sample of the therapeutic product at a different differentiation time, said at least one additional sample containing a plurality of cells;

(c) measuring the level of expression of at least one marker gene in the samples obtained in (a) and (b), wherein said at least one marker gene expresses a transcript having a corresponding complementary DNA (cDNA) sequence that comprises a nucleotide sequence having at least 90% sequence identity to a nucleotide sequence selected from the group consisting of SEQ ID NOs: 1-28; and (d) quantifying the number of iPSCs in said therapeutic product at different differentiation times, based on the measurements in step (c).

[39] The assay of [38], wherein said plurality of cells in said sample is in the form of a cell mixture, a cell aggregate, or a tissue.

[40] The assay of [38], wherein in step (c), the expression of the at least one marker gene is detected by measuring the level of mRNA expression of said marker gene.

[41] The assay of [38], wherein in step (c), the expression of the at least one marker gene is detected by measuring the level of an expressed protein encoded by said marker gene.

[42] The assay of [40], wherein the expression of the at least one marker gene is detected by a process comprising a technique selected from the group consisting of dd-PCR, polymerase chain reaction (PCR), reverse-transcriptase PCR (RT-PCR), quantitative PCR, quantitative RT-PCR, Northern blot analysis, differential gene expression, RNA protection assay, microarray analysis, hybridization assay, and next-generation sequencing.

[43] An assay for determining the purity of a differentiated product, said assay comprising:

(a) obtaining a sample of a differentiated product, said sample containing a plurality of cells;

(b) measuring the level of expression of at least one marker gene in said sample, wherein said at least one marker gene expresses a transcript having a corresponding complementary DNA (cDNA) sequence that comprises a nucleotide sequence having at least 90% sequence identity to a nucleotide sequence selected from the group consisting of SEQ ID NOs: 1-28;

(c) comparing the expression level detected in step (b) to a reference expression level, said reference expression level having been obtained by measuring the expression level of said at least one marker gene in at least one reference sample, wherein said at least one reference sample comprises a plurality of cells, wherein said at least one reference sample comprises iPSCs, and wherein substantially all of the cells in said at least one reference sample are iPSCs; and (d) calculating the amount of iPSCs in said sample based on the comparison in step (c), to thereby determine the purity of the differentiated product.

[44] The assay of [43], wherein said plurality of cells in said sample is in the form of a cell mixture, a cell aggregate, or a tissue.

[45] The assay of [43], wherein in step (b), the expression of the at least one marker gene is detected by measuring the level of mRNA expression of said marker gene.

[46] The assay of [43], wherein in step (b), the expression of the at least one marker gene is detected by measuring the level of an expressed protein encoded by said marker gene.

[47] The assay of [45], wherein the expression of the at least one marker gene is detected by a process comprising a technique selected from the group consisting of dd-PCR, polymerase chain reaction (PCR), reverse-transcriptase PCR (RT-PCR), quantitative PCR, quantitative RT-PCR, Northern blot analysis, differential gene expression, RNA protection assay, microarray analysis, hybridization assay, and next-generation sequencing.

[48] An assay for determining the purity of a differentiated product, said assay comprising:

(a) obtaining a sample of a differentiated product, said sample containing a plurality of cells;

(b) measuring the expression level of at least one marker gene in said sample, wherein said at least one marker gene expresses a transcript having a corresponding complementary DNA (cDNA) sequence that comprises a nucleotide sequence having at least 90% sequence identity to a nucleotide sequence selected from the group consisting of SEQ ID NOs: 1-28;

(c) comparing the expression level detected in step (b) to a reference expression level, said reference expression level having been obtained by measuring the expression level of said at least one marker gene in at least one reference sample, wherein said at least one reference sample comprises a plurality of cells, and wherein said at least one reference sample contains substantially no pluripotent stem cells; and (d) calculating the amount of iPSCs in said sample based on the comparison in step (c), to thereby determine the purity of the differentiated product.

[49] The assay of [48], wherein said plurality of cells in said sample is in the form of a cell mixture, a cell aggregate, or a tissue.

[50] The assay of [48], wherein in step (b), the expression of the at least one marker gene is detected by measuring the level of mRNA expression of said marker gene.

[51] The assay of [48], wherein in step (b), the expression of the at least one marker gene is detected by measuring the level of an expressed protein encoded by said marker gene.

[52] The assay of [50], wherein the expression of the at least one marker gene is detected by a process comprising a technique selected from the group consisting of dd-PCR, polymerase chain reaction (PCR), reverse-transcriptase PCR (RT-PCR), quantitative PCR, quantitative RT-PCR, Northern blot analysis, differential gene expression, RNA protection assay, microarray analysis, hybridization assay, and next-generation sequencing.

[53] A method for evaluating the capacity of an iPSC population to differentiate, said method comprising:

(a) obtaining a first sample of a population of iPSCs, said first sample being obtained before differentiation of said iPSCs is induced, said first sample containing a plurality of cells;

(b) obtaining at least one additional sample of the population of iPSCs, said at least one additional sample being obtained after differentiation of said iPSCs is induced, said at least one additional sample containing a plurality of cells;

(c) measuring the level of expression of at least one marker gene in the samples obtained in (a) and (b), wherein said at least one marker gene expresses a transcript having a corresponding complementary DNA (cDNA) sequence that comprises a nucleotide sequence having at least 90% sequence identity to a nucleotide sequence selected from the group consisting of SEQ ID NOs: 1-28; and (d) comparing the expression levels from the different samples detected in step (c) to each other, and/or to a reference expression level, to thereby evaluate the capacity of the iPSCs in said iPSCs population to differentiate.

[54] The method of [53], wherein said plurality of cells in said sample is in the form of a cell mixture, a cell aggregate, or a tissue.

[55] The method of [53], wherein in step (b), the expression of the at least one marker gene is detected by measuring the level of mRNA expression of said marker gene.

[56] The method of [53], wherein in step (b), the expression of the at least one marker gene is detected by measuring the level of an expressed protein encoded by said marker gene.

[57] The method of [55], wherein the expression of the at least one marker gene is detected by a process comprising a technique selected from the group consisting of dd-PCR, polymerase chain reaction (PCR), reverse-transcriptase PCR (RT-PCR), quantitative PCR, quantitative RT-PCR, Northern blot analysis, differential gene expression, RNA protection assay, microarray analysis, hybridization assay, and next-generation sequencing.

[58] A method for evaluating the pluripotency of a iPSC population, said method comprising:

(a) obtaining a sample of an iPSC population, said sample containing a plurality of cells;

(b) measuring the level of expression of at least one marker gene in said sample, wherein said at least one marker gene expresses a transcript having a corresponding complementary DNA (cDNA) sequence that comprises a nucleotide sequence having at least 90% sequence identity to a nucleotide sequence selected from the group consisting of SEQ ID NOs: 1-28;

(c) comparing the expression level detected in step (b) to a reference expression level, said reference expression level having been obtained by measuring the expression level of said at least one marker gene in at least one reference sample, wherein said at least one reference sample comprises a plurality of cells, wherein said at least one reference sample comprises iPSCs, and wherein substantially all of the cells in said at least one reference sample are iPSCs capable of differentiation; and (d) evaluating the pluripotency of the iPSCs in said iPSC population based on the comparison in step (c).

[59] The method of [58], wherein said plurality of cells in said sample is in the form of a cell mixture, a cell aggregate, or a tissue.

[60] The method of [58], wherein in step (b), the expression of the at least one marker gene is detected by measuring the level of mRNA expression of said marker gene.

[61] The method of [58], wherein in step (b), the expression of the at least one marker gene is detected by measuring the level of an expressed protein encoded by said marker gene.

[62] The method of [60], wherein the expression of the at least one marker gene is detected by a process comprising a technique selected from the group consisting of dd-PCR, polymerase chain reaction (PCR), reverse-transcriptase PCR (RT-PCR), quantitative PCR, quantitative RT-PCR, Northern blot analysis, differential gene expression, RNA protection assay, microarray analysis, hybridization assay, and next-generation sequencing.

[63] A method for evaluating the pluripotency of a iPSC population, said method comprising:

(a) obtaining a first sample of a population of iPSCs, said first sample being obtained before differentiation of said iPSCs is induced, said first sample containing a plurality of cells;

(b) obtaining at least one additional sample of the population of iPSCs, said at least one additional sample being obtained after differentiation of said iPSCs is induced, said at least one additional sample containing a plurality of cells;

(c) measuring the level of expression of at least one marker gene in the samples obtained in (a) and (b), wherein said at least one marker gene expresses a transcript having a corresponding complementary DNA (cDNA) sequence that comprises a nucleotide sequence having at least 90% sequence identity to a nucleotide sequence selected from the group consisting of SEQ ID NOs: 1-28;

(d) comparing the expression levels from the different samples detected in step (c) to each other, and/or to a reference expression level, to thereby evaluate the pluripotency of the iPSC cells in said iPSC population.

[64] The method of [63], wherein said plurality of cells in said sample is in the form of a cell mixture, a cell aggregate, or a tissue.

[65] The method of [63], wherein in step (b), the expression of the at least one marker gene is detected by measuring the level of mRNA expression of said marker gene.

[66] The method of [63], wherein in step (b), the expression of the at least one marker gene is detected by measuring the level of an expressed protein encoded by said marker gene.

[67] The method of [65], wherein the expression of the at least one marker gene is detected by a process comprising a technique selected from the group consisting of dd-PCR, polymerase chain reaction (PCR), reverse-transcriptase PCR (RT-PCR), quantitative PCR, quantitative RT-PCR, Northern blot analysis, differential gene expression, RNA protection assay, microarray analysis, hybridization assay, and next-generation sequencing.

[68] An assay kit for detecting residual iPSCs in a therapeutic product, said assay kit comprising at least one reagent suitable for specifically detecting the level of expression of at least one marker gene, wherein said at least one marker gene expresses a transcript having a corresponding complementary DNA (cDNA) sequence that comprises a nucleotide sequence having at least 90% sequence identity to a nucleotide sequence selected from the group consisting of SEQ ID NOs: 1-28.

[69] The assay kit of [68], wherein said reagent comprises a nucleic acid, a probe, or a primer, able to specifically detect the level of expression of at least one marker gene, wherein said at least one marker gene.

[70] An assay reagent for detecting residual iPSCs in a therapeutic product, wherein said reagent is able to specifically detect the level of expression of at least one marker gene, wherein said at least one marker gene expresses a transcript having a corresponding complementary DNA (cDNA) sequence that comprises a nucleotide sequence having at least 90% sequence identity to a nucleotide sequence selected from the group consisting of SEQ ID NOs: 1-28, and wherein said reagent comprises a nucleic acid, a probe, or a primer.

[71] An assay kit for quantifying the number of iPSCs in a therapeutic product, said assay kit comprising at least one reagent suitable for specifically detecting the level of expression of at least one marker gene, wherein said at least one marker gene expresses a transcript having a corresponding complementary DNA (cDNA) sequence that comprises a nucleotide sequence having at least 90% sequence identity to a nucleotide sequence selected from the group consisting of SEQ ID NOs: 1-28.

[72] The assay kit of [71], wherein said reagent comprises a nucleic acid, a probe, or a primer, able to specifically detect the level of expression of at least one marker gene, wherein said at least one marker gene.

[73] An assay reagent for quantifying the number of iPSCs in a therapeutic product, wherein said reagent is able to specifically detect the level of expression of at least one marker gene, wherein said at least one marker gene expresses a transcript having a corresponding complementary DNA (cDNA) sequence that comprises a nucleotide sequence having at least 90% sequence identity to a nucleotide sequence selected from the group consisting of SEQ ID NOs: 1-28, and wherein said reagent comprises a nucleic acid, a probe, or a primer.

[74] An assay kit for determining the purity of a differentiated product, said assay kit comprising at least one reagent suitable for specifically detecting the level of expression of at least one marker gene, wherein said at least one marker gene expresses a transcript having a corresponding complementary DNA (cDNA) sequence that comprises a nucleotide sequence having at least 90% sequence identity to a nucleotide sequence selected from the group consisting of SEQ ID NOs: 1-28.

[75] The assay kit of [74], wherein said reagent comprises a nucleic acid, a probe, or a primer, able to specifically detect the level of expression of at least one marker gene, wherein said at least one marker gene.

[76] An assay reagent for determining the purity of a differentiated product, wherein said reagent is able to specifically detect the level of expression of at least one marker gene, wherein said at least one marker gene expresses a transcript having a corresponding complementary DNA (cDNA) sequence that comprises a nucleotide sequence having at least 90% sequence identity to a nucleotide sequence selected from the group consisting of SEQ ID NOs: 1-28, and wherein said reagent comprises a nucleic acid, a probe, or a primer.

[77] An assay kit for evaluating the capacity of an iPSC population to differentiate, said assay kit comprising at least one reagent suitable for specifically detecting the level of expression of at least one marker gene, wherein said at least one marker gene expresses a transcript having a corresponding complementary DNA (cDNA) sequence that comprises a nucleotide sequence having at least 90% sequence identity to a nucleotide sequence selected from the group consisting of SEQ ID NOs: 1-28.

[78] The assay kit of [77], wherein said reagent comprises a nucleic acid, a probe, or a primer, able to specifically detect the level of expression of at least one marker gene, wherein said at least one marker gene.

[79] An assay reagent for evaluating the capacity of an iPSC population to differentiate, wherein said reagent is able to specifically detect the level of expression of at least one marker gene, wherein said at least one marker gene expresses a transcript having a corresponding complementary DNA (cDNA) sequence that comprises a nucleotide sequence having at least 90% sequence identity to a nucleotide sequence selected from the group consisting of SEQ ID NOs: 1-28, and wherein said reagent comprises a nucleic acid, a probe, or a primer.

[80] An assay kit for evaluating the pluripotency of an iPSC population, said assay kit comprising at least one reagent suitable for specifically detecting the level of expression of at least one marker gene, wherein said at least one marker gene expresses a transcript having a corresponding complementary DNA (cDNA) sequence that comprises a nucleotide sequence having at least 90% sequence identity to a nucleotide sequence selected from the group consisting of SEQ ID NOs: 1-28.

[81] The assay kit of [80], wherein said reagent comprises a nucleic acid, a probe, or a primer, able to specifically detect the level of expression of at least one marker gene, wherein said at least one marker gene.

[82] An assay reagent for evaluating the pluripotency of an iPSC population, wherein said reagent is able to specifically detect the level of expression of at least one marker gene, wherein said at least one marker gene expresses a transcript having a corresponding complementary DNA (cDNA) sequence that comprises a nucleotide sequence having at least 90% sequence identity to a nucleotide sequence selected from the group consisting of SEQ ID NOs: 1-28, and wherein said reagent comprises a nucleic acid, a probe, or a primer.

INCORPORATION BY REFERENCE

All patents, publications, and patent applications cited in the present specification are herein incorporated by reference as if each individual patent, publication, or patent application was specifically and individually indicated to be incorporated by reference in its entirety for all purposes.

DETAILED DESCRIPTION OF INVENTION

Figure 1:
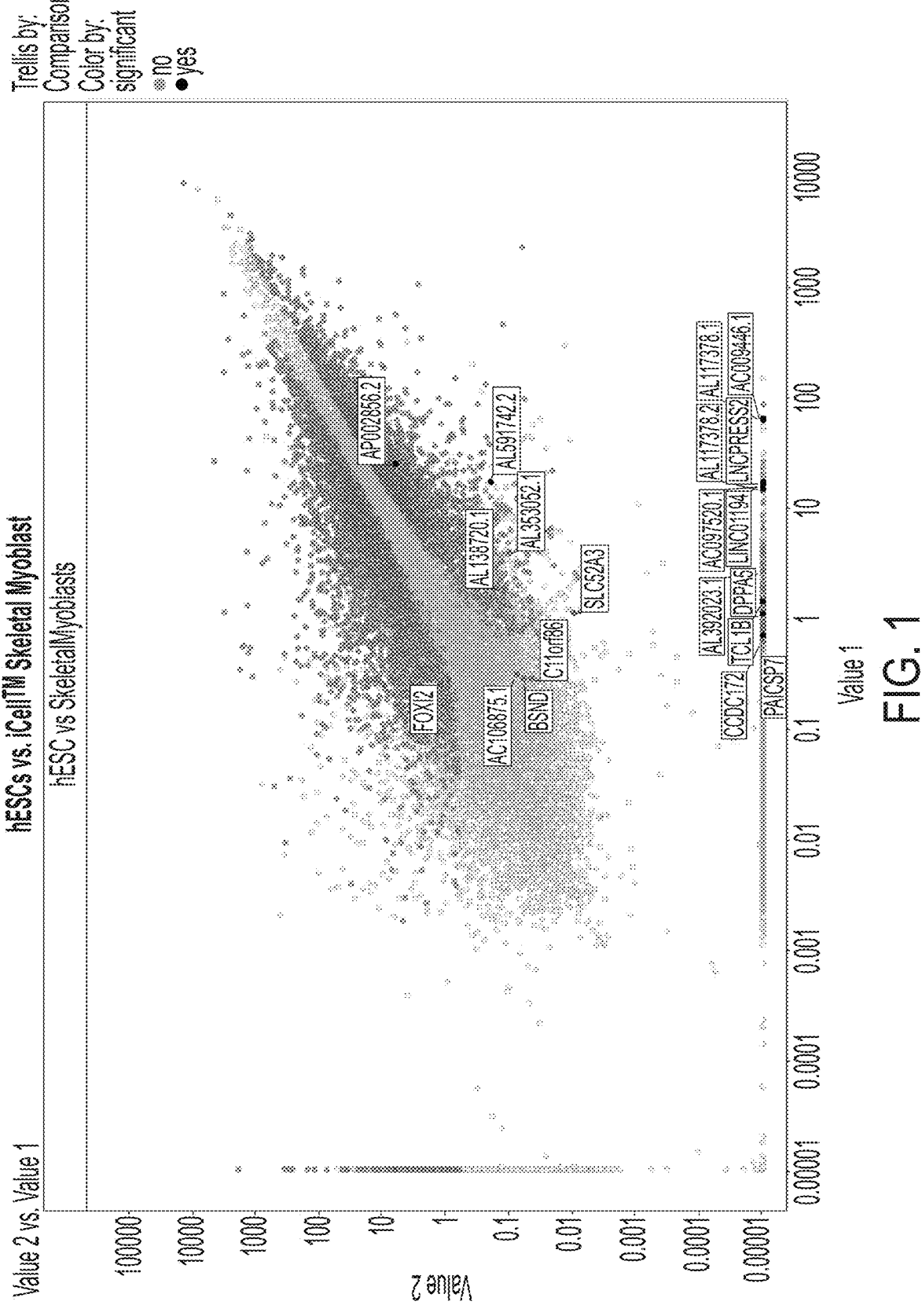
FIG. 1 depicts a plot of the $\log_{10}$ FPKM (Fragments Per Kilobase per Million reads mapped) values for various mRNAs in mRNA samples collected from human ESCs (X-axis) and human skeletal myoblasts (iCell® Skeletal Myoblasts; Y-axis).
Figure 2:
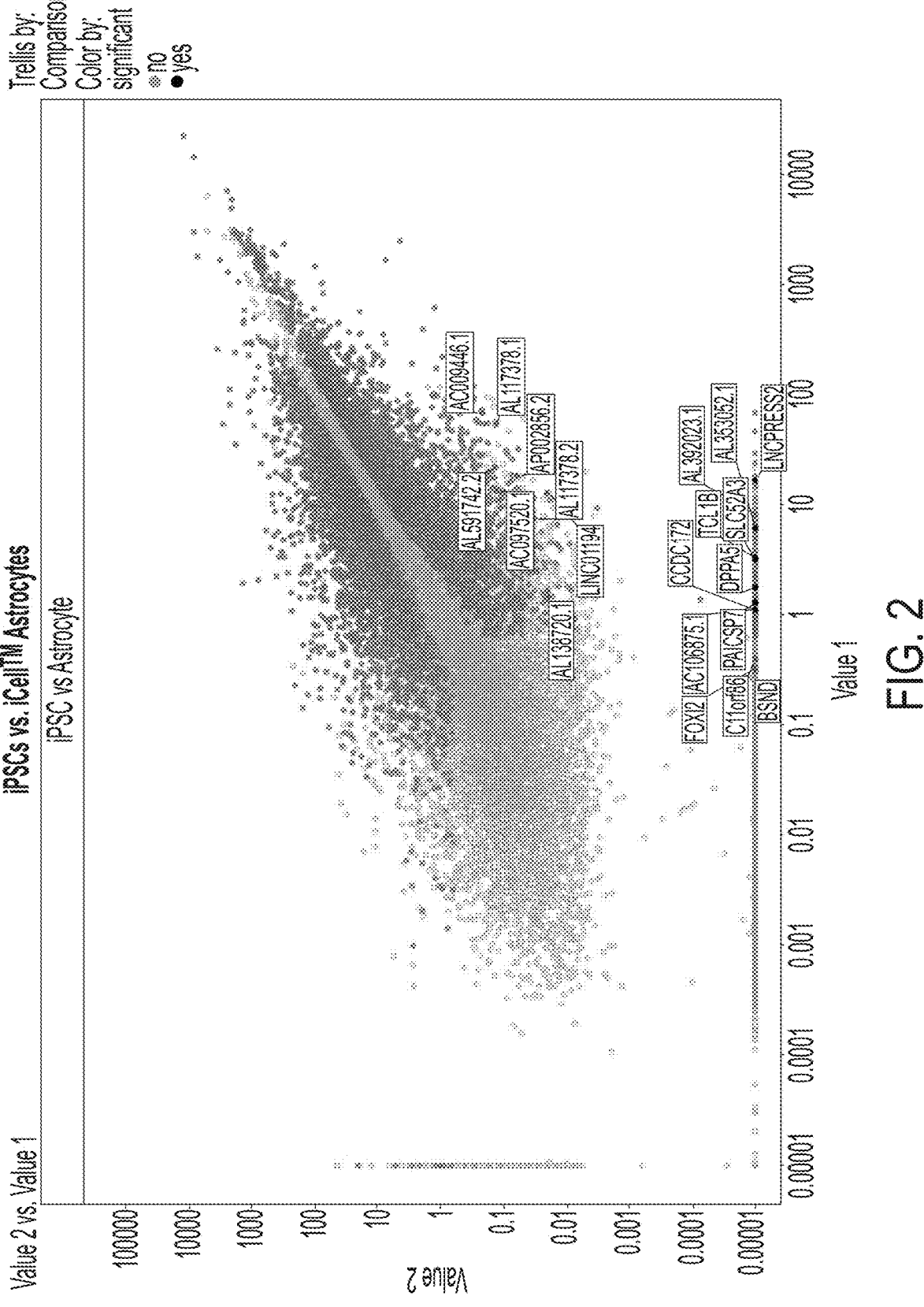
FIG. 2 depicts a plot of the $\log_{10}$ FPKM values for various mRNAs in mRNA samples collected from iPSCs (X-axis) and human astrocytes (iCell® Astrocytes; Y-axis).
Figure 3:
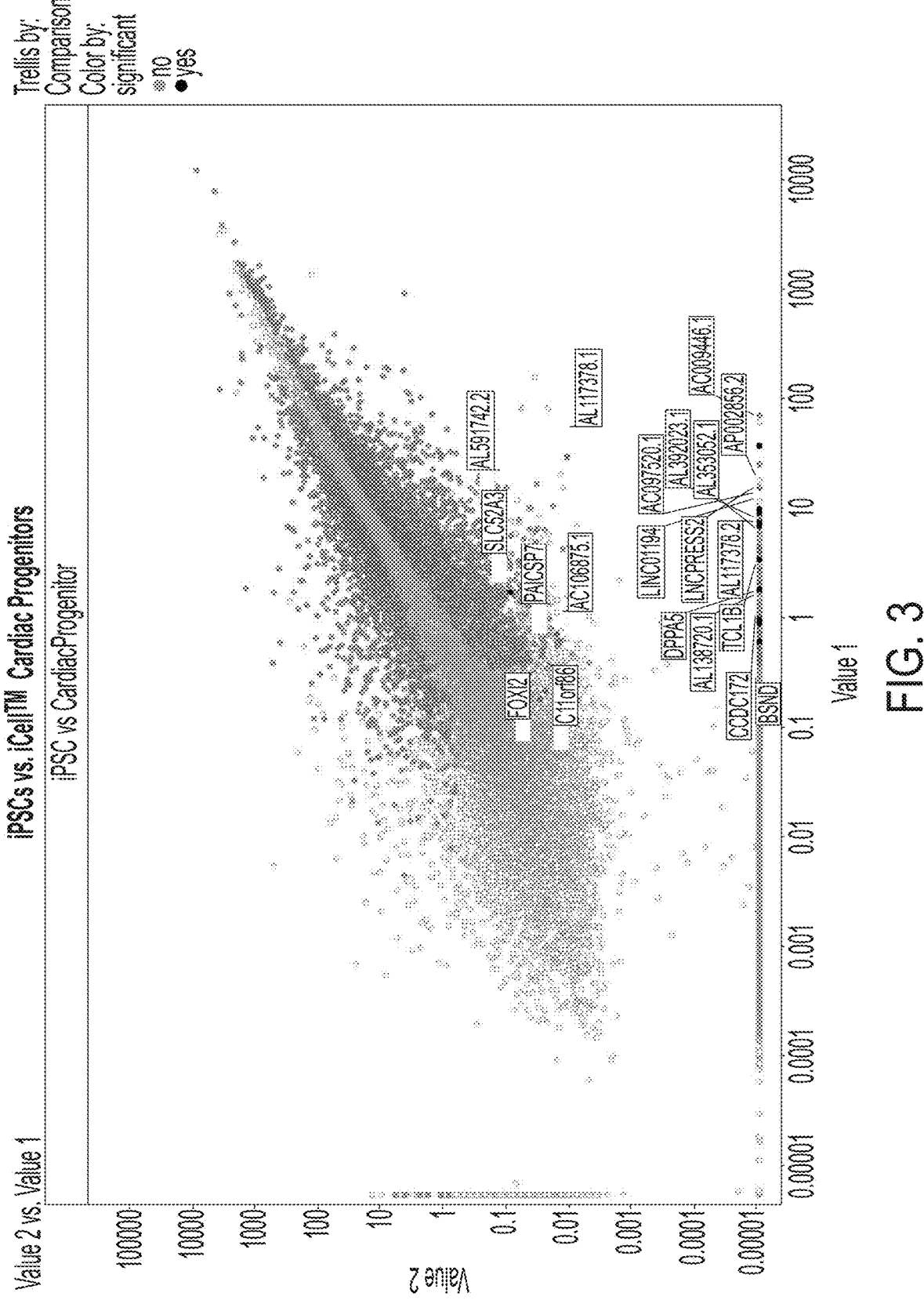
FIG. 3 depicts a plot of the $\log_{10}$ FPKM values for various mRNAs in mRNA samples collected from iPSCs (X-axis) and human cardiac progenitors (iCell® Cardiac Progenitor Cells; Y-axis).
Figure 4:
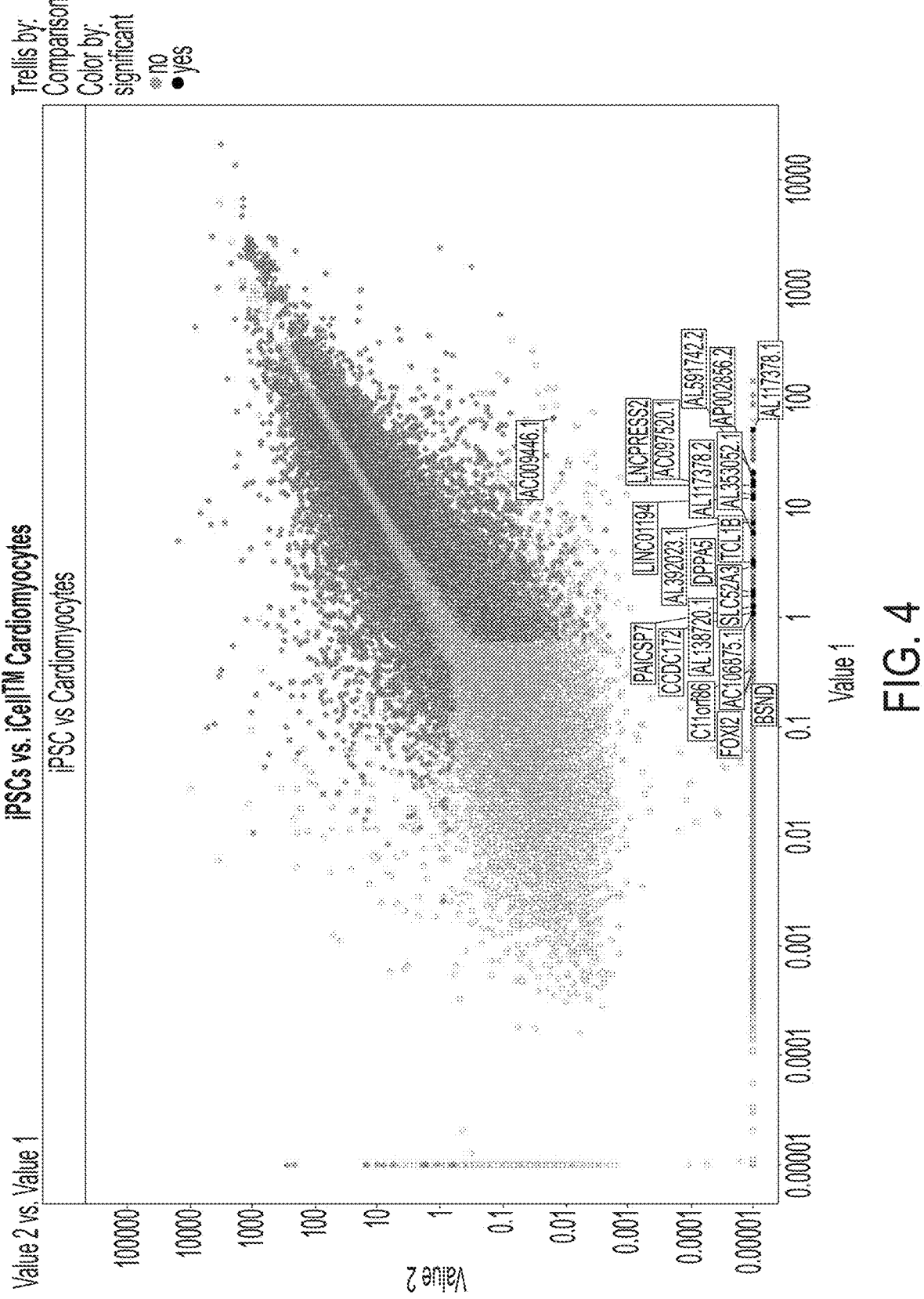
FIG. 4 depicts a plot of the $\log_{10}$ FPKM values for various mRNAs in mRNA samples collected from iPSCs (X-axis) and human cardiomyocytes (iCell® Cardiomyocytes; Y-axis).
Figure 5:
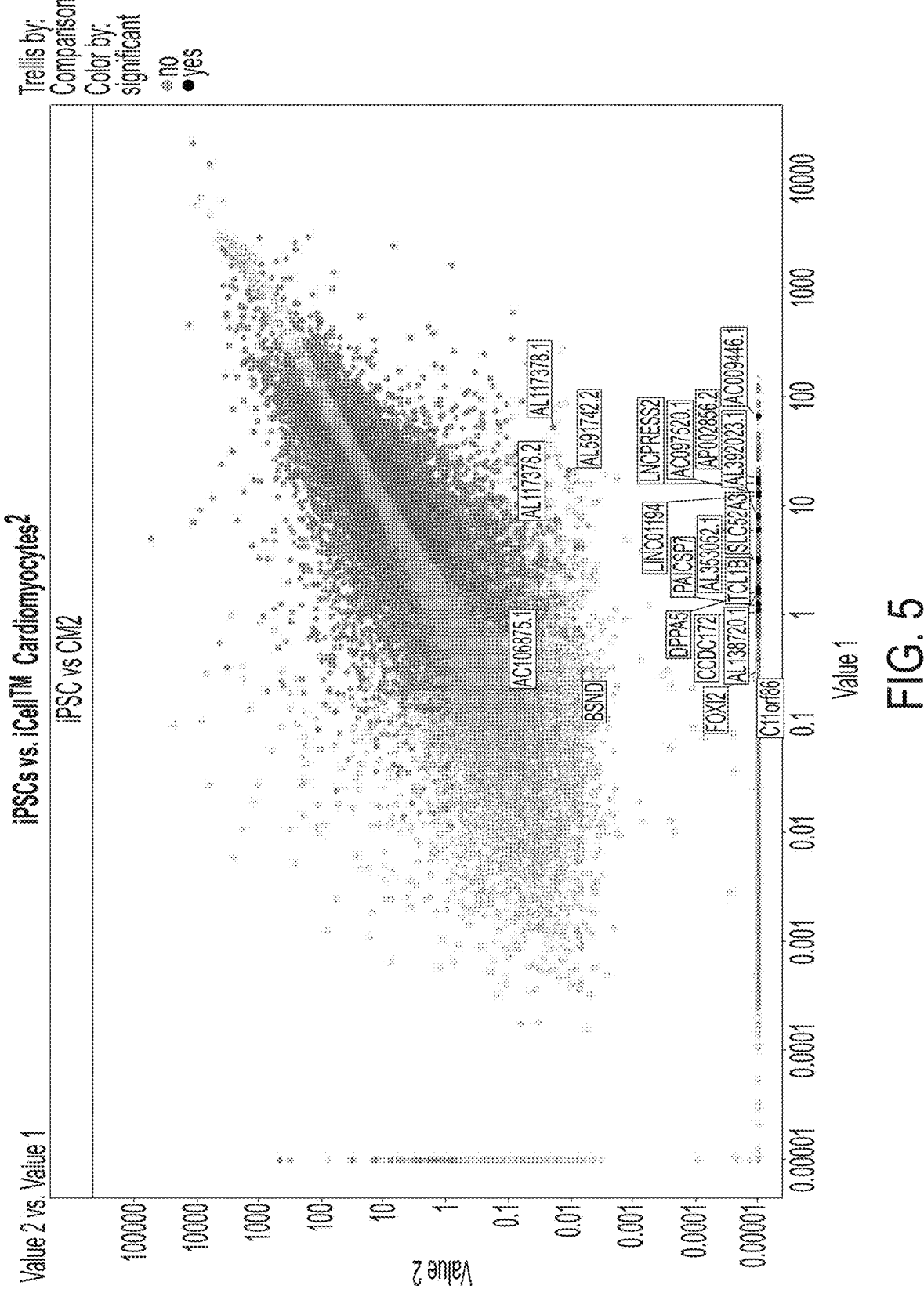
FIG. 5 depicts a plot of the $\log_{10}$ FPKM values for various mRNAs in mRNA samples collected from iPSCs (X-axis) and human cardiomyocytes (iCell®Cardiomyocytest²; Y-axis).
Figure 6:
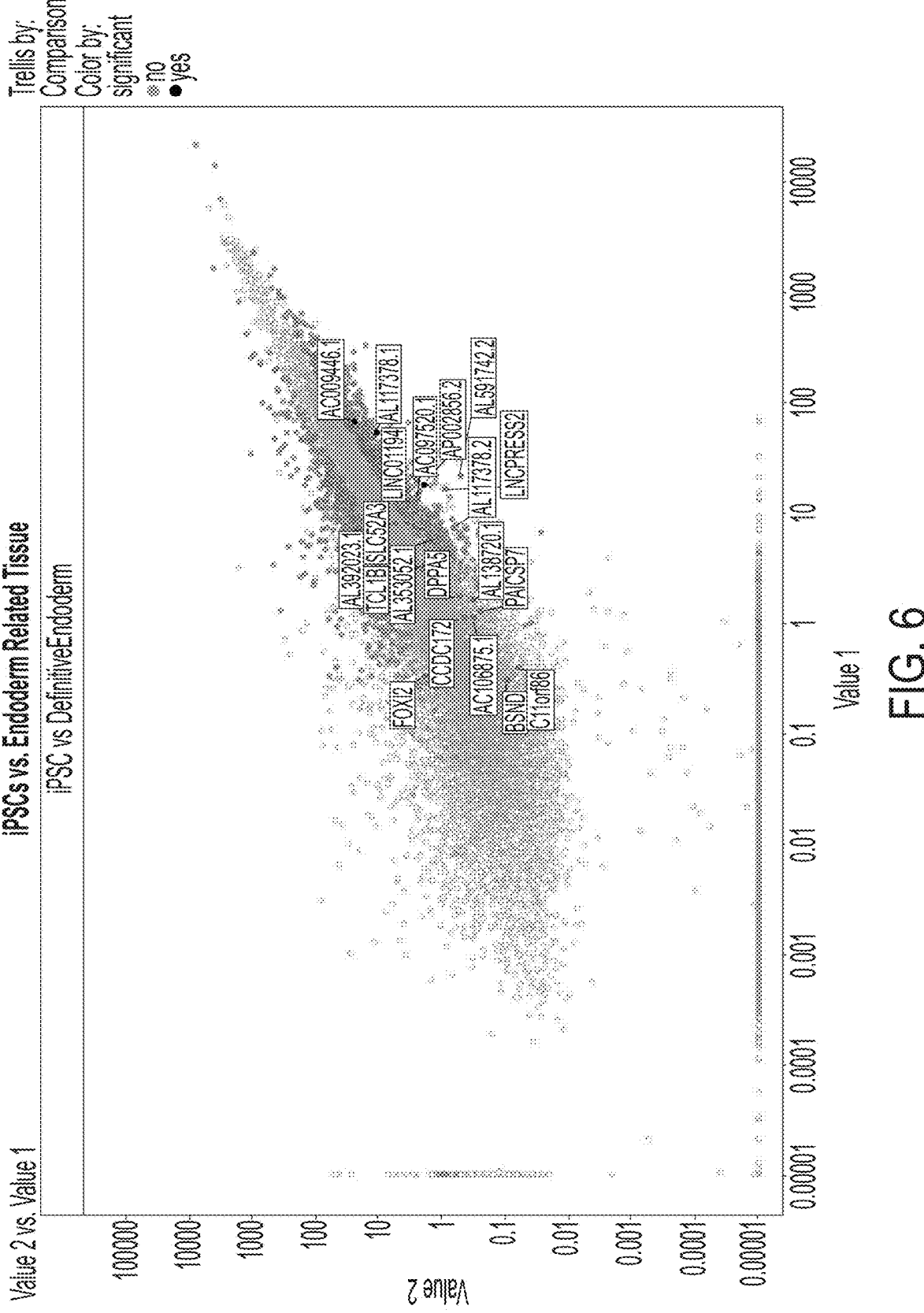
FIG. 6 depicts a plot of the $\log_{10}$ FPKM values for various mRNAs in mRNA samples collected from iPSCs (X-axis) and human endoderm related tissue (Y-axis).
Figure 7:
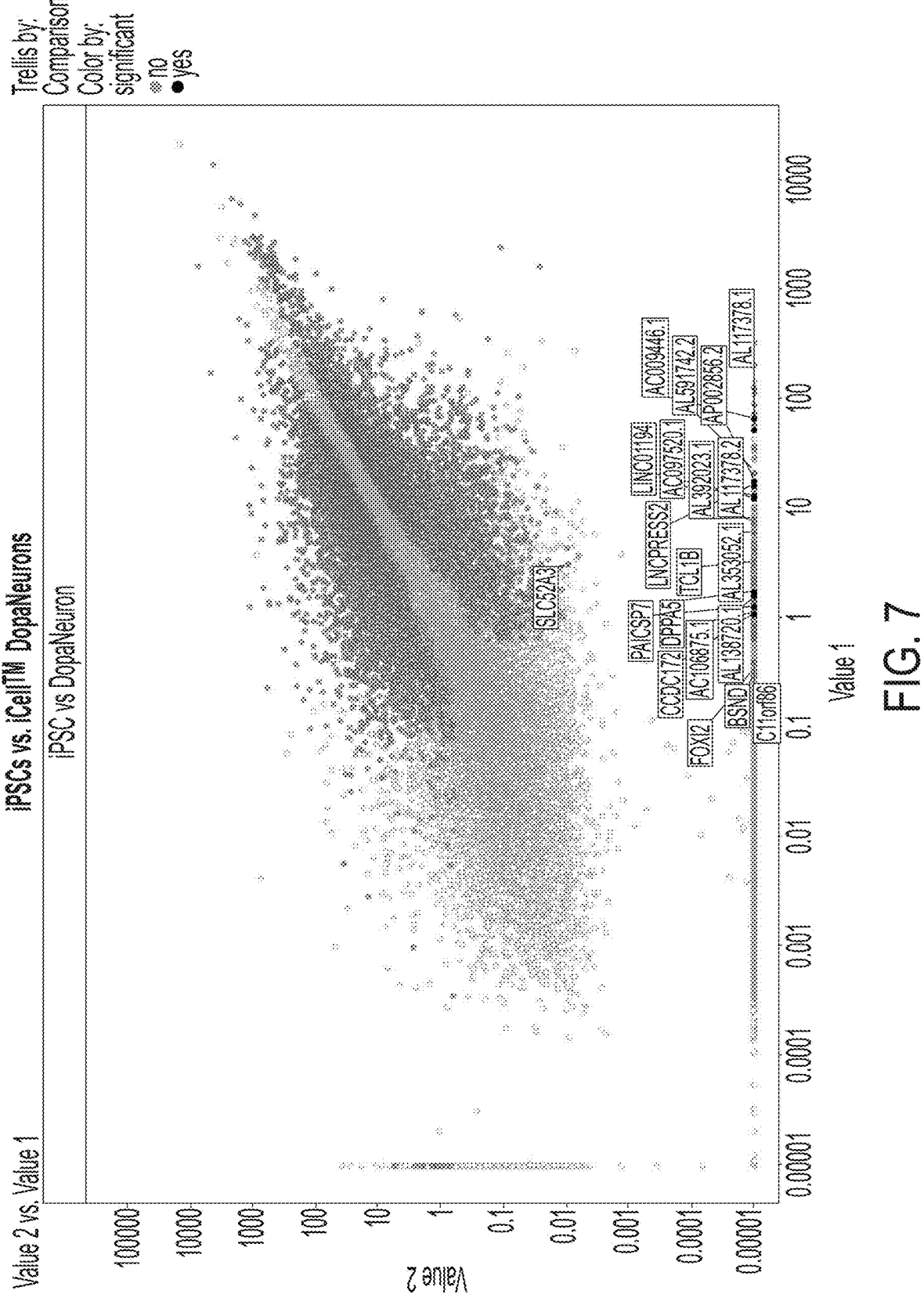
FIG. 7 depicts a plot of the $\log_{10}$ FPKM values for various mRNAs in mRNA samples collected from iPSCs (X-axis) and human floor plate-derived midbrain dopamine (DA) neurons (iCell® DopaNeurons; Y-axis).
Figure 8:
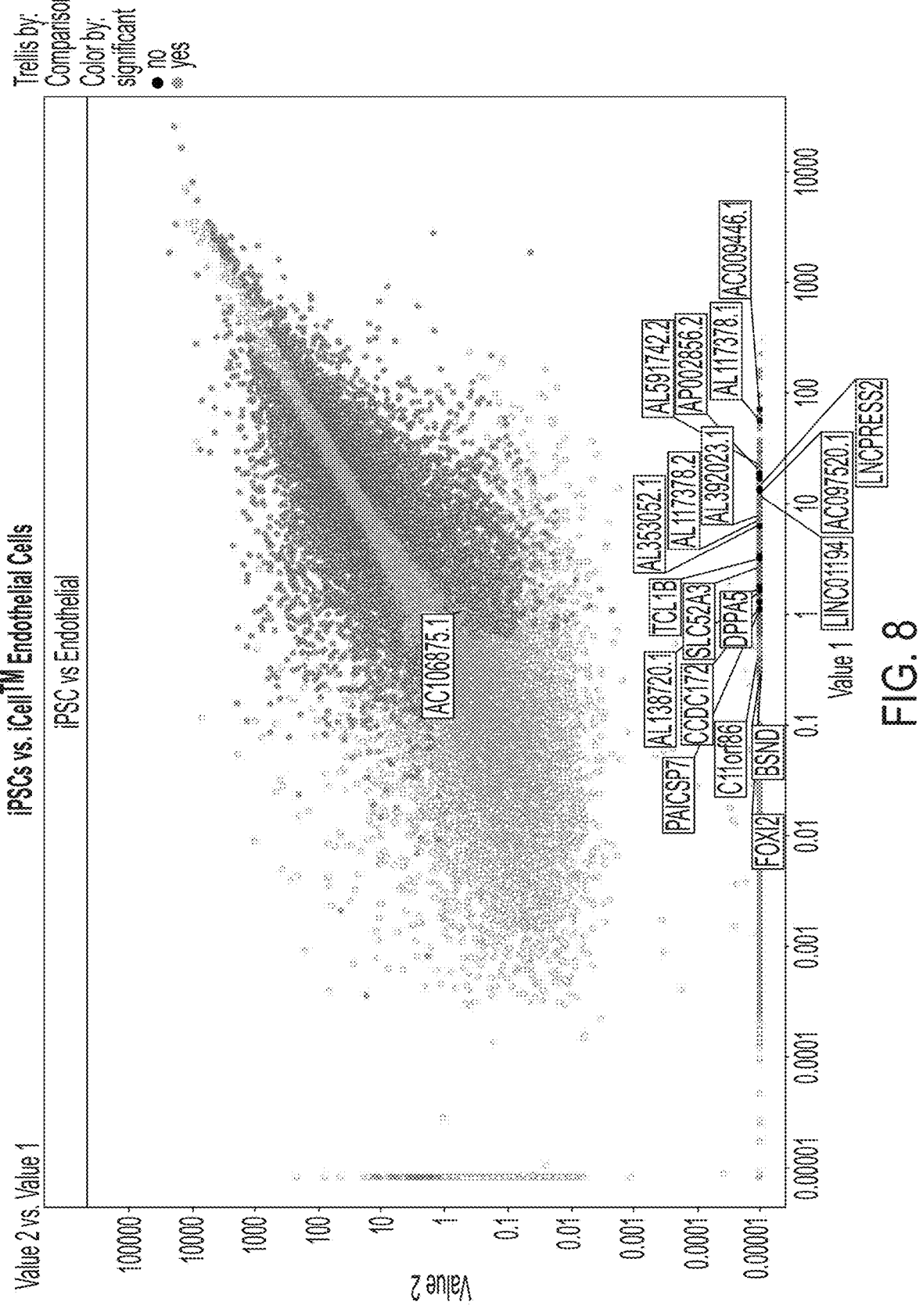
FIG. 8 depicts a plot of the $\log_{10}$ FPKM values for various mRNAs in mRNA samples collected from iPSCs (X-axis) and human endothelial cells (iCell® Endothelial Cells; Y-axis).
Figure 9:
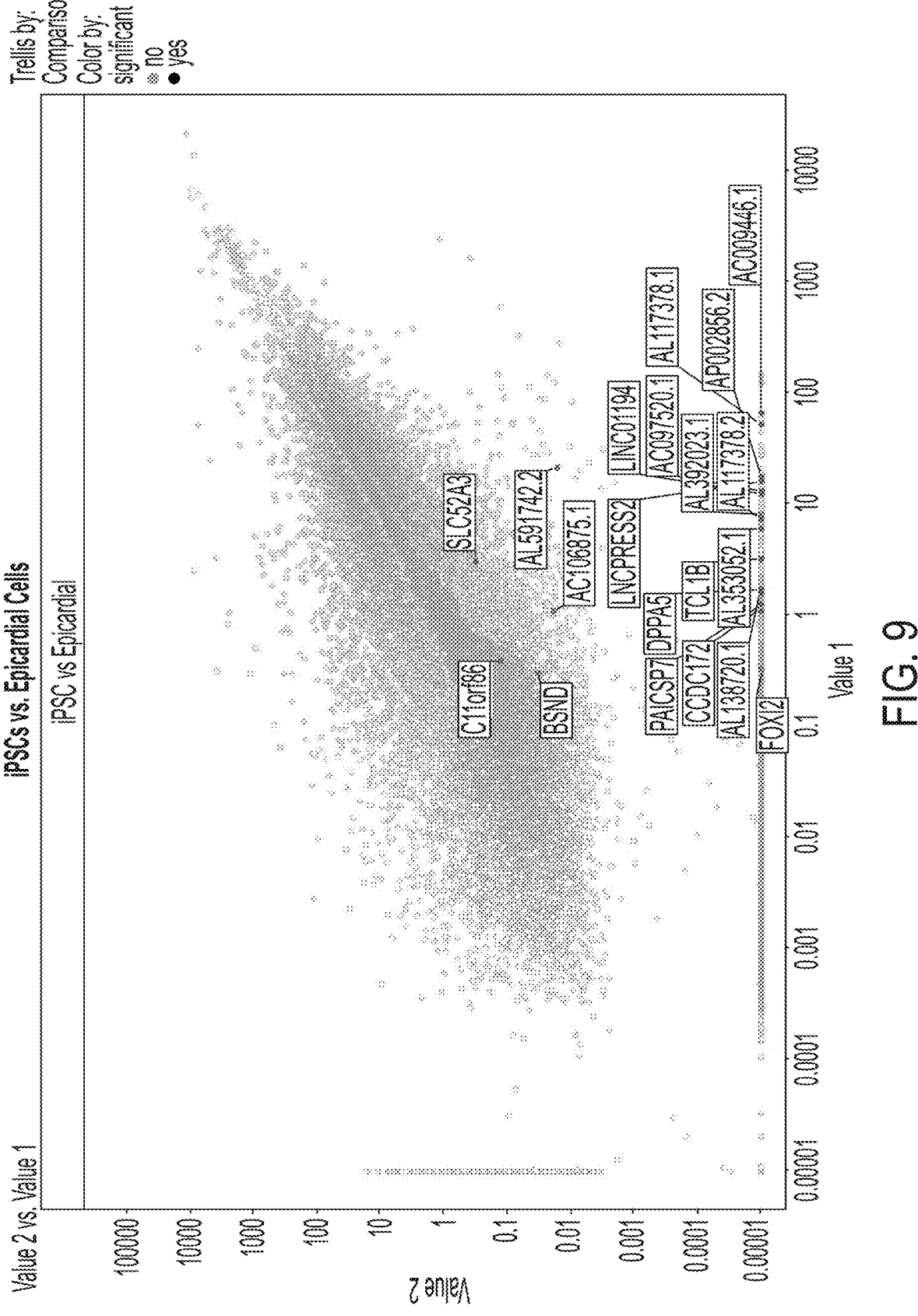
FIG. 9 depicts a plot of the $\log_{10}$ FPKM values for various mRNAs in mRNA samples collected from iPSCs (X-axis) and human epicardial cells (Y-axis).
Figure 10:
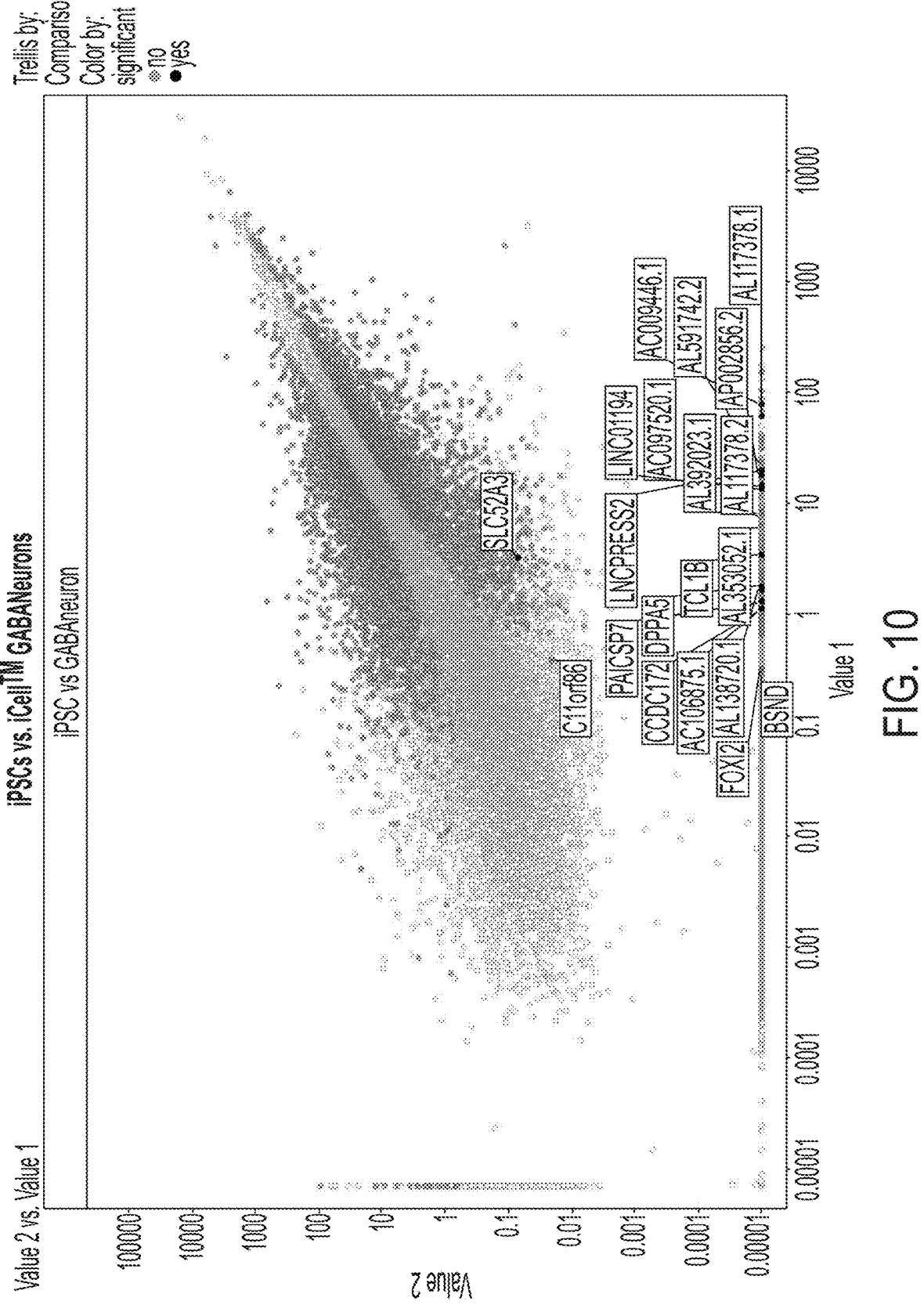
FIG. 10 depicts a plot of the $\log_{10}$ FPKM values for various mRNAs in mRNA samples collected from iPSCs (X-axis) and human cerebral cortical neurons (iCell® GABANeurons; Y-axis).
Figure 11:
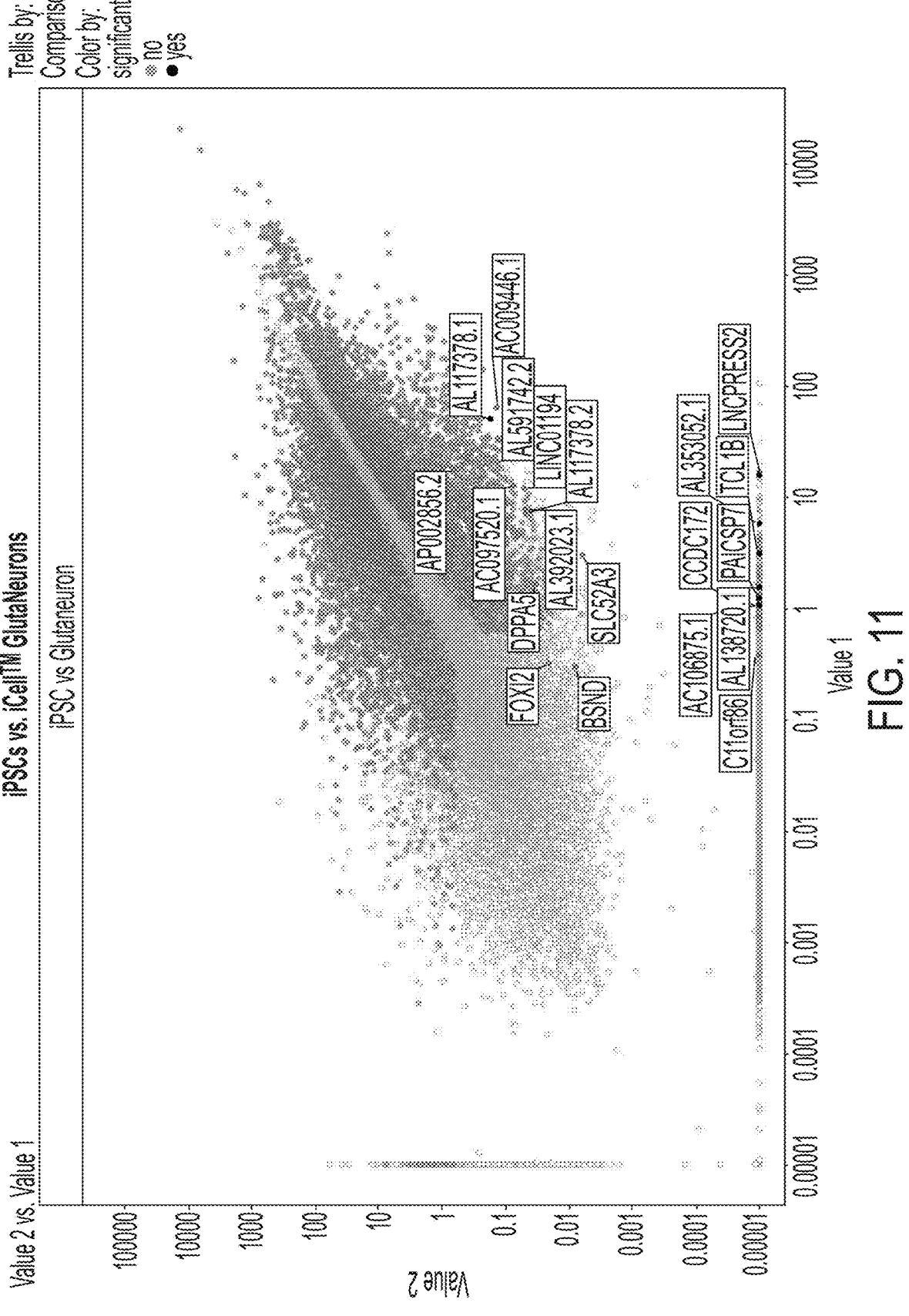
FIG. 11 depicts a plot of the $\log_{10}$ FPKM values for various mRNAs in mRNA samples collected from iPSCs (X-axis) and human glutamatergic-enriched cortical neurons (iCell® GlutaNeurons; Y-axis).
Figure 12:
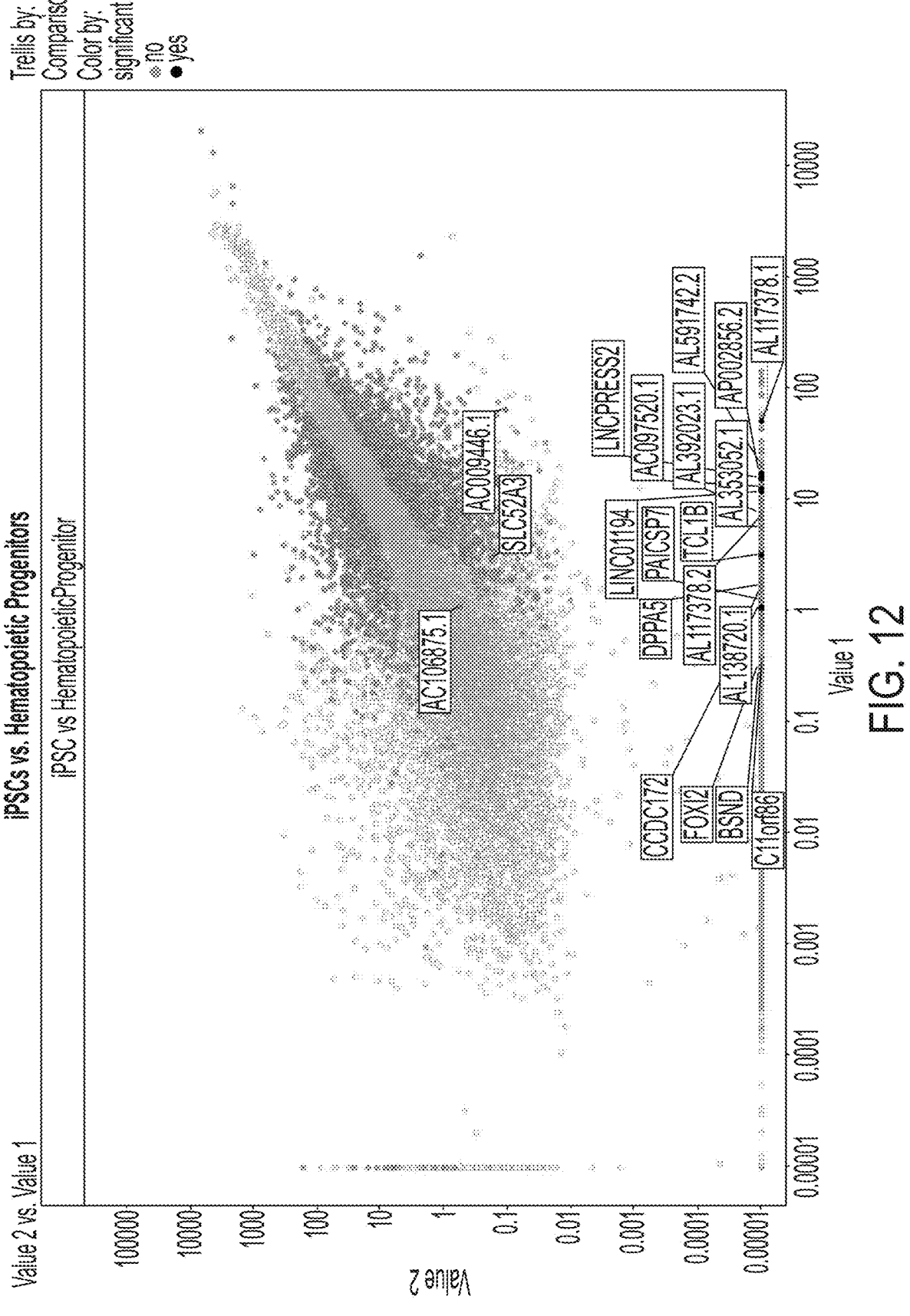
FIG. 12 depicts a plot of the $\log_{10}$ FPKM values for various mRNAs in mRNA samples collected from iPSCs (X-axis) and human hematopoietic progenitor cells (Y-axis).
Figure 13:
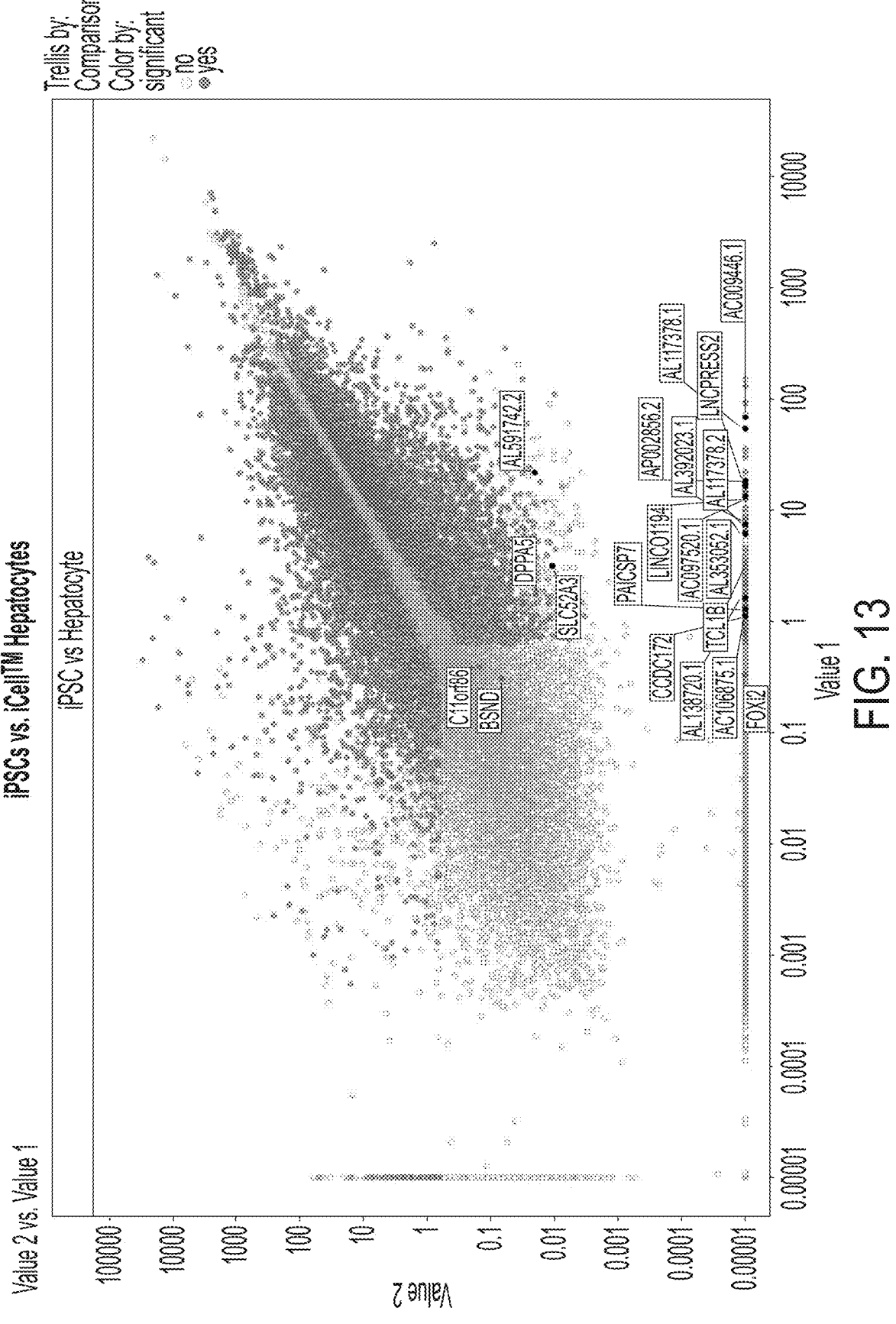
FIG. 13 depicts a plot of the $\log_{10}$ FPKM values for various mRNAs in mRNA samples collected from iPSCs (X-axis) and human hepatocytes (iCell® Hepatocytes; Y-axis).

It is to be understood that the terminology used herein is for the purpose of describing particular embodiments only and is not intended to be limiting. As used in the present specification and the appended claims, the singular forms "a," "an," and "the" include plural referents unless the context clearly dictates otherwise. Thus, for example, reference to "a cell" includes one or more cells.

Unless defined otherwise, all technical and scientific terms used herein have the same meaning as commonly understood by one of ordinary skill in the art to which the invention pertains. Although other methods and materials similar, or equivalent, to those described herein can be useful in the present invention, preferred materials and methods are described herein.

As used herein, "subject," "individual," or "patient" are used interchangeably herein and refer to any member of the phylum Chordata, including, without limitation, humans and other primates, including non-human primates, such as rhesus macaques, chimpanzees, and other monkey and ape species; farm animals, such as cattle, sheep, pigs, goats, and horses; domestic mammals, such as dogs and cats; laboratory animals, including rabbits, mice, rats, and guinea pigs; birds, including domestic, wild, and game birds, such as chickens, turkeys, and other gallinaceous birds, ducks, and geese; and the like. The term does not denote a particular age or gender. Thus, the term includes adult, young, and new-born individuals as well as males and females. In some embodiments, cells (for example, stem cells, including pluripotent stem cells, progenitor cells, or tissue-specific cells) are derived from a subject. In some embodiments, the subject is a non-human subject.

As used herein, "cell culture" refers to cells grown under controlled condition(s). A primary cell culture is a culture of cells, tissues, or organs, taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is often measured by the amount of time required for the cells to double in number, otherwise known as the doubling time.

As used herein, "feeder layer" refers to a layer of non-proliferating cells that can be used to support the proliferation of stem cells. Protocols for the production of feeder layers are known in the art, and are available on the internet, such as at the National Stem Cell Resource website, which is maintained by the American Type Culture Collection (ATCC).

As used herein, "differentiation" refers to processes by which unspecialized cells, such as pluripotent stem cells, or other stem cells, acquire specialized structural and/or functional features characteristic of mature cells. As used herein, "expand" or "proliferate" may refer to a process by which the number of cells in a cell culture is increased due to cell division. In certain embodiments herein, during an expansion or proliferation phase, the cells do not differentiate to form mature cells, but divide to form more (undifferentiated) cells.

As used herein, "embryoid bodies" refers to three-dimensional aggregates of pluripotent stem cells. These cells can undergo differentiation into cells of the three germ layers, the endoderm, mesoderm and ectoderm. The three-dimensional structure, including the establishment of complex cell adhesions and paracrine signaling within the embryoid body microenvironment, enables differentiation and morphogenesis.

As used herein, "stem cell" refers to a cell that has the capacity for self-renewal, i.e., the ability to go through numerous cycles of cell division while maintaining their non-terminally-differentiated state. Stem cells can be totipotent, pluripotent, multipotent, oligopotent, or unipotent. Stem cells may be, for example, embryonic, fetal, amniotic, adult, or induced pluripotent stem cells.

As used herein, "pluripotent stem cell" (PSC) refers to a cell that has the ability to reproduce itself indefinitely, and to differentiate into any other cell type of an adult organism. Generally, pluripotent stem cells are stem cells that are capable of inducing teratomas when transplanted in immunodeficient (SCID) mice; are capable of differentiating into cell types of all three germ layers (e.g., can differentiate into ectodermal, mesodermal, and endodermal, cell types); and express one or more markers characteristic of PSCs. Examples of such markers expressed by PSCs, such as embryonic stem cells (ESCs) and iPSCs, include October 4, alkaline phosphatase, SSEA-3 surface antigen, SSEA-4 surface antigen, nanog, TRA-1-60, TRA-1-81, SOX2, and REXI. A PSC within the scope of the present disclosure may be an embryonic stem cell (ESCs), or an induced pluripotent stem cell (iPSC), for example.

As used herein, "induced pluripotent stem cell" (iPSC) refers to a type of pluripotent stem cell that is artificially derived from a non-pluripotent cell, typically a somatic cell. In some embodiments, the somatic cell is a human somatic cell. Examples of somatic cells include, but are not limited to, dermal fibroblasts, bone marrow-derived mesenchymal cells, cardiac muscle cells, keratinocytes, liver cells, stomach cells, neural stem cells, lung cells, kidney cells, spleen cells, and pancreatic cells. Additional examples of somatic cells include cells of the immune system, including, but not limited to, B-cells, dendritic cells, granulocytes, innate lymphoid cells, megakaryocytes, monocytes/macrophages, myeloid-derived suppressor cells, natural killer (NK) cells, T cells, thymocytes, and hematopoietic stem cells.

iPSCs may be generated by reprogramming a somatic cell, by expressing or inducing expression of one or a combination of factors (herein referred to as reprogramming factors) in the somatic cell. iPSCs can be generated using fetal, postnatal, newborn, juvenile, or adult somatic cells. In some instances, factors that can be used to reprogram somatic cells to pluripotent stem cells include, for example, Oct4 (Oct3/4), Sox2, c-Myc, and Klf4, Nanog, and Lin28. In some embodiments, somatic cells may be reprogrammed by expressing at least two reprogramming factors, at least three reprogramming factors, or at least four reprogramming factors, to reprogram a somatic cell to a pluripotent stem cell. The cells may be reprogrammed by introducing reprogramming factors using vectors, including, for example, lentivirus, retrovirus, adenovirus, and Sendai virus vectors. Alternatively, non-viral techniques for introducing reprogramming factors include, for example, mRNA transfection, miRNA infection/transfection, PiggyBac, minicircle vectors, and episomal plasmids. iPSCs may also be generated by, for example, using CRISPR-Cas9-based techniques, to introduce reprogramming factors, or to activate endogenous programming genes.

As used herein, "embryonic stem cells" are embryonic cells derived from embryo tissue, preferably the inner cell mass of blastocysts or morulac, optionally that have been serially passaged as cell lines. The term includes cells isolated from one or more blastomeres of an embryo, preferably without destroying the remainder of the embryo. The term also includes cells produced by somatic cell nuclear transfer. ESCs can be produced or derived from a zygote, blastomere, or blastocyst-staged mammalian embryo produced by the fusion of a sperm and egg cell, nuclear transfer, or parthenogenesis, for example. Human ESCs include, without limitation, MA01, MA09, ACT-4, No. 3, H1, H7, H9, H14 and ACT30 embryonic stem cells. Exemplary pluripotent stem cells include embryonic stem cells derived from the inner cell mass (ICM) of blastocyst stage embryos, as well as embryonic stem cells derived from one or more blastomeres of a cleavage stage or morula stage embryo. These embryonic stem cells can be generated from embryonic material produced by fertilization or by asexual means, including somatic cell nuclear transfer (SCNT), parthenogenesis, and androgenesis. PSCs alone cannot develop into a fetal or adult animal when transplanted in utero because they lack the potential to contribute to all extraembryonic tissue (e.g., placenta in vivo or trophoblast in vitro).

As used herein, the terms "wild-type," "naturally occurring," and "unmodified" are used herein to mean the typical (or most common) form, appearance, phenotype, or strain existing in nature; for example, the typical form of cells, organisms, polynucleotides, proteins, macromolecular complexes, genes, RNAs, DNAs, or genomes as they occur in, and can be isolated from, a source in nature. The wild-type form, appearance, phenotype, or strain serve as the original parent before an intentional modification. Thus, mutant, variant, engineered, recombinant, and modified forms are not wild-type forms.

By "isolated" it is meant, when referring to, for instance, a cell, a polynucleotide or polypeptide molecule, including a marker molecule, for example, that the indicated molecule is separate and discrete from the whole organism with which the molecule is found in nature; and/or is present in the substantial absence of other biological macromolecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

The term "purified" as used herein preferably means that at least 75% by weight, more preferably at least 85% by weight, more preferably still at least 95% by weight, and most preferably at least 98% by weight, of the same molecule is present.

The terms "engineered," "genetically engineered," "genetically modified," "recombinant," "modified," "non-naturally occurring," and "non-native" indicate intentional human manipulation of the genome of an organism or cell. The terms encompass methods of genomic modification that include genomic editing, as defined herein, as well as techniques that alter gene expression or inactivation, enzyme engineering, directed evolution, knowledge-based design, random mutagenesis methods, gene shuffling, codon optimization, and the like. Methods for genetic engineering are known in the art.

As used herein, the terms "nucleic acid sequence," "nucleotide sequence," and "oligonucleotide" all refer to a polymeric forms of nucleotides. As used herein, the term "polynucleotide" refers to a polymeric form of nucleotides that, when in linear form, has one 5' end and one 3' end, and can comprise one or more nucleic acid sequences. The nucleotides may be deoxyribonucleotides (DNA), ribonucleotides (RNA), analogs thereof, or combinations thereof, and may be of any length. Polynucleotides may perform any function and may have various secondary and tertiary structures. The terms encompass known analogs of natural nucleotides and nucleotides that are modified in the base, sugar, and/or phosphate moieties. Analogs of a particular nucleotide have the same base-pairing specificity (e.g., an analog of A base pairs with T). A polynucleotide may comprise one modified nucleotide or multiple modified nucleotides. Examples of modified nucleotides include fluorinated nucleotides, methylated nucleotides, and nucleotide analogs. Nucleotide structure may be modified before or after a polymer is assembled. Following polymerization, polynucleotides may be additionally modified via, for example, conjugation with a labeling component or target binding component. A nucleotide sequence may incorporate non-nucleotide components. The terms also encompass nucleic acids comprising modified backbone residues or linkages, that are synthetic, naturally occurring, and/or non-naturally occurring, and have similar binding properties as a reference polynucleotide (e.g., DNA or RNA). Examples of such analogs include, but are not limited to, phosphorothioates, phosphoramidates, methyl phosphonates, chiral-methyl phosphonates, 2-O-methyl ribonucleotides, peptide-nucleic acids (PNAs), Locked Nucleic Acid (ENA®) (Exiqon, Inc., Woburn, MA) nucleosides, glycol nucleic acid, bridged nucleic acids, and morpholino structures. Peptide-nucleic acids (PNAs) are synthetic homologs of nucleic acids wherein the polynucleotide phosphate-sugar backbone is replaced by a flexible pseudo-peptide polymer. Nucleobases are linked to the polymer. PNAs have the capacity to hybridize with high affinity and specificity to complementary sequences of RNA and DNA. Polynucleotide sequences are displayed herein in the conventional 5' to 3' orientation unless otherwise indicated.

As used herein, "sequence identity" generally refers to the percent identity of nucleotide bases or amino acids comparing a first polynucleotide or polypeptide to a second polynucleotide or polypeptide using algorithms having various weighting parameters. Sequence identity between two polynucleotides or two polypeptides can be determined using sequence alignment by various methods and computer programs (e.g., Exonerate, BLAST, CS-BLAST, PASTA™, HMMER, L-ALIGN, and the like) available through the worldwide web at sites including, but not limited to, GEN-BANK (www.ncbi.nlm.nih.gov/genbank/) and EMBL-EBI® (www.ebi.ac.uk.). Sequence identity between two polynucleotides or two polypeptide sequences is generally calculated using the standard default parameters of the various methods or computer programs. A high degree of sequence identity between two polynucleotides or two polypeptides is often between about 90% identity and 100% identity over the length of the reference polynucleotide or polypeptide or query sequence, for example, about 90% identity or higher, about 91% identity or higher, about 92% identity or higher, about 93% identity or higher, about 94% identity or higher, about 95% identity or higher, about 96% identity or higher, about 97% identity or higher, about 98% identity or higher, or about 99% identity or higher, over the length of the reference polynucleotide or polypeptide or query sequence. Sequence identity can also be calculated for the overlapping region of two sequences where only a portion of the two sequences can be aligned.

A moderate degree of sequence identity between two polynucleotides or two polypeptides is often between about 80% identity to about 90% identity over the length of the reference polynucleotide or polypeptide or query sequence, for example, about 80% identity or higher, about 81% identity or higher, about 82% identity or higher, about 83% identity or higher, about 84% identity or higher, about 85% identity or higher, about 86% identity or higher, about 87% identity or higher, about 88% identity or higher, or about 89% identity or higher, but less than 90%, over the length of the reference polynucleotide or polypeptide or query sequence.

A low degree of sequence identity between two polynucleotides or two polypeptides is often between about 50% identity and 75% identity over the length of the reference polynucleotide or polypeptide or query sequence, for example, about 50% identity or higher, about 60% identity or higher, about 70% identity or higher, but less than 75% identity, over the length of the reference polynucleotide or polypeptide or query sequence.

The present disclosure contemplates polynucleotides and polypeptides, such as molecular markers, that may have less than 100% identity to a known or reference polynucleotide or polypeptide sequence (such as a known or reference marker polynucleotide sequence or a known or reference marker polypeptide sequence) or query sequence.

As used herein, "hybridization," "hybridize," or "hybridizing" is the process of combining two complementary single-stranded DNA or RNA molecules so as to form a single double-stranded molecule (DNA/DNA, DNA/RNA, RNA/RNA) through hydrogen base pairing. Hybridization stringency is typically determined by the hybridization temperature and the salt concentration of the hybridization buffer; e.g., high temperature and low salt provide high stringency hybridization conditions. Examples of salt concentration ranges and temperature ranges for different hybridization conditions are as follows: high stringency, approximately 0.01M to approximately 0.05M salt, hybridization temperature 5° C. to 10° C. below $T_m$; moderate stringency, approximately 0.16M to approximately 0.33M salt, hybridization temperature 20° C. to 29° C. below $T_m$; and low stringency, approximately 0.33M to approximately 0.82M salt, hybridization temperature 40° C. to 48° C. below $T_m$. $T_m$ of duplex nucleic acid sequences is calculated by standard methods well-known in the art (see, e.g., Maniatis, T., et al., Molecular Cloning: A Laboratory Manual, Cold Spring Harbor Laboratory Press: New York (1982); Casey, J., et al., Nucleic Acids Research 4:1539-1552 (1977); Bodkin, D. K., et al., Journal of Virological Methods 10 (1): 45-52 (1985); Wallace, R. B., et al., Nucleic Acids Research 9 (4): 879-894 (1981)). Algorithm prediction tools to estimate $T_m$ are also widely available. High stringency conditions for hybridization typically refer to conditions under which a polynucleotide complementary to a target sequence predominantly hybridizes with the target sequence, and substantially does not hybridize to non-target sequences. Typically, hybridization conditions are of moderate stringency, preferably high stringency.

As used herein, "complementarity" refers to the ability of a nucleic acid sequence to form hydrogen bonds with another nucleic acid sequence (e.g., through canonical Watson-Crick base pairing). A percent complementarity indicates the percentage of residues in a nucleic acid sequence that can form hydrogen bonds with a second nucleic acid sequence. If two nucleic acid sequences have 100% complementarity, the two sequences are perfectly complementary, i.e., all of the contiguous residues of a first polynucleotide hydrogen bond with the same number of contiguous residues in a second polynucleotide.

As used herein, "binding" refers to a non-covalent interaction between macromolecules (e.g., between a protein and a polynucleotide, between a polynucleotide and a polynucleotide, or between a protein and a protein, and the like). Such non-covalent interaction is also referred to as "associating" or "interacting" (e.g., if a first macromolecule interacts with a second macromolecule, the first macromolecule binds to second macromolecule in a non-covalent manner). Some portions of a binding interaction may be sequence-specific (the terms "sequence-specific binding," "sequence-specifically bind," "site-specific binding," and "site specifically binds" are used interchangeably herein). Binding interactions can be characterized by a dissociation constant (Kd). "Binding affinity" refers to the strength of the binding interaction. An increased binding affinity is correlated with a lower Kd.

"Gene" as used herein refers to a polynucleotide sequence comprising exons and related regulatory sequences. A gene may further comprise introns and/or untranslated regions (UTRs).

As used herein, the term "operably linked" refers to polynucleotide sequences or amino acid sequences placed into a functional relationship with one another. For example, regulatory sequences (e.g., a promoter or enhancer) are "operably linked" to a polynucleotide encoding a gene product if the regulatory sequences regulate or contribute to the modulation of the transcription of the polynucleotide. Operably linked regulatory elements are typically contiguous with the coding sequence. However, enhancers can function if separated from a promoter by up to several kilobases or more. Accordingly, some regulatory elements may be operably linked to a polynucleotide sequence but not contiguous with the polynucleotide sequence. Similarly, translational regulatory elements contribute to the modulation of protein expression from a polynucleotide. In some embodiments, the operably linked elements may be heterologous with each other.

As used herein, "expression" refers to transcription of a polynucleotide from a DNA template, resulting in, for example, a messenger RNA (mRNA) or other RNA transcript (e.g., non-coding, such as structural or scaffolding RNAs). The term further refers to the process through which transcribed mRNA is translated into peptides, polypeptides, or proteins. Transcripts and encoded polypeptides may be referred to collectively as "gene products." Expression may include splicing the mRNA in a eukaryotic cell, if the polynucleotide is derived from genomic DNA.

A "coding sequence" or a sequence that "encodes" a selected polypeptide, is a nucleic acid molecule that is transcribed (in the case of DNA) and translated (in the case of mRNA) into a polypeptide in vitro or in vivo when placed under the control of appropriate regulatory sequences. The boundaries of the coding sequence are determined by a start codon at the 5' terminus and a translation stop codon at the 3' terminus. A transcription termination sequence may be located 3' to the coding sequence.

As used herein, "a complementary DNA (cDNA) sequence" refers to a DNA sequence synthesized from an RNA template, generally via reverse transcription, and may include the first-strand cDNA molecule, the second-strand cDNA molecule, or a double-stranded cDNA molecule containing both first- and second-strand cDNAs. A "corresponding complementary DNA (cDNA) sequence," for a given RNA template (such as an mRNA transcript, for example), thereby refers to a DNA sequence that would result from reverse transcribing the RNA template.

As used herein, the term "modulate" refers to a change in the quantity, degree, or amount, of a property, activity, function or of a physical molecule. "Modulation" of gene expression includes both gene activation and gene repression. Modulation can be assayed by determining any characteristic directly or indirectly affected by the expression of the target gene. Such characteristics include, for example, changes in RNA or protein levels, protein activity, product levels, expression of the gene, or activity level of reporter genes.

As used herein, a "different" or "altered" expression level of, for example, a marker gene of the present disclosure, is a difference that is measurably different, and preferably, statistically significant (for example, not attributable to the standard error of the assay employed to assess expression). In some embodiments, a difference in expression level, e.g., of a marker gene of the present disclosure in a sample of interest as compared to a control or reference sample, may be, for example, a greater than 2-fold difference; a greater than 5-fold difference; a greater than 10-fold difference; a greater than 20-fold difference; a greater than 50-fold difference; a greater than 75-fold difference; a greater than 100-fold difference; a greater than 250-fold difference; a greater than 500-fold difference; a greater than 750-fold difference; a greater than 1,000-fold difference; a greater than 5,000-fold difference; a greater than 10,000-fold difference; a greater than 25,000-fold difference; a greater than 50,000-fold difference; a greater than 75,000-fold difference; a greater than 100,000-fold difference; a greater than 250,000-fold difference; a greater than 500,000-fold difference; a greater than 750,000-fold difference; a greater than 1,000,000-fold difference; a greater than 2,500,000-fold difference; a greater than 5,000,000-fold difference; a greater than 7,500,000-fold difference; a greater than 10,000,000-fold difference; a greater than 50,000,000-fold difference; a greater than 100,000,000-fold difference; a greater than 250,000,000-fold difference; a greater than 500,000,000-fold difference; a greater than 750,000,000 fold difference; a greater than 1,000,000,000-fold difference; a greater than 5,000,000,000-fold difference; or a greater than 10,000,000,000-fold difference, for example, depending on the gene expression being analyzed; and the analysis technique, for example.

"Vector" and "plasmid" as used herein refer to a polynucleotide vehicle to introduce genetic material into a cell. Vectors can be linear or circular. Vectors can contain a replication sequence capable of effecting replication of the vector in a suitable host cell (e.g., an origin of replication). Upon transformation of a suitable host, the vector can replicate and function independently of the host genome or integrate into the host genome. Vector design depends, among other things, on the intended use and host cell for the vector, and the design of a vector of the invention for a particular use and host cell is within the level of skill in the art. The four major types of vectors are plasmids, viral vectors, cosmids, and artificial chromosomes. Often, vectors comprise an origin of replication, a multicloning site, and/or a selectable marker. An expression vector may comprise an expression cassette. By "recombinant virus" is meant a virus that has been genetically altered, e.g., by the addition or insertion of a heterologous nucleic acid construct into a viral genome or portion thereof.

As used herein, "expression cassette" refers to a polynucleotide construct generated using recombinant methods or by synthetic means and comprising regulatory sequences operably linked to a selected polynucleotide to facilitate expression of the selected polynucleotide in a host cell. For example, the regulatory sequences can facilitate transcription of the selected polynucleotide in a host cell, or transcription and translation of the selected polynucleotide in a host cell. An expression cassette can, for example, be integrated in the genome of a host cell or be present in a vector to form an expression vector.

As used herein, the term "between" is inclusive of end values in a given range (e.g., between about 1 and about 50 nucleotides in length includes 1 nucleotide and 50 nucleotides).

As used herein, the term "amino acid" refers to natural and synthetic (unnatural) amino acids, including amino acid analogs, modified amino acids, peptidomimetics, glycine, and D or L optical isomers.

As used herein, the terms "peptide," "polypeptide," and "protein" are interchangeable and refer to polymers of amino acids. A polypeptide may be of any length. It may be branched or linear, it may be interrupted by non-amino acids, and it may comprise modified amino acids. The terms also refer to an amino acid polymer that has been modified through, for example, acetylation, disulfide bond formation, glycosylation, lipidation, phosphorylation, pegylation, biotinylation, cross-linking, and/or conjugation (e.g., with a labeling component or ligand). Polypeptide sequences are displayed herein in the conventional N-terminal to C-terminal orientation, unless otherwise indicated. Polypeptides and polynucleotides can be made using routine techniques in the field of molecular biology.

The terms "fusion protein" and "chimeric protein" as used herein refer to a single protein created by joining two or more proteins, protein domains, or protein fragments, that do not naturally occur together in a single protein. A fusion protein can comprise an epitope tag(s) (e.g., histidine tags, FLAG™ (Sigma Aldrich, St. Louis, MO) tags, Myc tags), reporter protein sequences (e.g., glutathione-S-transferase, beta-galactosidase, luciferase, green fluorescent protein, cyan fluorescent protein, yellow fluorescent protein), and/or nucleic acid sequence binding domains (e.g., a DNA binding domain or an RNA binding domain).

A "moiety" as used herein refers to a portion of a molecule. A moiety can be a functional group or describe a portion of a molecule with multiple functional groups (e.g., that share common structural aspects). The terms "moiety" and "functional group" are typically used interchangeably; however, a "functional group" can more specifically refer to a portion of a molecule that comprises some common chemical behavior. "Moiety" is often used as a structural description.

The terms "effective amount" or "therapeutically effective amount" of a composition or agent, such as an engineered tissue as provided herein, refers to a sufficient amount of the composition or agent to provide the desired response. Such responses will depend on the particular disease in question. For instance, in some embodiments, it is desirable to produce differentiated cells or tissue from PSCs to be administered to a subject to treat one or more symptoms, diseases, or deficiencies, for example.

"Transformation" as used herein refers to the insertion of an exogenous polynucleotide into a host cell, irrespective of the method used for insertion. For example, transformation can be by direct uptake, transfection, infection, and the like. The exogenous polynucleotide may be maintained as a nonintegrated vector, for example, an episome, or, alternatively, may be integrated into the host genome.

Methods for Producing iPSCs

The present disclosure relates, in part, to methods for detecting the presence of PSCs. In certain embodiments herein, the PSCs are residual undifferentiated PSCs present amongst a population(s) of predominantly PSC-derived differentiated cells.

The present disclosure contemplates the generation of iPSC cells from, for example, somatic cells, including human somatic cells. The somatic cell may be derived from a human or non-human animal, including, for example, humans and other primates, including non-human primates, such as rhesus macaques, chimpanzees, and other monkey and ape species; farm animals, such as cattle, sheep, pigs, goats, and horses; domestic mammals, such as dogs and cats; laboratory animals, including rabbits, mice, rats, and guinea pigs; birds, including domestic, wild, and game birds, such as chickens, turkeys, and other gallinaceous birds, ducks, and geese; and the like. In some embodiments, the somatic cell is selected from keratinizing epithelial cells, mucosal epithelial cells, exocrine gland epithelial cells, endocrine cells, liver cells, epithelial cells, endothelial cells, fibroblasts, muscle cells, cells of the blood and the immune system, cells of the nervous system including nerve cells and glial cells, pigment cells, and progenitor cells, including hematopoietic stem cells. The somatic cell may be fully differentiated (specialized), or may be less than fully differentiated. For instance, undifferentiated progenitor cells that are not PSCs, including somatic stem cells, and finally differentiated mature cells, can be used. The somatic cell may be from an animal of any age, including adult and fetal cells.

The somatic cell may be of mammalian origin. Allogenic cells can be used, if cells will be used for transplantation in vivo, for example. In some embodiments, iPSCs are not MHC-/HLA-matched to a subject. In some embodiments, iPSCs are MHC-/HLA-matched to a subject. In embodiments, for example, where iPSCs are to be used to produce PSC-derived cells for use in regenerative medicine, somatic cells may be obtained from the subject to be treated, or from another subject with the same or substantially the same HLA type as that of the subject. Somatic cells can be cultured before nuclear reprogramming, or can be reprogrammed without culturing after isolation, for example.

To introduce reprogramming factors into somatic cells, for example, viral vectors may be used, including, e.g., vectors from viruses such as SV40, adenovirus, vaccinia virus, adeno-associated virus, herpes viruses including HSV and EBV, Sindbis viruses, alphaviruses, human herpesvirus vectors (HHV) such as HHV-6 and HHV-7, and retroviruses. Lentiviruses include, but are not limited to, Human Immunodeficiency Virus type 1 (HIV-1), Human Immunodeficiency Virus type 2 (HIV-2), Simian Immunodeficiency Virus (SIV), Feline Immunodeficiency Virus (FIV), Equine Infectious Anaemia Virus (EIAV), Bovine Immunodeficiency Virus (BIV), Visna Virus of sheep (VISNA) and Caprine Arthritis-Encephalitis Virus (CAEV). Lentiviral vectors are capable of infecting non-dividing cells and can be used for both in vivo and in vitro gene transfer and expression of nucleic acid sequences. A viral vector can be targeted to a specific cell type by linkage of a viral protein, such as an envelope protein, to a binding agent, such as an antibody, or a particular ligand (for targeting to, for instance, a receptor or protein on or within a particular cell type).

In some embodiments, a viral vector, such as a lentiviral vector, can integrate into the genome of the host cell. The genetic material thus transferred is then transcribed and possibly translated into proteins inside the host cell. In other embodiments, viral vectors are used that do not integrate into the genome of a host cell.

A viral gene delivery system can be an RNA-based or DNA-based viral vector. An episomal gene delivery system can be a plasmid, an Epstein-Barr virus (EBV)-based episomal vector, a yeast-based vector, an adenovirus-based vector, a simian virus 40 (SV40)-based episomal vector, a bovine papilloma virus (BPV)-based vector, or a lentiviral vector, for example.

Somatic cells can be reprogrammed to produce induced pluripotent stem cells (iPSCs) using methods known to one of skill in the art. One of skill in the art can readily produce induced pluripotent stem cells, see for example, Published U.S. Patent Application No. 2009/0246875, Published U.S. Patent Application No. 2010/0210014; Published U.S. Patent Application No. 2012/0276636; U.S. Pat. Nos. 8,058,065; 8,129,187; and 8,268,620, all of which are incorporated herein by reference.

Generally, reprogramming factors which can be used to create induced pluripotent stem cells, either singly, in combination, or as fusions with transactivation domains, include, but are not limited to, one or more of the following genes: Oct4 (Oct3/4, Pou5fl), Sox (e.g., Sox1, Sox2, Sox3, Sox18, or Sox15), Klf (e.g., Klf4, Klf1, Klf3, Klf2 or Klf5), Myc (e.g., c-myc, N-myc or L-myc), nanog, or LIN28. As examples of sequences for these genes and proteins, the following accession numbers are provided: Mouse MyoD: M84918, NM_010866; Mouse Oct4 (POU5F1): NM_013633; Mouse Sox2: NM_011443; Mouse Klf4: NM_010637; Mouse c-Myc: NM_001177352, NM 001177353, NM_001177354 Mouse Nanog: NM_028016; Mouse Lin28: NM_145833: Human MyoD: NM_002478; Human Oct4 (POU5F1): NM_002701, NM 203289, NM_001173531; Human Sox2: NM_003106; Human Klf4: NM 004235; Human c-Myc: NM_002467; Human Nanog: NM_024865; and/or Human Lin28: NM_024674. Also contemplated are sequences similar thereto, including those having at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity. In some embodiments, at least three, or at least four, of Klf4, c-Myc, Oct3/4, Sox2, Nanog, and Lin28 are utilized. In other embodiments, Oct3/4, Sox2, c-Myc and Klf4 is utilized.

Exemplary reprogramming factors for the production of iPSCs include (1) Oct3/4, Klf4, Sox2, L-Myc (Sox2 can be replaced with Sox1, Sox3, Sox 15, Sox 17 or Sox18; Klf4 is replaceable with Klf1, Klf2 or Klf5); (2) Oct3/4, Klf4, Sox2, L-Myc, TERT, SV40 Large T antigen (SV40LT); (3) Oct3/4, Klf4, Sox2, L-Myc, TERT, human papilloma virus (HPV) 16 E6; (4) Oct3/4, Klf4, Sox2, L-Myc, TERT, HPV16 E7 (5)

Oct3/4, Klf4, Sox2, L-Myc, TERT, HPV16 E6, HPV16 E7; (6) Oct3/4, Klf4, Sox2, L-Myc, TERT, Bmil; (7) Oct3/4, Klf4, Sox2, L-Myc, Lin28; (8) Oct3/4, Klf4, Sox2, L-Myc, Lin28, SV40LT; (9) Oct3/4, Klf4, Sox2, L-Myc, Lin28, TERT, SV40LT; (10) Oct3/4, Klf4, Sox2, L-Myc, SV40LT; (11) Oct3/4, Esrrb, Sox2, L-Myc (Esrrb is replaceable with Esrrg); (12) Oct3/4, Klf4, Sox2; (13) Oct3/4, Klf4, Sox2, TERT, SV40LT; (14) Oct3/4, Klf4, Sox2, TERT, HPV16 E6; (15) Oct3/4, Klf4, Sox2, TERT, HPV16 E7; (16) Oct3/4, Klf4, Sox2, TERT, HPV16 E6, HPV16 E7; (17) Oct3/4, Klf4, Sox2, TERT, Bmil; (18) Oct3/4, Klf4, Sox2, Lin28 (19) Oct3/4, Klf4, Sox2, Lin28, SV40LT; (20) Oct3/4, Klf4, Sox2, Lin28, TERT, SV40LT; (21) Oct3/4, Klf4, Sox2, SV40LT; or (22) Oct3/4, Esrrb, Sox2 (Esrrb is replaceable with Esrrg).

During and after preparation of iPSCs, the cells can be cultured in suitable culture medium depending on the cell type, including, for example, Dulbecco's Modified Eagle's Medium (DMEM), DMEM F12 medium, Eagle's Minimum Essential Medium, F-12K medium, Iscove's Modified Dulbecco's Medium, Knockout DMEM, or RPMI-1640 medium. Also contemplated is supplementation of cell culture medium with mammalian serum. Examples of such serum include fetal bovine serum (FBS), bovine serum (BS), calf serum (CS), fetal calf serum (FCS), newborn calf serum (NCS), goat serum (GS), horse serum (HS), human serum, chicken serum, porcine serum, sheep serum, rabbit serum, rat serum (RS), serum replacements, and bovine embryonic fluid. For example, cells can be isolated and/or expanded with total serum (e.g., FBS) or serum replacement concentrations of about 0.5% to about 5% or greater including about 5% to about 15% or greater, such as about 20%, about 25% or about 30%.

Additional supplements can also be used to supply the cells with trace elements for optimal growth and expansion. Such supplements include insulin, transferrin, sodium selenium, and combinations thereof. These components can be included in a salt solution such as, but not limited to, Hanks' Balanced Salt Solution, Earle's Salt Solution, antioxidant supplements, MCDB-201, phosphate buffered saline (PBS), N-2-hydroxyethylpiperazine-N'-ethanesulfonic acid (HEPES), nicotinamide, ascorbic acid and/or ascorbic acid-2-phosphate, as well as additional amino acids. Such amino acids include, but are not limited to, L-alanine, L-arginine, L-aspartic acid, L-asparagine, L-cysteine, L-cysteine, L-glutamic acid, L-glutamine, L-glycine, L-histidine, L-inositol, L-isoleucine, L-leucine, L-lysine, L-methionine, L-phenylalanine, L-proline, L-serine, L-threonine, L-tryptophan, L-tyrosine, and L-valine.

Antibiotics are also typically used in cell culture to mitigate bacterial, mycoplasmal, and fungal contamination. Such antibiotics or anti-mycotic compounds may include, for example, penicillin/streptomycin, amphotericin, ampicillin, gentamicin, bleomycin, hygromycin, kanamycin, mitomycin, mycophenolic acid, nalidixic acid, neomycin, nystatin, paromomycin, polymyxin, puromycin, rifampicin, spectinomycin, tetracycline, tylosin, and zeocin.

Optionally, hormones can also be used in cell culture and include, but are not limited to, D-aldosterone, diethylstilbestrol (DES), dexamethasone, beta-estradiol, hydrocortisone, insulin, prolactin, progesterone, somatostatin/human growth hormone (HGH), thyrotropin, thyroxine, and L-thyronine. Beta-mercaptoethanol can also be supplemented in cell culture media.

Lipids and lipid carriers can also be used to supplement cell culture media, depending on the type of cell and the fate of the differentiated cell. Such lipids and carriers can include, but are not limited to, cyclodextrin, cholesterol, linoleic acid conjugated to albumin, linoleic acid and oleic acid conjugated to albumin, unconjugated linoleic acid, linoleic-oleic-arachidonic acid conjugated to albumin, oleic acid unconjugated and conjugated to albumin, among others. Albumin can similarly be used in fatty-acid free formulation.

Cells in culture can be maintained either in suspension or attached to a solid support, such as extracellular matrix components and synthetic or biopolymers. Additional factors useful for enhancing attachment to a solid support include, for example, type I, type II, and type IV collagen, concanavalin A, chondroitin sulfate, fibronectin, fibronectin-like polymers, gelatin, laminin, poly-D and poly-L-lysine, Matrigel, thrombospondin, and/or vitronectin.

Cultures of iPSCs can also contain cellular factors that allow iPSCs to remain in an undifferentiated form, including, for example, epidermal growth factor (EGF), platelet derived growth factor (PDGF), leukemia inhibitory factor (LIF), basic fibroblast growth factor (bFGF), and combinations thereof.

iPSCs typically display the characteristic morphology of human embryonic stem cells (hESCs), and express the pluripotency factor, NANOG. Embryonic stem cell specific surface antigens (SSEA-3, SSEA-4, TRA1-60, TRA1-81) may also be used to identify fully reprogrammed human cells. Additionally, at a functional level, PSCs, such as ESCs and iPSCs, also demonstrate the ability to differentiate into lineages from all three embryonic germ layers, and form teratomas in vivo (e.g., in SCID mice).

Methods for Differentiating PSCs

The present disclosure further contemplates differentiating PSCs, including ESCs and iPSCs, into differentiated (specialized) cells, and then, for example, distinguishing residual PSCs from the differentiated cells using marker genes described herein.

PSCs can be differentiated into any cell type of interest, including partially or fully specialized cells, such as, for example, hematopoietic progenitors, erythrocytes, B lymphocytes, T lymphocytes, natural killer cells, neutrophils, basophils, cosinophils, monocytes, macrophages, and platelets; neural progenitors; neurons, such as adrenergic or dopaminergic neurons, motor neurons, peripheral neurons, astrocytes and oligodendrocytes, microglia; pigment epithelial cells, skin cells and inner car cells; ab-sorptive cells, goblet cells, Paneth cells, and enteroendocrine cells; hepatocytes, pancreatic progenitor cells, insulin-producing cells, cholangiocytes, alveolar epithelial cells and intestinal epithelial cells; keratinocytes that occur at the base of hair follicles and give rise to both the hair follicle and to the epidermis; cardiomyocytes, cardiac progenitors, epicardial cells, skeletal muscle cells, skeletal myoblasts, endothelial cells, including vascular endothelial cells, hepatocytes, osteocytes, chondrocytes, renal progenitor cells and renal epithelial cells; mesenchymal stem cells; cells of endoderm related tissue. Methods for differentiating pluripotent stem cells are known in the art.

Markers for Detecting PSCs

The present disclosure contemplates the detection of markers specific for pluripotent stem cells, that can be used, for example, to confirm the presence and/or absence of one or a plurality of pluripotent stem cells in a sample. In particular, the present disclosure relates to nucleic acid and polypeptide markers that are selectively expressed by pluripotent stem cells; and to methods for detecting the presence and/or absence of one or a plurality of pluripotent stem cells, by detecting the presence and/or absence of one or a plurality of such markers.

In some embodiments of the invention, the expression of at least one marker gene is detected and/or measured. In some embodiments, the at least one marker gene expresses a transcript having a corresponding complementary DNA (cDNA) sequence that comprises a nucleotide sequence selected from the following: AC009446.1 (SEQ ID NO: 1); AC106875.1a (SEQ ID NO: 2); AC106875.1b (SEQ ID NO: 3); AL117378.1a (SEQ ID NO: 4); AL117378.1b (SEQ ID NO: 5); AL117378.1c (SEQ ID NO: 6); AL138720.1a (SEQ ID NO: 7); AL138720.1b (SEQ ID NO: 8); AL353052.1 (SEQ ID NO: 9); AL392023.1 (SEQ ID NO: 10); AL591742.2 (SEQ ID NO: 11); AP002856.2 (SEQ ID NO: 12); C11orf86 (SEQ ID NO: 13); CCDC172a (SEQ ID NO: 14); CCDC172b (SEQ ID NO: 15); CCDC172c (SEQ ID NO: 16); CCDC172d (SEQ ID NO: 17); DPPA5 (SEQ ID NO: 18); FOXI2 (SEQ ID NO: 19); LINC01194a (SEQ ID NO: 20); LINC01194b (SEQ ID NO: 21); LINC01194c (SEQ ID NO: 22); LINC01194d (SEQ ID NO: 23); LNC-PRESS2 (SEQ ID NO: 24); SLC52A3a (SEQ ID NO: 25); SLC52A3b (SEQ ID NO: 26); SLC52A3c (SEQ ID NO: 27); and TCL1B (SEQ ID NO: 28).

In some embodiments, the at least one marker gene expresses a transcript having a corresponding complementary DNA (cDNA) sequence that comprises a nucleotide sequence having less than 100% sequence identity to a nucleotide sequence selected from the group consisting of SEQ ID NOs: 1-28. For instance, contemplated herein is the detection of at least one marker gene that expresses a transcript having a corresponding complementary DNA (cDNA) sequence that comprises a nucleotide sequence having at least 70% sequence identity, at least 75% sequence identity, at least 80% sequence identity, at least 85% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity, to a nucleotide sequence selected from the group consisting of SEQ ID NOs: 1-28.

In some embodiments, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, or at least 27, of the above markers, or variant sequences thereof, may be detected. In some embodiments, all of the above markers are detected. These markers may be detected individually, in combination, sequentially, concurrently, simultaneously, and/or in conjunction with other markers that may or may not be specific for PSCs, including, for example, markers that are also expressed in differentiated cells, but at different amounts, or in different expression patterns, as compared to PSCs.

In some embodiments, the expression of one or more markers listed above is measured to determine the presence of PSCs in a composition, solution, cell aggregate, cell suspension, or tissue, for example.

In certain embodiments, the expression of the one or more markers in a plurality of cells, such as a composition, solution, cell aggregate, cell suspension, or tissue, is compared to the expression of the same one or more markers by a control, or reference, sample. The control or reference sample may contain a plurality of cells, such as a composition, solution, cell aggregate, cell suspension, or tissue. A control or reference sample may be, for example, one that contains a plurality of PSCs, such as ESCs, iPSCs, or both (e.g., a positive control). Additionally, or alternatively, a control or reference sample may be, for example, one that contains a plurality of non-PSCs, such as specialized cells; or non-terminally differentiated, non-PSCs (e.g., a negative control). In some embodiments, the control or reference sample contains substantially no PSCs. In some embodiments, the control or reference sample contains no PSCs. In some embodiments, the only cells, or substantially the only cells, in the control or reference sample, are PSCs. By "substantially no PSCs," it is meant that the amount of PSCs in the sample is less than or equal to the limit of detection under the assay conditions. By "substantially the only cells, in the control or reference sample, are PSCs," it is meant that the amount of non-PSCs in the sample is less than or equal to the limit of detection under the assay conditions.

In some embodiments, the expression level of one or more markers of the present disclosure in a sample of interest is compared to a control or reference value using normalized data. The normalization may be based, for example, on the expression level of one or more reference genes or gene products, e.g., a gene that is understood to be expressed in a constant manner between undifferentiated and differentiated cells; and/or under different conditions. Normalization of expression data may also be based on global gene expression patterns. Other data normalization methods contemplated herein include, for example, Global rank-invariant set normalization (GRSN); Cross correlation normalization (Xcorr); Non-parametric variable selection and approximation (NVSA); Kernel density weighted loess normalization (KWDL); Kernel density quantile normalization (KDQ); iterative rank-order normalization (IRON); Least-variant set normalization (LVS); Modified least-variant set normalization (LVSmiR); Invariants normalization; HMM assisted normalization (HMM); Biological scaling normalization (BSN); Support vector regression (SVR); Invariant set normalization (ISN); Spike-in standards; Weighted lowess normalization (wlowess); Weighted cyclic loess normalization (wcloess); Subset quantile normalization (SQN); loessm; Generalized Procrustes (GPA) analysis; Robust Multi-array Average (RMA); Cross normalization (Cross-Norm); Informative cross normalization (ICN); Global median; and dChip.

In high-throughput RNA/cDNA sequencing applications, such as RNA-seq for example, normalization may be based on gene length, sequencing depth, or both. For instance, normalized expression data may be expressed as RPM (Reads per million mapped reads), RPKM (Reads per kilo base per million mapped reads), TPM (Transcript per million), or FPKM (Fragments per kilo base per million mapped reads).

Marker expression may be assessed by any of a wide variety of well-known methods for detecting expression of a transcribed molecule (e.g., mRNA) or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In certain embodiments, the expression of the markers of the present disclosure can be measured by determining the level of messenger RNA (mRNA) expression of the marker gene(s). Such mRNA molecules can be isolated, derived, or amplified from a biological sample, such as a cell-containing composition, cell-containing solution, cell aggregate, cell suspension, or tissue, for example. Such mRNA can be analyzed directly; or a cDNA molecule corresponding thereto synthesized and used for further analysis, for instance.

When isolating RNA from tissue or cells, it may be important to prevent any further changes in gene expression after the tissue or cells have been removed from the culture. Changes in expression levels are known to change rapidly following perturbations, e.g., heat shock or activation with lipopolysaccharide (LPS) or other reagents. In addition, the RNA in the tissue and cells may quickly become degraded. Accordingly, in some embodiments, the tissue or cells obtained may be preserved, or rapidly frozen, for example, before analysis.

RNA can be extracted from tissue or cell samples by a variety of methods, e.g., guanidium thiocyanate lysis followed by CsCl centrifugation (Chirgwin et al., 1979, Biochemistry 18:5294-5299). RNA from single cells can be obtained as described in methods for preparing cDNA libraries from single cells, such as those described in Dulac, C. (1998) Curr. Top. Dev. Biol. 36, 245 and Jena et al. (1996) J. Immunol. Methods 190:199. Other methods and kits for RNA extraction are well known in the art.

An isolated RNA sample can also be enriched for particular species. For example, poly(A)+RNA may be isolated from an RNA sample. In general, such purification takes advantage of the poly-A tails on mRNA. For instance, poly-T oligonucleotides may be immobilized to serve as affinity ligands for mRNA. Kits for this purpose are commercially available, e.g., the MessageMaker kit (Life Technologies, Grand Island, N.Y.).

In some embodiments, an RNA population may be specifically enriched for certain sequences, including, for example, one or more marker sequences. Enrichment can be undertaken, e.g., by primer-specific cDNA synthesis, or multiple rounds of linear amplification based on cDNA synthesis and template-directed in vitro transcription (see, e.g., Wang et al. (1989) PNAS 86, 9717; Dulac et al., supra, and Jena et al., supra).

Isolated RNA, enriched or not in particular species or sequences, can be further amplified. For example, where RNA is mRNA, an amplification process such as RT-PCR can be utilized to amplify the mRNA, such that a signal is detectable or detection is enhanced. Such an amplification process is beneficial particularly when the tissue or cell sample, for example, is of a small size or volume.

Various amplification and detection methods can be used to assist in the detection of expression of a marker gene. For example, it is within the scope of the present disclosure to reverse transcribe mRNA into cDNA before further analysis (e.g., polymerase chain reaction, RT-PCR). Other known amplification methods which can be utilized herein include, but are not limited to, "NASBA" or "3SR" techniques; Q-beta amplification; strand displacement amplification; target mediated amplification; ligase chain reaction (LCR); self-sustained sequence replication (SSR); and transcription amplification.

Methods for detecting, characterizing, and/or quantitating, nucleic acid sequences; and for detecting, characterizing, and/or quantitating, mRNA expression, are known to persons skilled in the art, and include, but are not limited to, for example, PCR procedures, RT-PCR, quantitative PCR or RT-PCR, Northern blot analysis, differential gene expression, RNA protection assay, microarray analysis, hybridization methods, serial analysis of gene expression (SAGE), hybridization based on digital barcode quantification assays, multiplex RT-PCR, digital drop PCR (ddPCR), qRT-PCR, qPCR, UV spectroscopy, DNA sequencing, RNA sequencing, next-generation sequencing, including RNAseq, lysate-based hybridization assays utilizing branched DNA signal amplification, such as the QuantiGene® 2.0 Single Plex, and branched DNA analysis methods.

Non-limiting examples of nucleic acid sequencing techniques, e.g., for DNA sequencing and RNA sequencing, include Maxam-Gilbert sequencing, Sanger sequencing (i.e., chain-termination), sequencing-by-synthesis (SBS), sequencing-by-ligation, pyrosequencing, single-molecule real-time sequencing, MiSeq sequencing, massively parallel signature sequencing (MPSS), polony sequencing, 454® sequencing, nanopore sequencing. The present disclosure also encompasses, but is not limited to, next-generation sequencing technologies.

Non-limiting examples of next-generation sequencing technologies include, for example, Ion Torrent®, Illumina®, SOLID®, 454®; Massively Parallel Signature Sequencing solid-phase, reversible dye-terminator sequencing; and DNA nanoball sequencing. Digital barcode quantification assays can include the BeadArray (Illumina®), the xMAP® systems (Luminex®), the nCounter® (Nanostring®), the High Throughput Genomics (HTG) molecular, BioMark® (Fluidigm®), or the Wafergen microarray. Assays® can include DASL (Illumina®), RNA-Seq (Illumina®), TruSeq® (Illumina®), SureSelect (Agilent®), Bioanalyzer® (Agilent®) and TaqMan® (Thermo Fisher).

In general, PCR describes a method of gene amplification which is comprised of (i) sequence-specific hybridization of primers to specific genes or sequences within a nucleic acid sample or library, (ii) subsequent amplification involving multiple rounds of annealing, elongation, and denaturation using a thermostable DNA polymerase, and (iii) screening the PCR products for a band of the correct size. The primers used are oligonucleotides of sufficient length and appropriate sequence to provide initiation of polymerization, i.e., each primer is specifically designed to be complementary to a strand of the genomic locus to be amplified. The mRNA level of a gene can be determined by reverse-transcription (RT) PCR and by quantitative RT-PCR (QRT-PCR), or real-time PCR methods. Methods of RT-PCR and QRT-PCR are well known in the art. The nucleic acid sequences of exemplary marker genes are set forth herein. Accordingly, a skilled artisan can design an appropriate primer based on the disclosed sequences for determining the mRNA level of the respective marker gene.

Nucleic acid and ribonucleic acid (RNA) molecules can be isolated from a sample using any of a number of procedures, which are well-known in the art, the particular isolation procedure chosen being appropriate for the particular biological sample.

In some embodiments, one or more of the reagents (e.g., a nucleic acid probe) described herein can comprise a detectable label and/or comprise the ability to generate a detectable signal (e.g., by catalyzing a reaction converting a compound to a detectable product). Detectable labels can comprise, for example, a light-absorbing dye, a fluorescent dye, or a radioactive label. Detectable labels, methods of detecting them, and methods of incorporating them into reagents (e.g., antibodies and nucleic acid probes) are well known in the art.

In some embodiments, detectable labels can include labels that can be detected by spectroscopic, photochemical, biochemical, immunochemical, electromagnetic, radio-chemical, or chemical means, such as fluorescence, chemi-fluoresence, or chemiluminescence, or any other appropriate means. The detectable labels can be primary labels (where the label comprises a moiety that is directly detectable or that produces a directly detectable moiety); or secondary labels (where the detectable label binds to another moiety to produce a detectable signal, e.g., as is common in immunological labeling using secondary and tertiary antibodies). The detectable label can be linked by covalent or non-covalent means to the reagent. Alternatively, a detectable label can be linked such as by directly labeling a molecule that achieves binding to the reagent via a ligand-receptor binding pair arrangement or other such specific recognition molecules. Detectable labels can include, but are not limited to, radioisotopes, bioluminescent compounds, chromophores, antibodies, chemiluminescent compounds, fluorescent compounds, metal chelates, and enzymes.

In some embodiments, the expression level of multiple markers of the present disclosure can be determined simultaneously (e.g. a multiplex assay) or in parallel.

In other embodiments, gene expression products (proteins) associated with marker genes of the present disclosure may be detected to determine the presence of PSCs. Such detection techniques are known to persons of skill in the art, and include, for example, ELISA (enzyme linked immunosorbent assay), western blot, FACS, radioimmunological assay; (RIA); sandwich assay; fluorescent in situ hybridization (FISH); immunohistological staining; immunoelectrophoresis; immunoprecipitation; and immunofluorescence using detection reagents such as an antibody or protein binding agents.

In some embodiments, the present disclosure relates to methods for detecting the existence of PSCs, such as ESCs or iPSCs, or both, in a sample. In some embodiments, the sample is a cell-containing composition, a cell-containing solution, a cell aggregate, a cell suspension, or a tissue. In certain embodiments, the sample contains primarily non-PSC cells. In yet further embodiments, the cells in the sample are pre-dominantly cells of a more differentiated state than PSCs, including, e.g., specialized cells, and the method determines the presence and/or amount of PSCs present in the composition. In further embodiments, the cells in the sample are predominantly cells of a more differentiated state than PSCs, having been produced by differentiating PSCs. Hence, the methods described herein can be used to detect and/or quantitate PSCs in a composition, including residual PSCs following a process to differentiate PSCs (to produce, for example, specialized cells).

In some embodiments, a sample of interest (such as a cell-containing composition, a cell-containing solution, a cell aggregate, a cell suspension, or a tissue) is tested to determine the presence of PSCs therein, by detecting the expression of one or more of the markers of the present disclosure in cell(s) within the sample of interest. In some embodiments, the determined expression level of the one or more markers in the sample of interest is also compared to the expression level of the one or more markers from a reference sample known to contain no PSCs, for instance, to confirm the presence or absence of PSCs in the sample of interest.

In other embodiments, the number of PSCs in a sample of interest (such as a cell-containing composition, a cell-containing solution, a cell aggregate, a cell suspension, or a tissue) are quantified by initially measuring the expression level of one or more of the markers of the present disclosure in the sample of interest. The detected expression level of the one or more markers in the sample of interest may then be compared to the expression level of the one or more markers from a reference sample, in which all the cells in the reference sample are PSCs, for example. In other embodiments, the detected expression level of the one or more markers in the sample of interest is then compared to the expression level of the one or more markers from a reference sample which contains a known proportion of PSC cells (with respect to all of the cells in the sample). The proportion of PSCs to total cells may be, for example, 100% or less, 90% or less, 80% or less, 70% or less, 60% or less, 50% or less, 40% or less, 30% or less, 30% or less, 20% or less, 10% or less, 5% or less, 1% or less, 0.1% or less, 0.01% or less, 0.001% or less, 0.0001% or less, 0.00001% or less, 0.000001% or less, 0.0000001% or less, 0.00000001% or less, 0.000000001% or less, or 0.000000001% or less, for example.

Thus, by comparing a measured expression level of one or more of the markers of the present disclosure in a sample of interest to the expression level of the one or more markers from a reference sample containing only PSCs (or containing a known proportion of PSCs with respect to all of the cells in the sample), it is possible to determine the proportion of the cells in the sample of interest that are PSCs.

In accordance with the above methods, if a sample of interest is determined to contain no PSCs, a determination thereof may be made. Additionally, where the sample of interest was obtained from a cell culture, or a tissue culture, the cell or tissue in the culture may be allowed to further expand or proliferate, based on this determination.

Additionally, where the sample of interest relates to a composition of cells, or an engineered tissue, for administration to a subject, for example, the cell or tissue may be administered, with or without a further expansion or proliferation step before the administration, based on this determination.

In other embodiments, the expression of one or more of the markers of the present disclosure can be detected and/or quantified at the single-cell level. That is, the expression of one or more of the markers of the present disclosure can be detected and/or quantified in a single PSC (e.g., single-cell analysis). Single-cell analysis can be performed, for example, after isolation of a single cell (such as by methods known in the art including serial dilution, micromanipulation, laser capture microdissection, FACS, and microfluidics, for example). Additionally, the present disclosure encompasses embodiments in which a sample of interest may only contain a single PSC amongst a plurality of other (non-PSC) cells, and the expression of one or more of the markers of the present disclosure can be detected and/or quantified in that single PSC.

Another aspect of the present disclosure refers to a kit, composition or device for the analysis of the expression of at least one marker gene as described herein. In one embodiment, contemplated is a kit, composition or device for the analysis of the expression of at least one marker gene, comprising at least one primer and/or probe selective for determining the expression level of at least one marker gene. Some embodiments relate to a kit, composition or device comprising at least 10 primers and/or probes, at least 30 primers and/or probes, at least 50 primers and/or probes, or at least 100 primers and/or probes selective for determining the expression level of a plurality of marker genes.

The term "probe" refers to a nucleotide fragment such as RNA or DNA, which may specifically bind to a nucleotide such as mRNA and has a length of several bases to several hundred bases. The probe may be labeled with a radioisotope so that the presence or absence, or the expression level of a specific mRNA may be determined. The probe may be constructed in the form of an oligonucleotide probe, a single stranded DNA probe, a double stranded DNA probe, an RNA probe, etc.

The term "primer" refers to a short nucleotide sequence having a free 3' hydroxyl group, which can undergo base-pairing interaction with a complementary template and can serves as a starting point for replicating the template strand. A primer can initiate DNA synthesis in the presence of a reagent for polymerization (e.g., DNA polymerase or reverse transcriptase) and four different nucleoside triphosphates in suitable buffers and at a suitable temperature.

The term "nucleotide" refers to deoxyribonucleotide or ribonucleotide, and unless otherwise mentioned, the nucleotide may include analogs of a natural nucleotide and analogs including modified sugars or bases.

The probe or primer may be chemically synthesized using a phosphoramidite solid support method or other widely known methods. These nucleotide sequences may also be modified by using various methods known in the art. Examples of such modifications include methylation, capsulation, replacement of one or more native nucleotides with analogues thereof, and inter-nucleotide modifications, for example, modifications to uncharged conjugates (e.g., methyl phosphonate, phosphotriester, phosphoroamidate, carbamate, etc.) or charged conjugates (e.g., phosphorothioate, phosphorodithioate, etc.).

The probe or primer may have a length of 10 nucleotides or more, or may have a length of 20 nucleotides or more. The probe or primer may have a length of 100 nucleotides or less, 90 nucleotides or less, 80 nucleotides or less, 70 nucleotides or less, 60 nucleotides or less, 50 nucleotides or less, 40 nucleotides or less, 30 nucleotides or less, or 25 nucleotides or less.

A kit can also include instructions for using the components of the kit to practice the methods. The instructions for practicing the methods are generally recorded on a suitable recording medium. For example, the instructions may be printed on a substrate, such as paper or plastic, etc. The instructions may be present in the kits as a package insert or in the labeling of the container of the kit or components thereof (e.g., associated with the packaging or subpackaging).

Experimental

Non-limiting embodiments of the present invention are illustrated in the following Examples. Efforts have been made to ensure accuracy with respect to numbers used (e.g., amounts, concentrations, percent changes, and the like), but some experimental errors and deviations should be accounted for. It should be understood that these Examples are given by way of illustration only and are not intended to limit the scope of what the inventor regards as various embodiments of the present invention. Not all of the following steps set forth in each Example are required nor must the order of the steps in each Example be as presented.

Example 1

RNA-Seq Analysis Identifying PSC-Specific Markers

For RNA-seq analysis, mRNA from a large collection of iPSCs was isolated. These iPSCs were produced by reprogramming somatic cells obtained from a variety of different donors. The iPSCs used in this work were from a wide range of culture conditions, and passage numbers. Many of these samples came from the 2019 "Well Characterized Stem Cell" studies which included culturing of iPSCs under various O2, media and matrix combinations, as well as long and short passaging. It is a very diverse collection proving that the markers are robust with respect to how they were cultured.

mRNA was also isolated from a variety of differentiated cell samples, representative of diverse specialized and partially-differentiated cell types (these differentiated and partially-differentiated cell samples included cells produced from iPSCs). Further, mRNA was also isolated from cell samples at intermediate time points during the differentiation process; and from cells/tissues at varying intermediate stages (from partially differentiated to fully differentiated).

Unless indicated otherwise, expression analysis on the iPSCs, the differentiated and partially-differentiated cells, the cell samples at intermediate time points during the differentiation process, and the cells/tissues at varying intermediate stages between partially differentiated and fully differentiated, was conducted at least in triplicate.

After isolation of mRNAs from the samples, the mRNAs were subjected to whole transcriptome RNASeq analysis, using Illumina® technology. The workflow of analysis of mRNA was as follows: Raw RNASeq (fastq) was QC'd for quality using the FastQC program, aligned to the HG38 reference genome using the HiSat2 program, and then processed with CuffDiff to create FPKM values. Many other methods have been applied to these data, however for the purposes of the patent, this is the only analysis needed. The resulting data were then processed using a combination of HiSat tools and the Tuxedo suite (TopHat®, CuffLinks, CuffDiff, etc.) to produce FPKM values for >58,000 genes from the HG38 reference genome and the Ensembl® annotation set.

Figure 14:
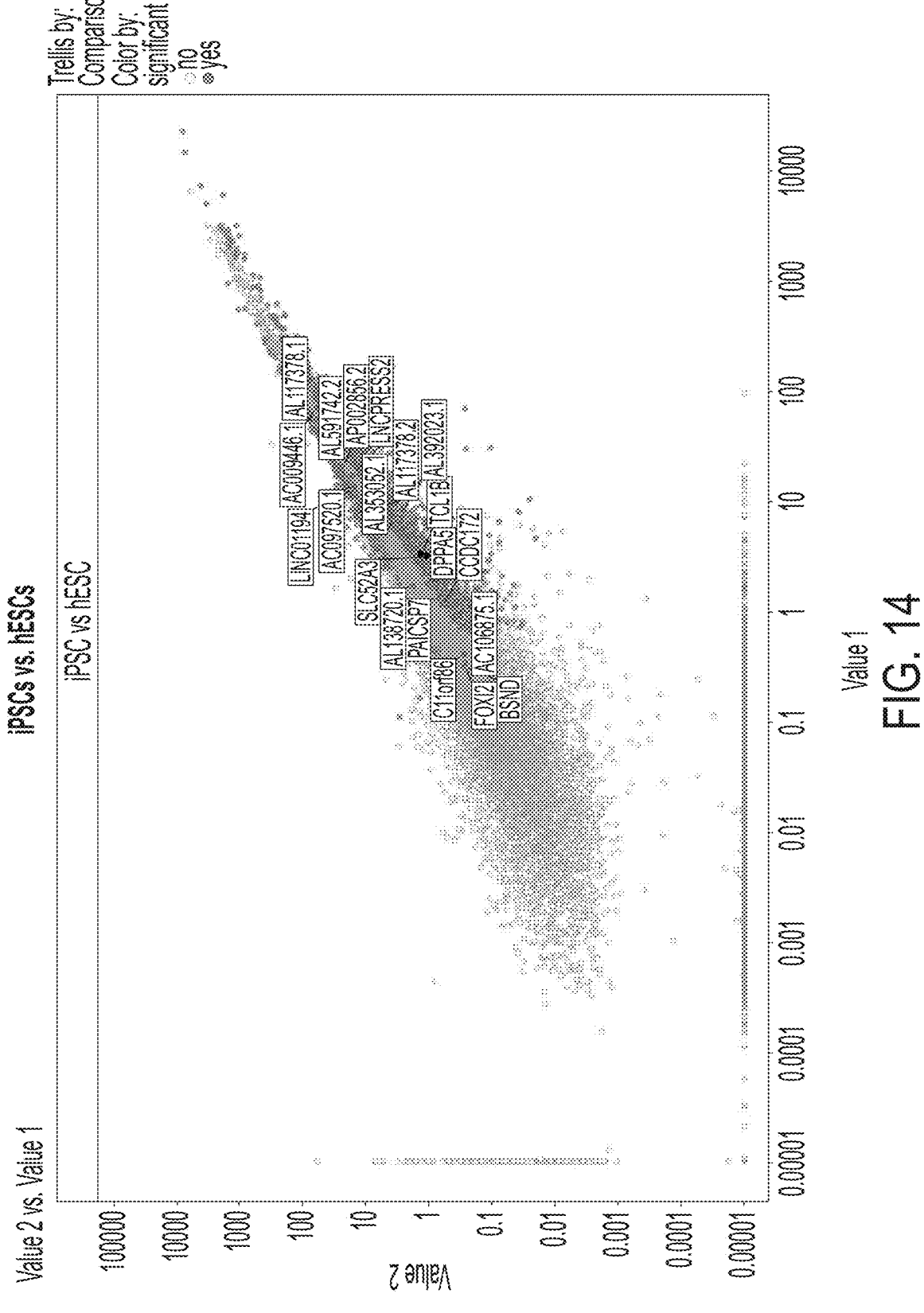
FIG. 14 depicts a plot of the $\log_{10}$ FPKM values for various mRNAs in mRNA samples collected from iPSCs (X-axis) and human ESCs (Y-axis).
Figure 15:
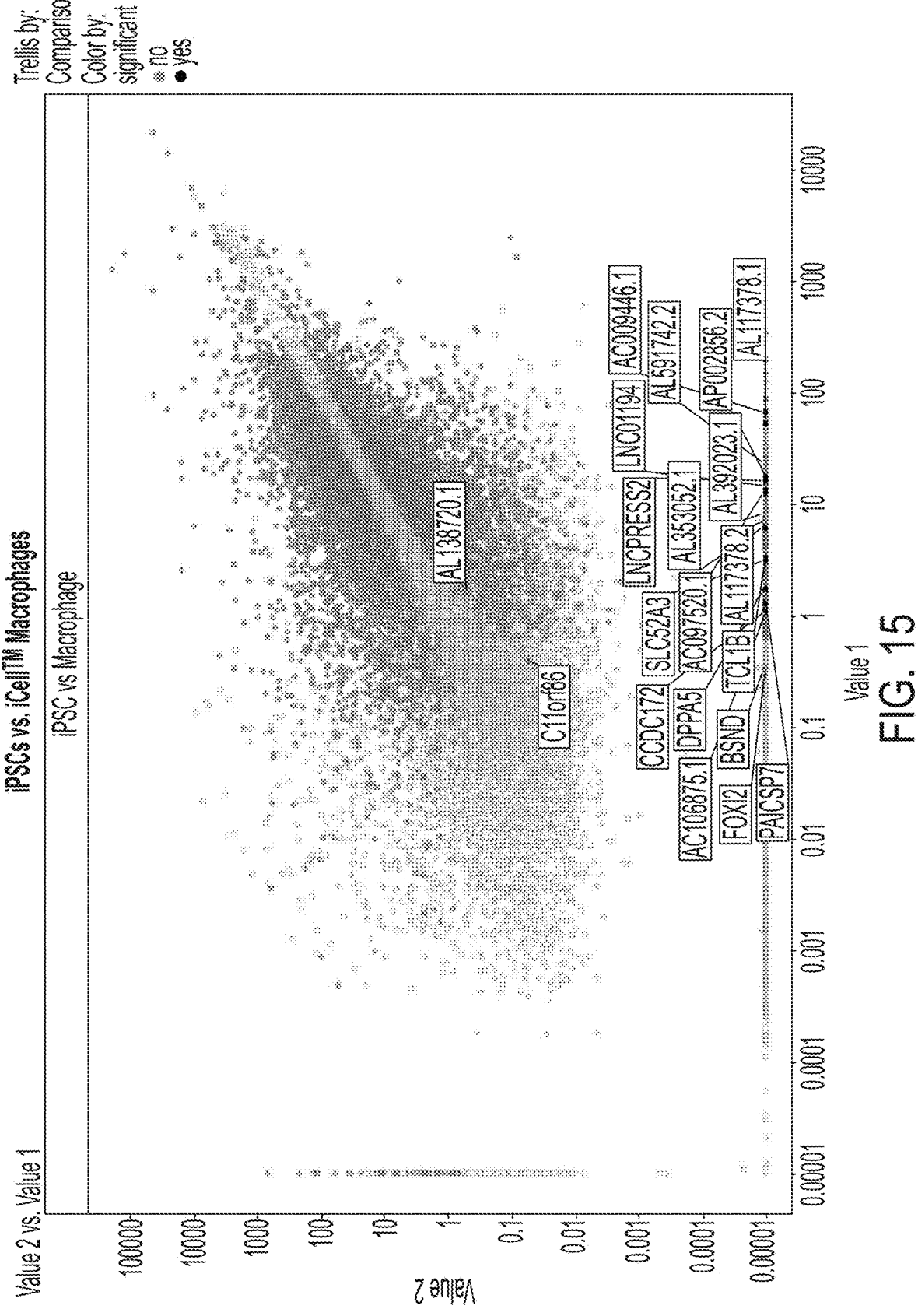
FIG. 15 depicts a plot of the $\log_{10}$ FPKM values for various mRNAs in mRNA samples collected from iPSCs (X-axis) and human macrophages (iCell® Macrophages; Y-axis).
Figure 16:
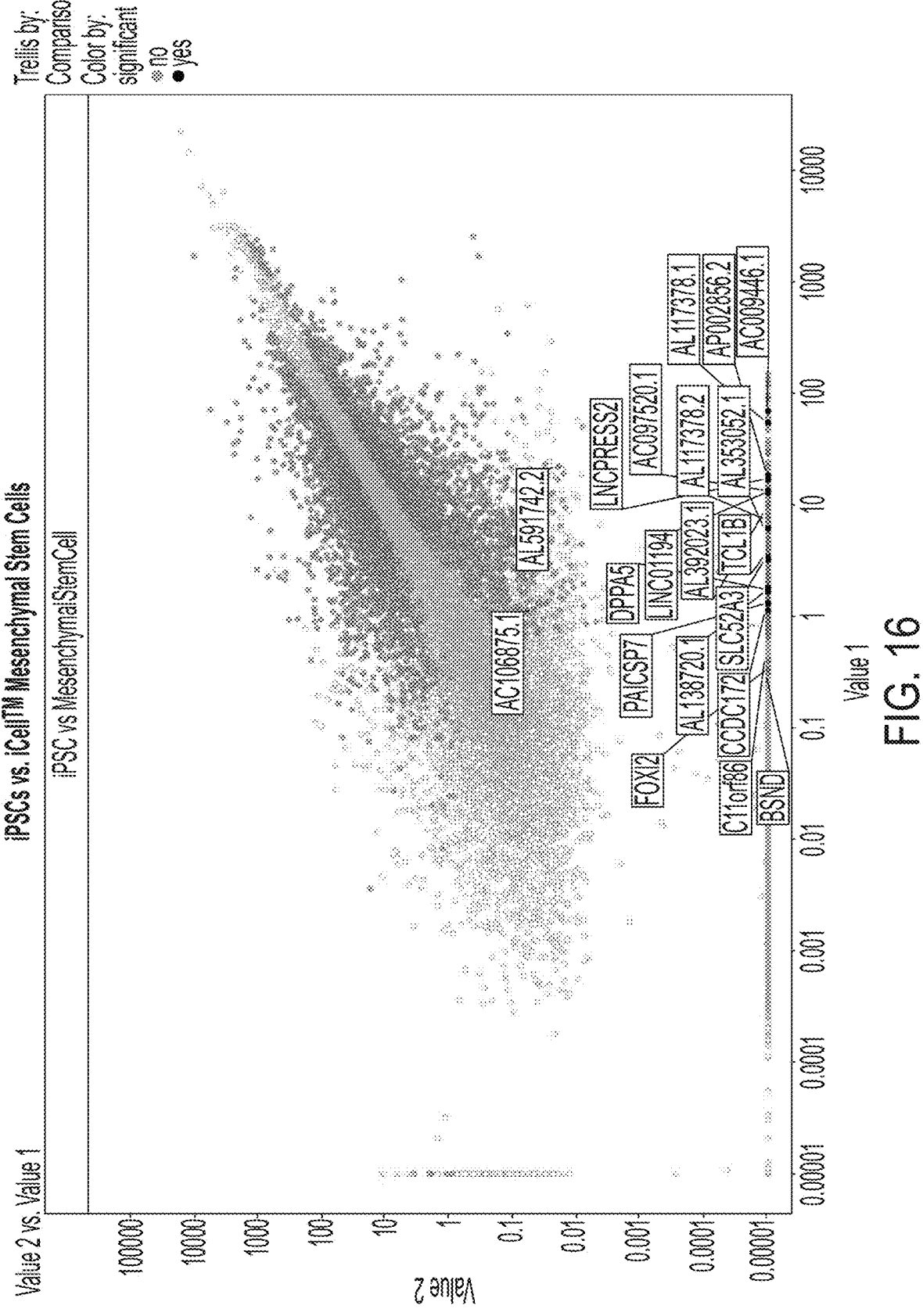
FIG. 16 depicts a plot of the $\log_{10}$ FPKM values for various mRNAs in mRNA samples collected from iPSCs (X-axis) and human mesenchymal stem cells (iCell® Mesenchymal Stem Cells; Y-axis).
Figure 17:
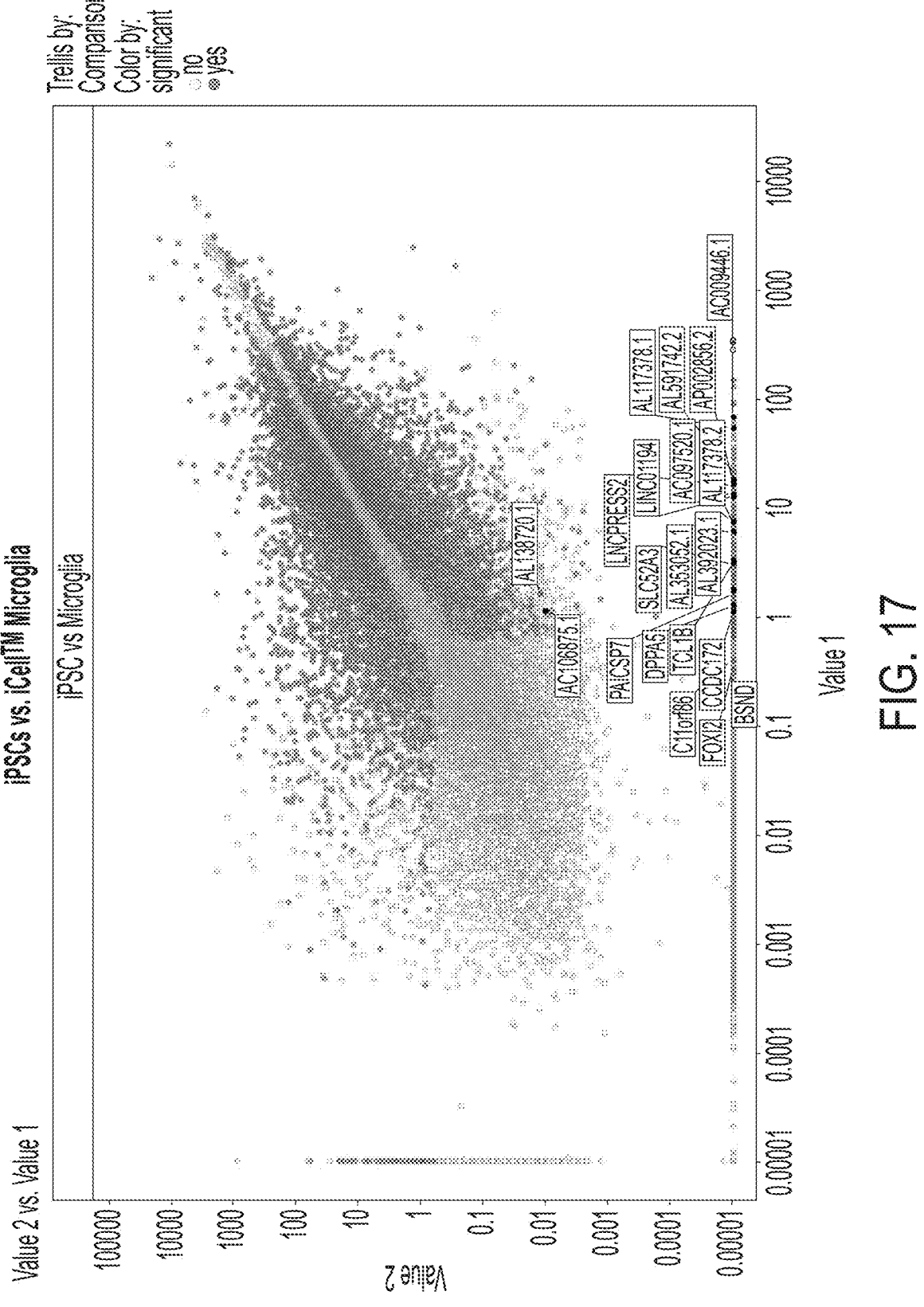
FIG. 17 depicts a plot of the $\log_{10}$ FPKM values for various mRNAs in mRNA samples collected from iPSCs (X-axis) and human microglia (iCell® Microglia; Y-axis).
Figure 18:
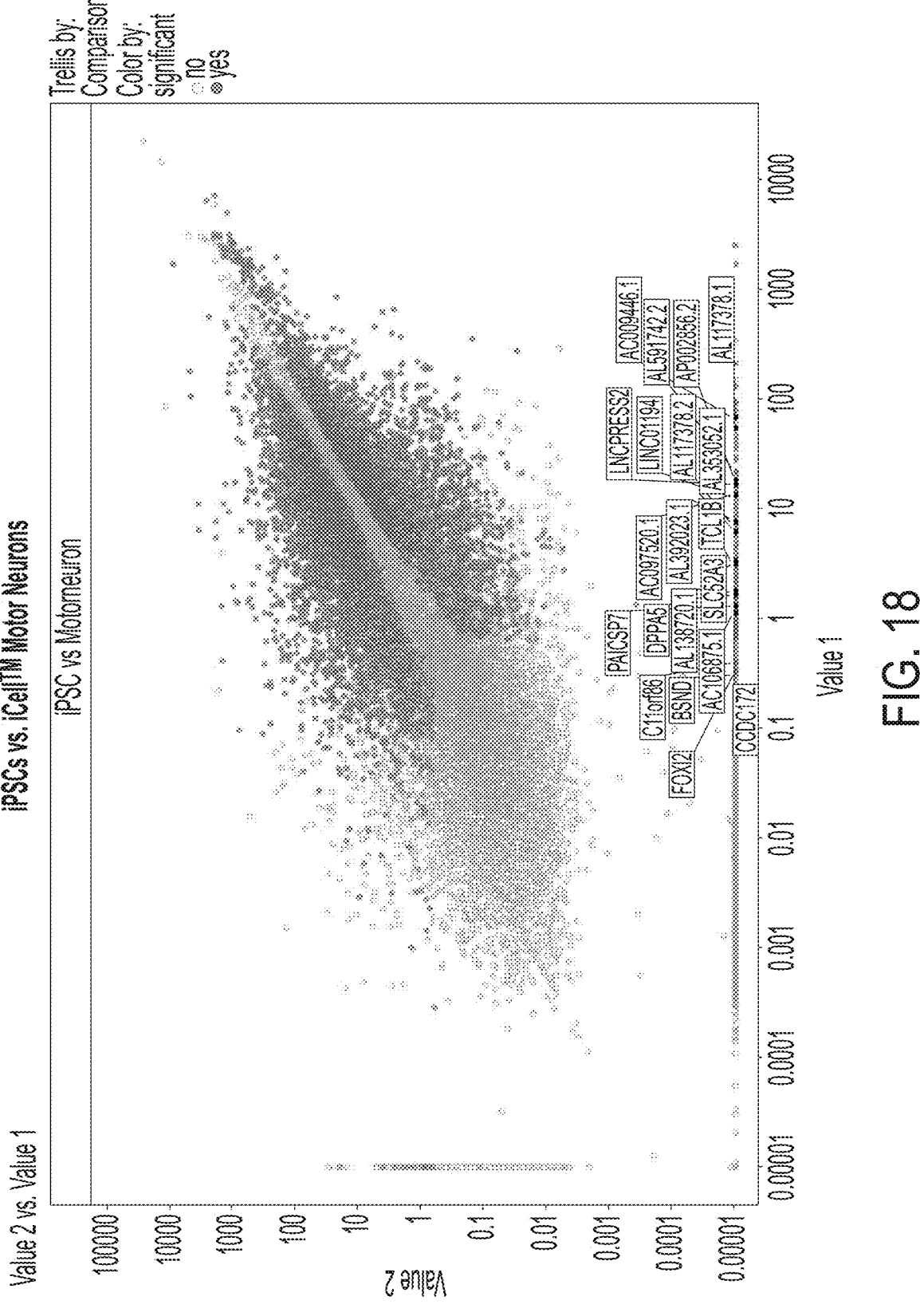
FIG. 18 depicts a plot of the $\log_{10}$ FPKM values for various mRNAs in mRNA samples collected from iPSCs (X-axis) and human motor neurons (iCell® Motor Neurons; Y-axis).
Figure 19:
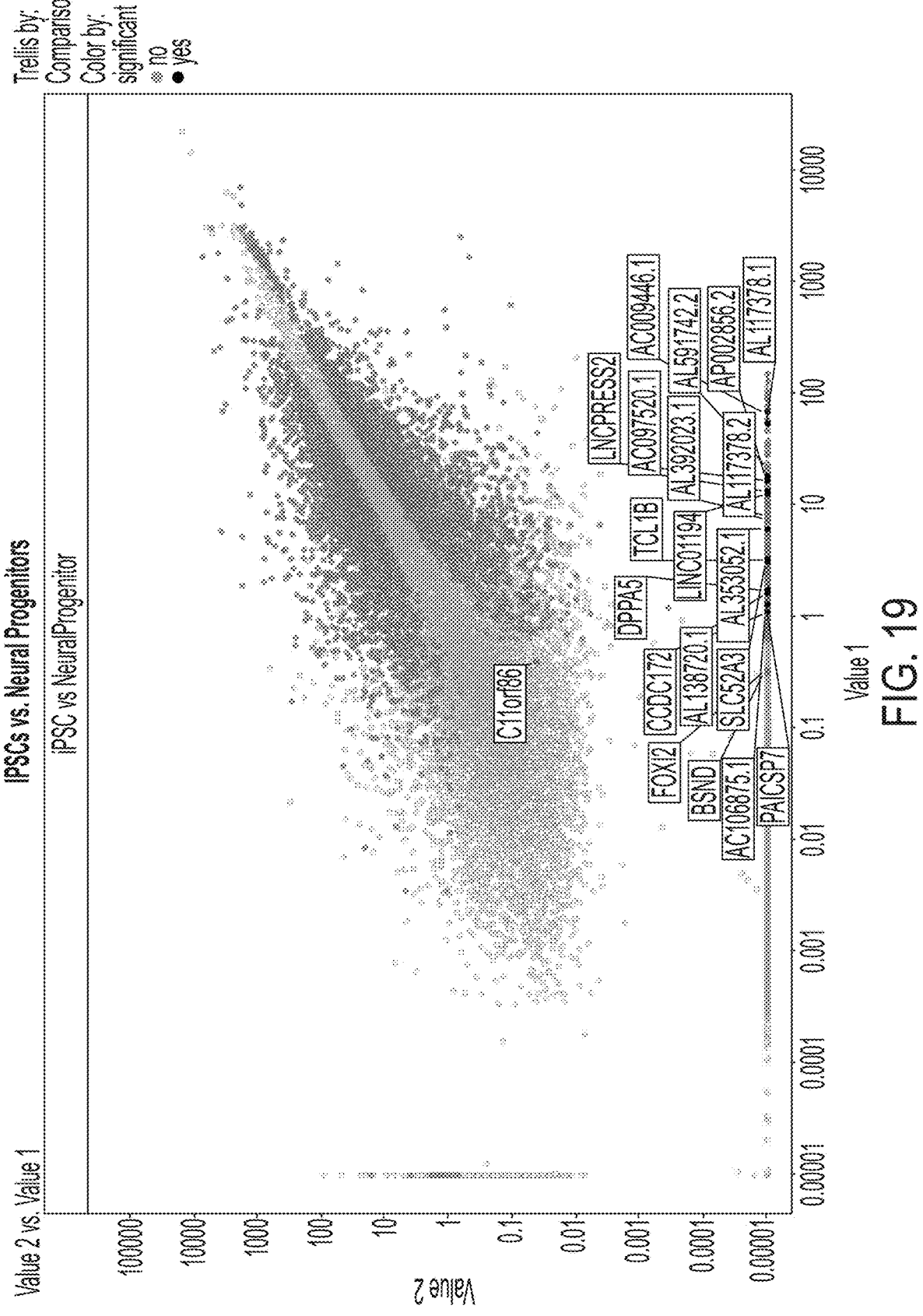
FIG. 19 depicts a plot of the $\log_{10}$ FPKM values for various mRNAs in mRNA samples collected from iPSCs (X-axis) and human neural progenitor cells (Y-axis).
Figure 20A:
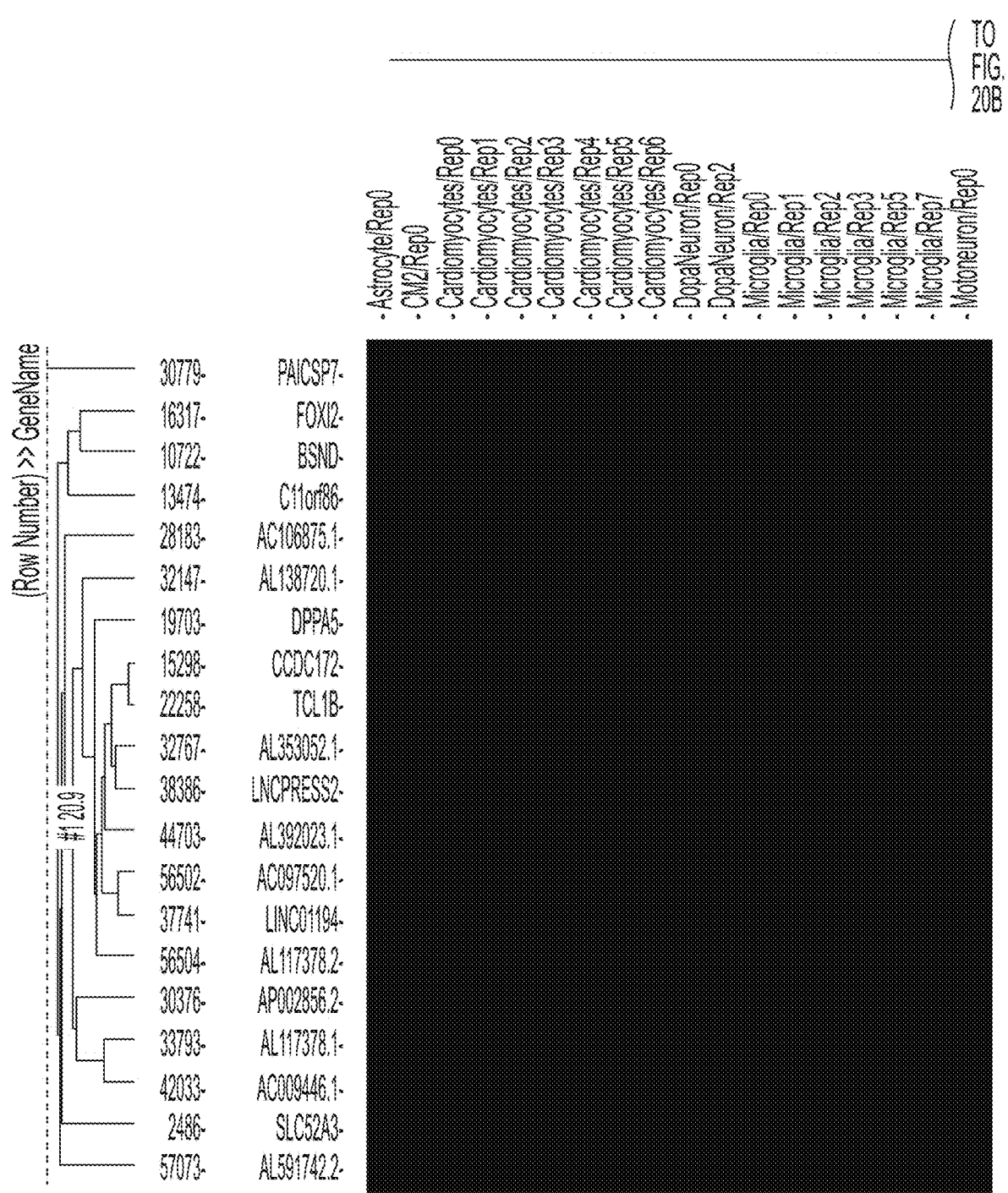
FIGS. 20A-20E depict the results of hierarchical clustering of different cell types based on a panel of PSC-specific markers.
Figure 20B:
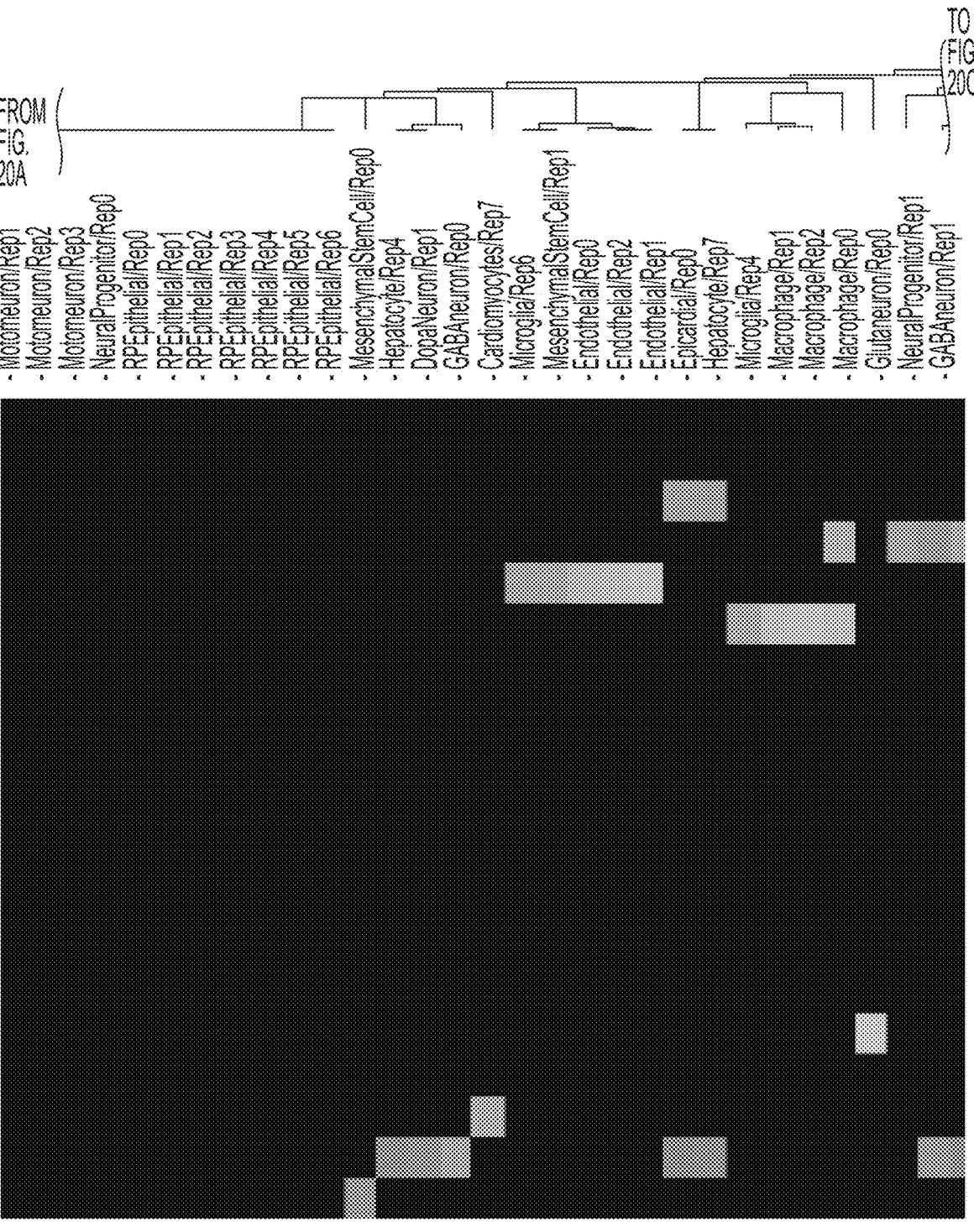
Figure 20C:
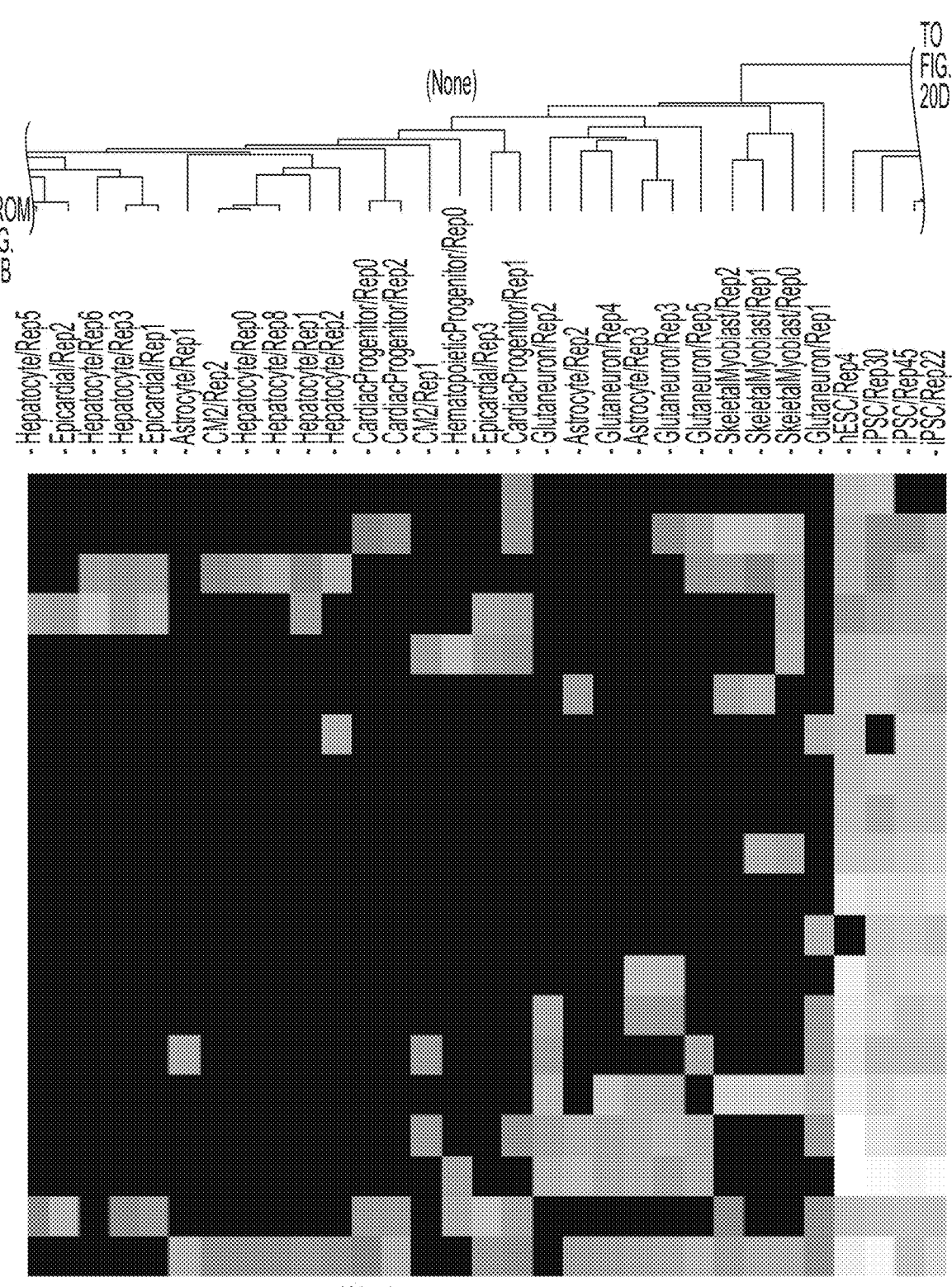
Figure 20D:
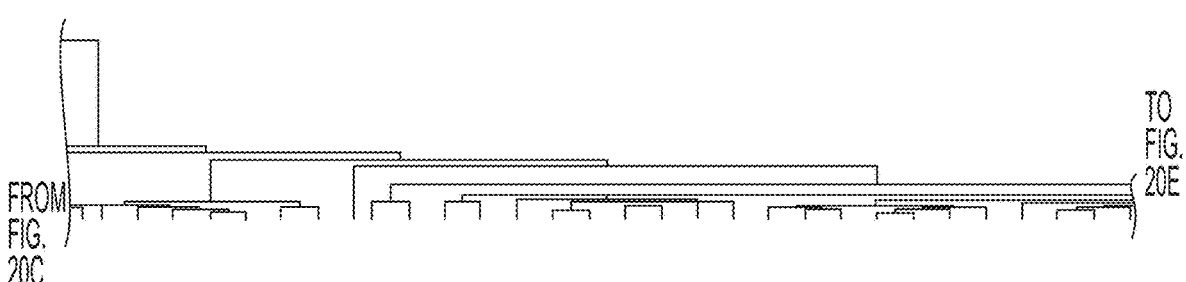
Figure 20D:
Figure 20D:
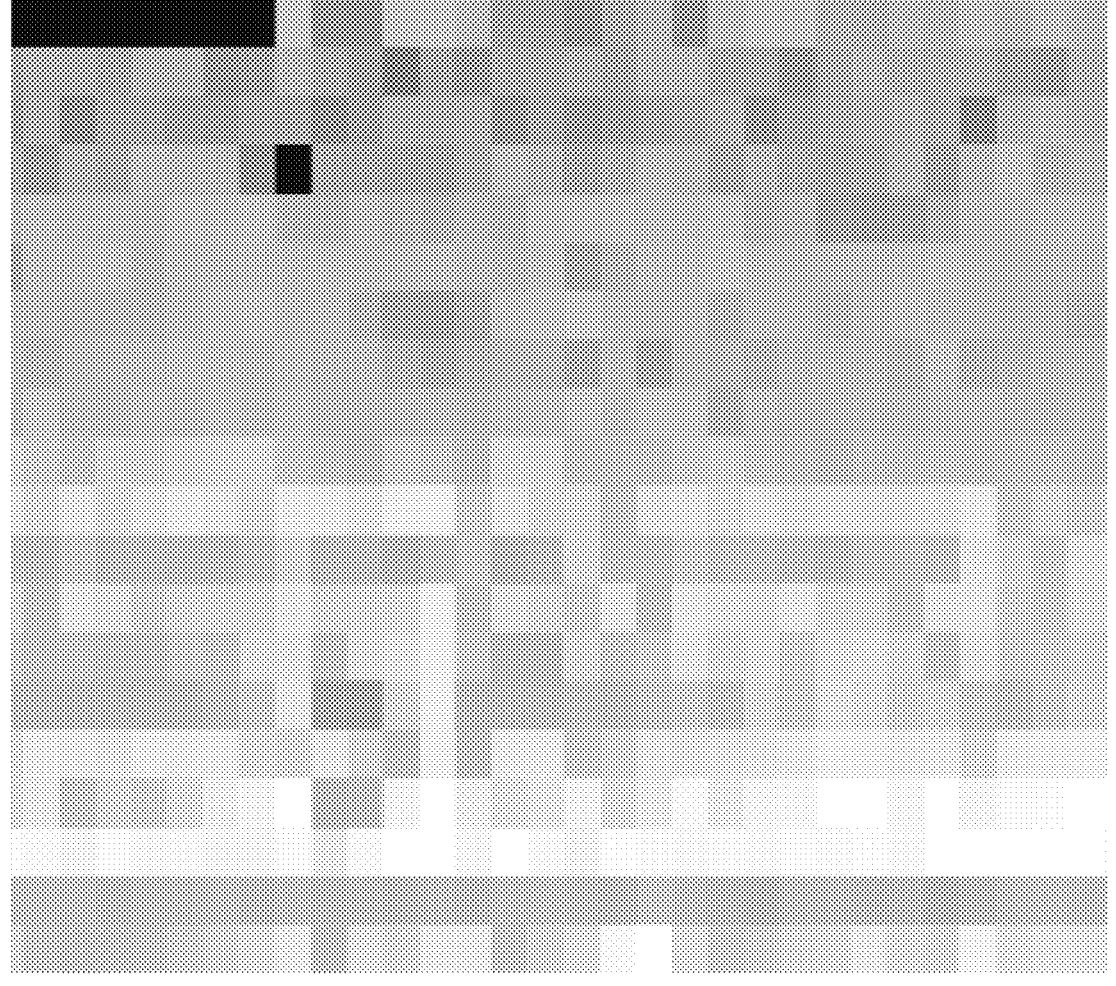
Figure 20E:

FIGS. 1-19 depict plots of the $\log_{10}$ FPKM (Fragments Per Kilobase Million) values for various mRNAs in mRNA samples collected from iPSCs, and from different cell types. FIGS. 1-13 and 15-19 demonstrate the identification of multiple marker genes that are selectively expressed only in pluripotent stem cells, and not expressed in cells or tissues at later stages of differentiation. FIG. 14 depicts a comparison between iPSCs and ESCs, showing that the identified markers are expressed not just in iPSCs, but also in ESCs, thereby demonstrating that these marker genes are useful for detecting both iPSCs and ESCs.

Example 2

Hierarchical Clustering of Cell Types Based on an iPSC-Specific Marker Panel

From the various cell samples measured in Example 1, a curated subset of the cell samples were analyzed using hierarchical clustering, based on their $\log_{10}$ FPKM values. The clustering method used was Unweighted Pair-Group Method with Arithmetic Mean (UPGMA), and the distance metric employed was Euclidian distance. FIGS. 20A-20E is a Hierarchical Clustering of gene expression. The plot is rotated 90 degrees in the document. The two axes are Patent Markers (short axis) vs screened tissue types (long axis). Dark blue represents no expression increasing to red for high expression. At the edges of the plot are two dendrograms representing how distant individual groups are to each other, only the vertical branch lengths are meaningful as a distance measure. FIGS. 20A-20E show how this gene panel can clearly separate iPSC tissues (right side) from other tissues (left side) with a large distance of separation. As shown in FIGS. 20A-20E, this cluster analysis demonstrated that the identified PSC-specific markers are able to accurately distinguish PSCs (including ESCs and iPSCs), from all other non-PSC cell types.

Example 3

Figure 21:
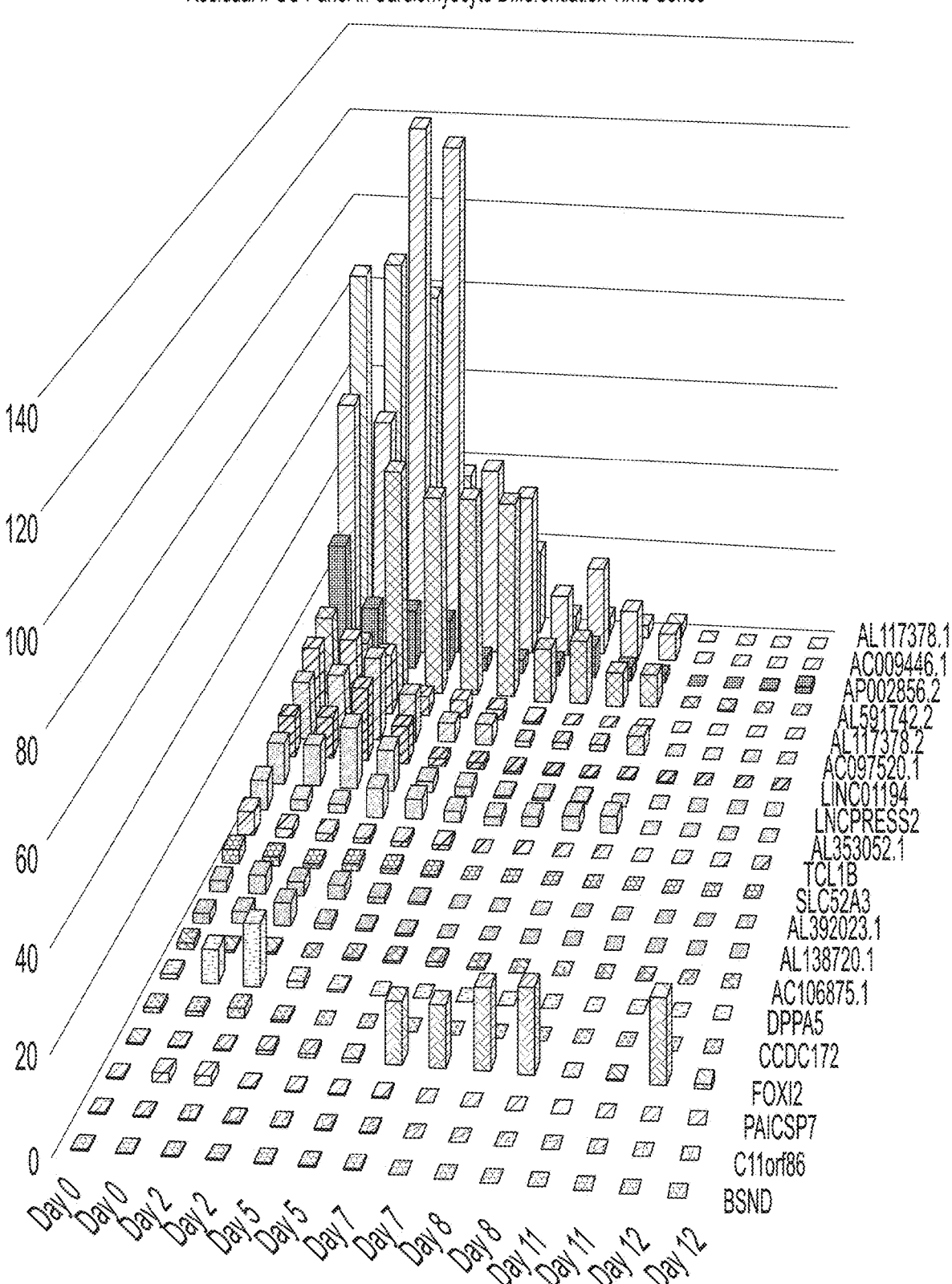
FIG. 21 depicts a histogram showing the expression level (Z-axis) of various PSC-specific markers (Y-axis) during a 12-day time course study during which iPSCs were differentiated into cardiomyocytes. Time (in days) is depicted on the X-axis.

Analysis of iPSC-Specific Marker Panel Using Time Course Study of Differentiation To measure the change in expression of the identified iPSC-specific markers during a time-course study of differentiation, iPSCs were differentiated into cardiomyocytes under a controlled protocol. Samples were collected at specific time points upon, and after, the initiation of the differentiation protocol (at days 0, 2, 5, 7, 8, 11 and 12), and expression of the iPSC-specific markers was determined. As shown in FIG. 21, expression of the iPSC-specific markers generally declined over the time-course of differentiation, further confirming that the marker genes tested are specific for PSCs.

The invention claimed is:

1. A method for detecting pluripotent stem cells, said method comprising:
   (a) obtaining a sample of interest containing a plurality of cells;
   (b) determining that the sample of interest does not contain pluripotent stem cells by analyzing said sample of interest to detect n expression of at least one transcript having a corresponding complementary DNA (cDNA) sequence that comprises a nucleotide sequence having at least 90% sequence identity to a full length of a nucleotide sequence selected from the group consisting of SEQ ID NOs: 1-17 and 19-28, wherein it is determined that the sample of interest does not contain pluripotent stem cells when the expression of said at least one transcript is not detected, and
   (c) producing a product containing differentiated cells using the sample of interest determined not to contain pluripotent stem cells.

2. The method of claim 1, wherein the pluripotent stem cells are induced pluripotent stem cells.

3. The method of claim 1, wherein the pluripotent stem cells are embryonic pluripotent stem cells.

4. The method of claim 1, wherein said plurality of cells in said sample of interest is in the form of a cell mixture, a cell aggregate, or a tissue.

5. The method of claim 1, wherein the expression of said at least one transcript is detected by a process comprising a technique selected from the group consisting of droplet digital polymerase chain reaction (dd-PCR), polymerase chain reaction (PCR), reverse-transcriptase PCR (RT-PCR), quantitative PCR, quantitative RT-PCR, Northern blot analysis, differential gene expression, RNA protection assay, microarray analysis, hybridization assay, and next-generation sequencing.

6. The method of claim 5, wherein said technique comprises microarray analysis or next-generation sequencing.

7. The method of claim 1, wherein said at least one transcript has a corresponding complementary DNA (cDNA) sequence that comprises a nucleotide sequence having at least 90% sequence identity to a nucleotide sequence selected from the group consisting of SEQ ID NOs: 1, 4-6 and 24.

8. The method of claim 1, wherein the cDNA sequence comprises a nucleotide sequence selected from the group consisting of SEQ ID NOs: 1-17 and 19-28.

9. The method of claim 1, wherein the product containing differentiated cells is a therapeutic product.

10. A method for detecting pluripotent stem cells, said method comprising:

(a) obtaining a sample of interest containing a plurality of cells;

(b) determining that the sample of interest contains substantially no pluripotent stem cells by (b)(1) measuring, in said sample of interest, an expression level of at least one transcript having a corresponding complementary DNA (cDNA) sequence that comprises a nucleotide sequence having at least 90% sequence identity to a full length of a nucleotide sequence selected from the group consisting of SEQ ID NOs: 1-17 and 19-28, and (b)(2) measuring the expression level of said at least one transcript in at least one reference sample, wherein said at least one reference sample comprises a plurality of cells, and wherein said at least one reference sample contains substantially no pluripotent stem cells, wherein it is determined that the sample of interest contains substantially no pluripotent stem cells when the expression level detected in step (b)(1) is equal to or less than the expression level measured in step (b)(2); and (c) producing a product containing differentiated cells using the sample of interest determined to contain substantially no pluripotent stem cells.

11. The method of claim 10, wherein the pluripotent stem cells are induced pluripotent stem cells.

12. The method of claim 10, wherein the pluripotent stem cells are embryonic pluripotent stem cells.

13. The method of claim 10, wherein said plurality of cells in said sample of interest is in the form of a cell mixture, a cell aggregate, or a tissue.

14. The method of claim 10, wherein the expression of the at least one transcript is measured by a process comprising a technique selected from the group consisting of dd-PCR, polymerase chain reaction (PCR), reverse-transcriptase PCR (RT-PCR), quantitative PCR, quantitative RT-PCR, Northern blot analysis, differential gene expression, RNA protection assay, microarray analysis, hybridization assay, and next-generation sequencing.

15. The method of claim 10, wherein said at least one transcript has a corresponding complementary DNA (cDNA) sequence that comprises a nucleotide sequence having at least 90% sequence identity to a nucleotide sequence selected from the group consisting of SEQ ID NOs: 1, 4-6 and 24.

16. The method of claim 10, wherein the cDNA sequence comprises a nucleotide sequence selected from the group consisting of SEQ ID NOs: 1-17 and 19-28.

17. The method of claim 10, wherein the product containing differentiated cells is a therapeutic product.

18. A method for quantifying the number of pluripotent stem cells in a product containing differentiated cells, said method comprising:

(a) obtaining the product containing differentiated cells;

(b) measuring, in said product containing differentiated cells, a level of expression of at least one transcript having a corresponding complementary DNA (cDNA) sequence that comprises a nucleotide sequence having at least 90% sequence identity to a full length of a nucleotide sequence selected from the group consisting of SEQ ID NOs: 1-17 and 19-28; and (c) measuring a level of expression of said at least one transcript in at least one reference sample, wherein said at least one reference sample comprises a plurality of cells, wherein said at least one reference sample comprises pluripotent stem cells, and wherein substantially all of the cells in said at least one reference sample are pluripotent stem cells.

19. The method of claim 18, wherein the pluripotent stem cells are induced pluripotent stem cells.

20. The method of claim 18, wherein the pluripotent stem cells are embryonic pluripotent stem cells.

21. The method of claim 18, wherein said plurality of cells in said product containing differentiated cells is in the form of a cell mixture, a cell aggregate, or a tissue.

22. The method of claim 18 wherein the level of expression of the at least one transcript is measured by a process comprising a technique selected from the group consisting of dd-PCR, polymerase chain reaction (PCR), reverse-transcriptase PCR (RT-PCR), quantitative PCR, quantitative RT-PCR, Northern blot analysis, differential gene expression, RNA protection assay, microarray analysis, hybridization assay, and next-generation sequencing.

23. The method of claim 18, wherein said at least one transcript has a corresponding complementary DNA (cDNA) sequence that comprises a nucleotide sequence having at least 90% sequence identity to a nucleotide sequence selected from the group consisting of SEQ ID NOs: 1, 4-6 and 24.

24. The method of claim 18, wherein the cDNA sequence comprises a nucleotide sequence selected from the group consisting of SEQ ID NOs: 1-17 and 19-28.

25. The method of claim 18, wherein the product containing differentiated cells is a therapeutic product.

* * * * *